United States Patent [19]
Vasquez et al.

[11] Patent Number: 5,935,803
[45] Date of Patent: Aug. 10, 1999

[54] METHODS TO IDENTIFY IMMUNOMODULATORS USING COGNATE INTERACTION OF PKC-THETA

[75] Inventors: Nicki J. Vasquez; Dorit Ron, both of San Francisco; Anna F. Voronova, San Bruno; Eugene W. Napolitano, San Francisco, all of Calif.

[73] Assignee: Terrapin Technologies, Inc., South San Francisco, Calif.

[*] Notice: This patent is subject to a terminal disclaimer.

[21] Appl. No.: 08/665,647

[22] Filed: Jun. 18, 1996

Related U.S. Application Data

[62] Continuation-in-part of application No. 08/190,802, Feb. 1, 1994, Pat. No. 5,519,003, and a continuation-in-part of application No. 08/594,447, Jan. 31, 1996, Pat. No. 5,776,716, which is a continuation-in-part of application No. 08/541,964, Oct. 10, 1995, Pat. No. 5,783,405, and a continuation-in-part of application No. 08/473,089, Jun. 7, 1995, application No. 08/477,346, Jun. 7, 1995, and application No. 08/487,072, filed as application No. PCT/US95/01210, Jan. 31, 1995.

[51] Int. Cl.$^6$ .............................. C12Q 1/02; C12Q 1/48; C12Q 1/68

[52] U.S. Cl. ................................. 435/15; 435/6; 435/7.8; 435/29

[58] Field of Search .................................. 435/6, 7.8, 15, 435/29

[56] References Cited

U.S. PATENT DOCUMENTS

| 5,283,173 | 2/1994 | Fields et al. ................................ 435/6 |
| 5,352,660 | 10/1994 | Pawson ...................................... 514/12 |

FOREIGN PATENT DOCUMENTS

WO 95/21252  1/1995  WIPO.

OTHER PUBLICATIONS

Derwent Publications Ltd., AN 94–026226 (1994).

Meller et al., Mol. Cell. Biol. 16:5782–5791, 1996.

Dalrymple, M.A. et al., "The Product of the PRP4 Gene of *S. cerevisiae* Shows Homology to β Subunits of G Proteins," *Cell* 58:811–812 (1989).

Dynlacht, B.D. et al., "The dTAF...80 subunit of Drosphila TFIID contains β–transducin repeats," *Nature* 363: 176–179 (1993).

Fong, H.K.W. et al., "Repetitive segmental structure of the transducin β subunit: Homology with the CDC4 gene and identification of related mRNAs," *Proc. Natl. Acad. Sci. USA* 83: 2162–2166 (1986).

Guillemot, F. et al., "Physical linkage of a guanine nucleotide–binding protein–related gene to the chicken major histocompatibility complex," *Proc. Natl. Acad. Sci. USA* 86: 4594–459 (1989).

Keleher, C.A. et al., "Ssn6–Tup 1 Is a General Repressor of Transcription in Yeast," *Cell* 68: 709–719 (1992).

Mochly–Rosen, D. et al., "Identification of intracellular receptor proteins for activated protein kinase C," *Proc. Natl Acad. Sci USA* 88: 3997–4000 (1991).

Mochly–Rosen, D. et al., "Intracellular Receptors for Activated Protein Kinase C," *J. Biol. Chem* 266(23): 14866–14868 (1991).

Peitsch, M.C. et al., "Sequence similarity of phospholipase A2 activating protein and the G protein β–subunits: a new concept of effector protein activation in signal transduction?," *TIBS* 18(8): 292–293 (1993).

(List continued on next page.)

*Primary Examiner*—Eric Grimes
*Attorney, Agent, or Firm*—Kate H. Murashige

[57] ABSTRACT

Modulators of the immune system can be identified by determining the ability of candidate substances to affect the interaction of PKC-theta or a fragment thereof with its cognate. The interaction can be measured using binding of the cognate as an index, or can be measured using a physiological response.

8 Claims, 17 Drawing Sheets

OTHER PUBLICATIONS

Ron, D. et al., "An Autoregulatory Region in Protein Kinase C: The Pseudoanchoring Site" *Proc. Natl. Acad. Sci. USA* 92:492–496 (1995).

Ron, D. et al. "Agonists and Antagonists of Protein Kinase C Function, Derived from its Binding Proteins" *J. Biol. Chem.* 269:21395–21398 (1994).

Ron, D. et al. "Cloning of an Intracellular Receptor for Protein Kinase C: A Homolog of the Beta Subunit of G Proteins" *Proc. Natl. Acad. Sci. USA* 91:839–843 (1994).

Ruggieri, R., et al. "MSI1, a Negative Regulator of the RAS–cAMP Pathway in *Saccharomyces Cerevisiae*" *Proc. Natl. Acad. Sci. USA* 86:8778–8782 (1989).

Smith, B.L. and Mochly–Rosen, D., "Inhibition of Protein Kinase C Function by Injection of Intracellular Receptors for the Enzyme," *Biochem. Biophys. Res. Comm.* 188(3): 1235–1240 (1992).

Takagaki, Y. and Manley, J.L., "A Human Polyadenylation Factor Is a G Protein β–subunit Homologue," *J. Biol. Chem* 267(33):23471–23474.

Tamaki, M. et al. "Rat Lipocortin I cDNA" *Nucleic Acids Res.* 15:7637 (1987).

van der Voorn, L. and Ploegh, H.L., "The WD–40 repeat," *FEBS Lett.* 307(2): 131–134 (1992).

Wallner, B., et al. "Cloning and Expression of Human Lipocortin, a Phospholipase A2 Inhibitor with Potential Anti–Inflammatory Activity" *Nature* 320:77–81 (1986).

Weinstat–Saslow et al., "A Transducin–like Gene Maps to the Autosomal Dominant Polycystic Kidney Disease Gene Region" *Genomics* 18:709–711 (1993).

Williams, F.E. and Trumbly, R.J., "Characterization of TUP1, a Mediator of Glucose Repression in *Saccharomyces cerevisiae*," *Mol. Cell. Biol.* 10(12): 6500–6511 (1990).

Williams, F.E. et al., "The CYC8 and TUP1 Proteins Involved in Glucose Repression in *Saccharomyces cerevisiae* Are Associated in a Protein Complex," *Mol. Cell. Biol.* 11(6): 3307–3316 (1991).

Blot: anti-pTyr antibody

Blot: anti-Fyn antibody

Anti PKC-theta
Control Cells
Activated Cells p59 Fyn

1 mgcvqckdke aaklteerdg slnqssgyry gtdptpqhyp sfgvtsipny 50

```
                                                              fyn2
51 nnfhaaggqg ltvfggvnss shtgtlrtrg gtgvtlfval ydyartedd lsfhkgekfq ilnssegdwwea 122
                                                              fyn3
123 rslttgetgyipsnyvapvdsiqaeewyfgklgrk daerqllsfgnprgtfliresqt tkgaysisird wddm 195

196 kgdhvkhykirkldnggyyittraqetlqqlvq     hysekadglcfnltviassctpqtsglakdawevarrslcl 270
``` ekklgqgcfa evwlgtwngn tkvaiktlkpgtmspesfle eaqimkklkh dklvqlyavv seepiyivte
ymskgslldflkdgegralk lpnlvdmaaq vaagmayier mnyihrdlrs anilvgnglickiadfglar liedneytar
                fyn4
qgakfpikwt apeaalygrf tiksdvwsfgilltelvtkg rvpypgmnnr evleqvergyrmpcpqdcpislhelmihc
wkkdpeerptf eylqgfledy ftatepqyqp genl

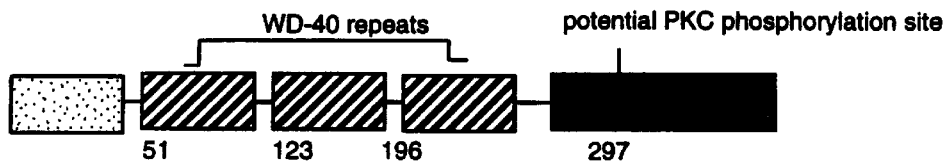

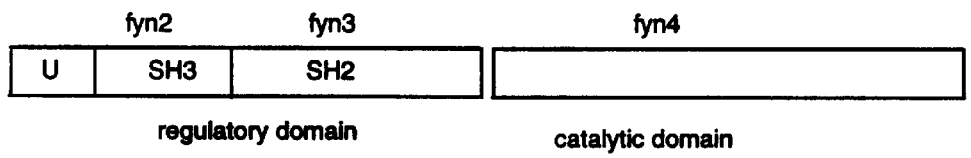

KTLK (bold, underline) = PKC phosphorylation site
underline = RACK1-homologues sequences
Box = WD-40 - like domain
1-14 myrstylation site
14-88 Unique region
88-143 SH3
150-233 SH2
250-516 catalytic domain

FIG. 9

2-10.SEQ

GCCTCAGCACAGCCCTTCCTCTGCTGCCTGTGCGGTATGATCTTTCCTGGGAGG
ACTGGCTACAGGCGTCATCTGCGCCAGGCTCATGGAGCTTCTGCCATGACTGA
GGGCTCAGAAGAAGAGGAGGAAGGCACAGCAGAAACAGCCTCTAC
CCATAGTCCTCCCCTGCAACTCTCAGAAGCAGAGCTGCTGAATCAACTGCAGC
GTGAGGTGGAAGCTCTAGATGGAGCAGGTTATGGTCATATTTGTGGTTGCTGT
GGTCAGACCTATGATGACCTGGGGAGCCTGGAGCGTCACCACCAAAGTCAAAG
TTCTAGCAATAGGACAGAGAATGTTCCTAGCCATTTGGAAGGAGCAGGTGATG
CAACAGAAATGGTTGCAGATCATGGCTTTGAGGGCACAGTGACCTCCGTCTCA
GAAGAAGGTGGGGACATAAAGTCTGAAGAGGGAGTAGGTGGCACAGTTGCAG
ACAGCCTTTGCATGCAGGCTGGTGAAAGCTTTCTGGAGTCCCACCCTCGCCCTT
TCCAATGTAACCAGTGTGGCAAGACCTATCGCCACGGAGGCAGCTTGGTAAAC
CACCGAAAGATCCACCAGACAGGTGATTTCATCTGTCCTGTCTGTTCCCGCTGC
TACCCCAATCTGGCTGCCTACCGGAATCATCTGCGGAATCACCCTCGCTGCAAA
GGCTCAGAGCCCCAAATGGGGCCCATCTCAGAAGCAGGAGGCTGCAGTGAGC
CCCAGAATGCAGCAGAGGCAGGGCAGGAGCAGGCTGTCATAGGGCAACTCCA
GGAAGAGCTTAAAGTGGAGCCCTTGGAGGAGCTGGCAGGTGTCAAAGAAGAA
GTGTGGGAGGGGACCGCTGTAAAGGAAGAGGAGCTGGAGCAGGAGTTGGAG
ACAGGCTGTCAGACTGAGGTCACCTCGGAGCGGCCCTTTAGCTGTGAAGTGTG
TGGCCGCACCTACAAGCATGCTGGCAGCCTTATCAATCACCGGCAGAGCCACC
AGACTGGCCA 2-10.PEP

ASAQPFLCCLCGMIFPGRTGYRRHLRQAHGASAMTEGSEEEEEGTAETASTHS
PPLQLSEAELLNQLQREVEALDGAGYGHICGCCGQTYDDLGSLERHHQSQSSSNRT
ENVPSHLEGAGDATEMVADHGFEGTVTSVSEEGGDIKSEEGVGGTVADSLCMQA
GESFLESHPRPFQCNQCGKTYRHGGSLVNHRKIHQTGDFICPVCSRCYPNLAAYR
NHLRNHPRCKGSEPQMGPISEAGGCSEPQNAAEAGQEQAVIGQLQEELKVEPLEEL
AGVKEEVWEGTAVKEEELEQELETGCQTEVTSERPFSCEVCGRT
YKHAGSLINHRQSHQT 2-32.SEQ

GGAAGCCAAGGGCACATCTCTATACCCCAGCCTGACTGCCCAGAGGAGGTGC
GGGCCTTCTCCTTCTACCTCTCCAATATTGGCCGCGACAGCCCTCAGGGCAGCT
TTGATTGCATCCAACAATATGTATCCAGCTATGGGGATGTACACCTGGACTGCC
TGGGCAGCATCCAGGACAAGGTCACGGTGTGTGCTACTGATGACTCCTACCAG
AAAGCACGACAGAGCATGGCACAGGCAGAGGAGGAGACTCGGAGCCGAAGT
GCCATCGTCATTAAGGCTGGAGGCCGATACATGGGGAAAAAGGTTCAGTTTCG
GAAGCCAGCGCCAGGGGCAGCTGATGCAGTACCCTCCCGGAAGCGTGCTACC
CCCATTAACCTGGCAAGTGCCATCAGAAAGAGCAGTGGGAGTGGAGCCAGCA
GTGTGGTACAGAGGCCCTTCCGAGATCGGGTGCTACACCTCCTGGCCCTGAGG
CCCTACAGGAAGGCTGAGCTGCTGCTGCGGTTGCAGAAGGATGGGTTGACAC
AGGCAGACAAGGACACCCTGGACAGCCTGCTGCAGCAGGTGGCCAGTGTGAA
CCCCAAGGATGGCACGTGCACGCTGCAGGACTGCATGTACAAAAGCCTGCAGA
AGGACTGGCCCGGCTACTCTGAGGGGACCGGCAGCTGCTGAAGCGCATGCT
CATGCGGAAGCTGTGTCAGCCACAGAATGCCACTACAGACTCCAGCCCGCCCC
GAGAGCATGGACGCTCTGCCTCACCCTCTCAGAAACGGCGTACAGACTTCATT
GACCCCCTGGCCAGCAAGAAGCCCCGGATCTCACATTTCACACAGCGAGCACA
ACCCACCCTCAATGGCAAACTGGGTGCCCCCAATGGCCATGAGACACTGCTGC

FIG. 15A

```
CTGTTCCAGGACCCACCCCATCAGACACCTTCAGCTCTAGCCATCTGCCCCCAC
GGCTGGAGCCCCCAAGGACCCACGACCCCCTAGCTGATGTCAGTAATGACCTA
GGTCACAGTACCCAGGACTACAAGCACCAGGAAGCCACCCCAGCTCCAGCACC
CCATTTTGGTCTTCCCCTGCTGACGGACTTTCCTCAGGGTGAGCAACCTATTAG
TTCCTCACACACCCACAGCCGACCCAAGAAGAAGTCCAAGAAGCACAAAGACA
AGGAGCGGCCCCCTGAAGAAAGGCCCCCCGCCCCACAGCCTGATGCACCTACT
GCCCCTGCACTACCGCCAGATGCCCCAGGTCTGAATGGAGCCTGTGACAATGA
ACCCACATCCTTGTCAGAGACCCCGG
```

2-32.PEP

```
GSQGHISIPQPDCPEEVRAFSFYLSNIGRDSPQGSFDCIQQYVSSYGDVHLDCLGSIQ
DKVTVCATDDSYQKARQSMAQAEEETRSRSAIVIKAGGRYMGKKVQFRKPAPGA
ADAVPSRKRATPINLASAIRKSSGSGASSVVQRPFRDRVLHLLALRPYRKAELLLRL
QKDGLTQADKDTLDSLLQQVASVNPKDGTCTLQDCMYKSLQKDWPGYSEGDRQL
LKRMLMRKLCQPQNATTDSSPPREHGRSASPSQKRRTDFIDPLASKKPRISHFTQR
AQPTLNGKLGAPNGHETLLPVPGPTPSDTFSSSHLPPRLEPPRTHDPLADVSNDLG
HSTQDYKHQEATPAPAPHFGLPLLTDFPQGEQPISSSHTHSRPKKKSKKHKDKER
PPEERPPAPQPDAPTAPALPPDAPGLNGACDNEPTSLSETP
```

10.SEQ

```
CGAGAACACACAGGCAAACCCACCACGAGTAGCTCAGAAGCATGTCGCTTCTG
TGGTTCCAGGAGTGGAACAGAGTTATCTGCTGTTGGCAGTGTTTGTTCTGATGC
AGATTGCCAGGAATACGCTAAGATAGCCTGTAGTAAGACGCATCCTTGTGGCC
ATCCATGCGGGGGTGTTAAAAACGAAGAGCACTGTCTGCCCTGTCTACACGGC
TGTGACAAAAGTGCCACAAGCCTGAAGCAAGACGCCGATGACATGTGCATGAT
ATGTTTCACCGAAGCGCTCTCGGCAGCACCAGCCATTCAGCTGGATTGTAGTCA
CATATTCCACTTACAGTGCTGTCGGCGAGTATTAGAAAATCGATGGCTTGGCCC
AAGGATAACATTTGGATTTATATCTTGTCCCATTTGCAAGAACAAAATTAATCAC
ATAGTACTAAAAGACCTACTTGATCCAATAAAAGAACTCTATGAGGATGTCAGA
AGAAAAGCCTTAATGAGATTGGAATATGAAGGTCTGCATAAGAGTGAAGCTAT
CACAACTCCTGGTGTGAGGTTTTATAATGACCCAGCTGGTTATGCAATGAATAG
ATATGCATATTATGTGTGCTACAAATGCAGAAAGGCATATTTTGGTGGTGAAGC
TCGCTGCGATGCTGAGGCTGGACGGGGAGATGATTATGATCCCAGAGAGCTCA
TTTGTGGTACCGAGAGCGTTTAGGTGAAACATATCATGCACATGTCATCGGCGT
CTTGCT
```

10.PEP

```
REHTGKPTTSSSEACRFCGSRSGTELSAVGSVCSDADCQEYAKIACSKTHPCGHPC
GGVKNEEHCLPCLHGCDKSATSLKQDADDMCMICFTEALSAAPAIQLDCSHIFHLQ
CCRRVLENRWLGPRITFGFISCPICKNKINHIVLKDLLDPIKELYEDVRRKALMRLE
YEGLHKSEAITTPGVRFYNDPAGYAMNRYAYYVCYKCRKAYFGGEARCDAEAGR
GDDYDPRELICGTESV.VKHIMHMSSASC
```

1-22.SEQ

```
ATGGCGGCTGGGACCCTGTACACGTATCCTGAAAACTGGAGGGCCTTCAAGGC
TCTCATCGCTGCTCAGTACAGCGGGGCTCAGGTCCGCGTGCTCTCCGCACCAC
```

FIG. 15B

```
CCCACTTCCATTTTTGGCCAAACCAACCGCACCCCTGAATTTCTCCGCAAATTTCC
TGCCGGCAAGGTCCCAGCATTTGAGGGTGATGATGGATTCTGTGTGTTTGAGA
GCAACGCCATTGCCTACTATGTGAGCAATGAGGAGCTGCGGGGAAGTACTCCA
GAGGCAGCAGCCCAGGTGGTGCAGTGGGTGAGCTTTGCTGATTCCGATATAGT
GCCCCCAGCCAGTACCTGGGTGTTCCCCACCTTGGGCATCATGCACCACAACA
AACAGGCCACTGAGAATGCAAAGGAGGAAGTGAGGCGAATTCTGGGGCTGCT
GGATGCTTACTTGAAGACGAGGACTTTTCTGGTGGGCGAACGAGTGACATTGG
CTGACATCACAGTTGTCTGCACCCTGTTGTGGCTCTATAAGCAGGTTCTAGAGC
CTTCTTTCCGCCAGGCCTTTCCCAATACCAACCGCTGGTTCCTCACCTGCATTAA
CCAGCCCCAGTT
```

1-22.PEP

```
MAAGTLYTYPENWRAFKALIAAQYSGAQVRVLSAPPHFHFGQTNRTPEFLRKFPAGKVPAF
EGDDGFCVFESNAIAYYVSNEELRGSTPEAAAQVVQWVSFADSDIVPPASTWVFPTLGIMH
HNKQATENAKEEVRRILGLLDAYLKTRTFLVGERVTLADITVVCTLLWLYKQVLEPSFRQAF
PNTNRWFLTCINQPQ
```

2-18.SEQ

```
AAAGCTTTAGAGGAGACCAAAGCCTATACAACCCAATCTCTAGCTAGTGTTGCT
TATCAAATAAATGCATTGGCCAACAATGTACTCCAGTTGCTGGATATCCAAGCC
TCTCAGCTTCGGAGAATGGAGTCTTCCATCAATCATATCTCACAGACTGTGG
ATATTCATAAGGAGAAAGTGGCACGAAGAGAGATTGGTATTTTGACAACAAATA
AGAATACATCAAGAACTCACCAAATAATAGCACCTGCGAATATGGAGCGCCCT
GTAAGGTATATTCGGAAACCTATCGATTACACAGTTCTGGATGATGTGGGCCA
TGGTGTCAAGCATGGAAATAACCAGCCTGCAAGAACTGGCACACTGTCGAGAA
CAAATCYTCCTAYTCAGAAACCGCCAAGTCCTCCCATGTCAGGCCGGGGAACA
CTGGGACGGAATACTCCTTATAAAACCCTGGAACCTGTTAAACCCCCACAGTTC
CTAATGACTATATGACCAGTCCTGCTAGGCTTGGAAGTCAGCATAGTCCAGGCA
GGACAGCATCTTTAAATCAGAGACCAAGGACACACAGTGGAAGTAGTGGAGGA
AGTGGAAGTCGAGAAAACAGTGGTAGCAGTAGTATTGGCATTCCCATTGCTGT
GCCTACACTTTCGCCACCCACTATTGGACCAGCAGCCCCGGGCTCAGCTCCTG
GTTTCCCAGTATGGCACAATGACCAGGCAGAC
```

2-18.PEP

```
KALEETKAYTTQSLASVAYQINALANNVLQLLDIQASQLRRMESSINHISQTVDIHK
EKVARREIGILTTNKNTSRTHQIIAPANMERPVRYIRKPIDYTVLDDVGHGVKHGN
NQPARTGTLSRTNXPXQKPPSPPMSGRGTLGRNTPYKTLEPVKPPQFLMTLPVLL
GLEVSIVQAGQHLIRDQGHTVEVVEEVEVEKTVVAVVLAFPLLCLHFRHPLLDQQP
RAQLLVSQYGTMTRQ
```

FIG. 15C 3-1.SEQ

CCGCCGCCTTTATTAGCTGAGCCATTACTTGAGAGGGATGAAGCGGGAGGAG
TGGGTGGCCCCGATGCCGGGCCGGCCATGCTTTACGGGCTTGTAGGTGATGG
AGAACTCGCCCAGGTAGTGGCCGATCATCTCGGGCTTGATCTCCACCTGGTTG
AAGGTCTTGCCGTTGTAGACGCCCACCATGCTGCCCACCATCTCGGGTAGGAT
GATCATGTCCCGCAGGTGCGTCTTCACCACTTCCGGCTTCTCCATGGGCGGCG
CCTCCTTCTTGGCCTTGCGCAGGCGCTTCAGCAGGGAGTGCTGCTTCCGCCGC
AGGCCCCGGTTCAGCCGCCGCCGCTGGCGCGCACTGTACAGCTGCATCAGCTG
CTCGTAGGACATGTCCAGCAGCTGGTCGAGATCCACGCCGCGGTAGGTGAAC
TTGCGGAAGGTCCGCTTCTTCTTCTGCTCTACTTCTGCCATCTTGCCGGCGGCC
GC 3-1.PEP

PPPLLAEPLLERDEAGGVGGPDAGPAMLYGLVGDGELAQVVADHLGLDLHLVE
GLAVVDAHHAAHHLG.DDHVPQVRLHHFRLLHGRRLLLGLAQALQQGVLLPPQA
PVQPPPLARTVQLHQLLVGHVQQLVEIHAAVGELAEGPLLLLLYFCHLAGGR 2-20.SEQ

GGGGATGCAGGCGTGGTCCTCCTCCAGGTCCTTCAGGCAGATCTCCAGGTGCA
GCTCGCCGGCGCCCGCGATGATGTGCTCTCCCGACTCCTCGATGATGCACTGC
ACCATGGGGTCGGACTTGGCCAGCCGCTTCAGCCCCTCCACCAGCTTGGGCAG
GTCAGCCGGGTTCTTGGCCTCCACGGCCACTCTGACAACAGGGCTGACGCTGA
ACTTCATCACCCGCATGTTGTGCGCGTGCTCGAAAGTGGTGATGGTGCCCGTC
TTCACCAGGAACTGGTCCACGCCCACGAGCCCACAATGTTCCCACAAGGCACA
TCCTCGATGGGCTCCACGTAtCGGGCCATCATCAAGATTGTTCTCTGGATTGGC
TTCAGGTAGAAGTCCTCCTCTTCCACGGGTTTTATTGGG 2-20.PEP

GDAGVVLLQVLQADLQVQLAGARDDVLSRLLDDALHHGVGLGQPLQPLHQLGQ
VSRVLGLHGHSDNRADAELHHPHVVRVLESGDGARLHQELVHAHEPTMFPQGT
SSMGSTYRAIIKIVLWIGFR.KSSSSTGFIG

FIG. 15D ns of PKC-theta along with fyn and its fragments are specifically exemplified. Additional embodiments wherein fragments of PKC-theta containing the C2 region of PKC-theta interact with particular cognates which contain SH3 regions are also exemplified.

METHODS TO IDENTIFY IMMUNOMODULATORS USING COGNATE INTERACTION OF PKC-THETA

RELATION TO OTHER APPLICATIONS

This application is a continuation-in-part of Ser. No. 08/594,447 filed Jan. 31, 1996, U.S. Pat. No. 5,776,716, which is a continuation-in-part of U.S. Ser. No. 08/541,964, filed Oct. 10, 1995, U.S. Pat. No. 5,783,405, and U.S. Ser. Nos. 08/473,089, 08/477,346, and 08/487,072, all filed Jun. 7, 1995 and all of which claim priority from PCT Application PCT/US95/01210 filed Jan. 31,1995, WO 95/21252 published Aug. 10, 1995. The present application is also a continuation-in-part of U.S. Ser. No. 08/190,802 filed Feb. 1, 1994, now U.S Pat. No. 5,519,003. The contents of all of the foregoing applications are incorporated herein by reference.

TECHNICAL FIELD

The field of this invention is methods for identifying pharmaceutical agents for use in modulating activities of the immune system and methods of using agents identified in the disclosed methods.

BACKGROUND ART

PCT Application WO 95/21252, discloses and claims peptide compositions which alter the activity of a signal-generating protein with respect to its cognate protein wherein the cognate protein contains at least one WD-40 region which putatively interacts with the signal-generating protein. The peptide compositions mimic the WD-40 regions, thus competing with the interaction of the cognate with the signal-generating protein. This competition results either in inhibiting the signal-generation or activating it.

One specifically exemplified signal-generating protein is protein kinase C (PKC); the illustrated cognate receptor for activated kinase C (RACK), in this case specific for βPKC, was designated RACK1. The gene encoding RACK1 was cloned and sequenced, showing that RACK1 contains the requisite WD-40 regions.

The above PCT application and U.S. Ser. Nos. 08/473, 089, 08/477,346, and 08/487,072 further describe methods to identify additional pairs of signal-generating proteins and their cognates and methods for recognizing WD-40 sequences in the cognates. These applications also note that such interactions can be used as a system to identify additional molecules that bind the signal-generating protein by measuring the effect of candidate binding molecules on the interaction between the signal-generating protein and either its cognate per se or the polypeptide compositions that mimic the WD-40 regions of the cognate.

In U.S. Ser. No. 08/541,964, several specific peptides were identified that bind either to the signal-generating protein or to the cognate protein in a signal-affecting manner. The use of the signal-generating protein/cognate system to assay for modulators of signal transduction in assays which are independent of the purity of these participants was described. The PKC enzyme system was illustrated as a specific embodiment. In addition, peptides which reside on the signal-generating protein, as well as those which reside on the cognate or mimics thereof, were described as being useful to modulate the signal-generating interactions and biological activities which are mediated by the signal-generating interactions.

In U.S. Ser. No. 08/594,447, experiments that demonstrated the identity of a cognate protein for PKC-theta as the fyn protein were described. Since it is well established that fyn is involved in mediation of T-cell responses, it is apparent that disruption of the interaction of PKC-theta with its fyn cognate mediates the immune response. It is also apparent that PKC-theta is a mediator of the immune response. Substances which can be shown to disrupt the interaction between PKC-theta and its cognate fyn, or, as described hereinbelow, to influence the interaction of PKC-theta with any cognate also have immunomodulating activity. The identification of fyn as a PKC-theta cognate, and the consequences of interfering with this association, demonstrate that PKC-theta is a significant signaling protein involved in the immune response.

DISCLOSURE OF THE INVENTION

The present invention is directed to an efficient assay system to identify modulators of the immune system. The assay system measures the effect of candidate substances on the interaction between a signaling protein—in this case PKC-theta, or a fragment thereof, with its cognate. The cognate comprises the relevant portion of a molecule which binds to PKC-theta. Because the method takes advantage of inherent biological specificity, it can be conducted on impure preparations of the participants in the signal pathway—i.e., the above-mentioned signal-generating protein PKC-theta and its cognate receptor. The assay is conducted by assessing the interaction between the signal-generating protein and its cognate either by measuring binding directly or by measuring a physiological or metabolic effect. The measurement is made in the presence and in the absence of a candidate substance. Successful candidates which agonize the signal effect an increase in a metabolic or physiological output; antagonists effect a decrease. Both antagonists and agonists compete for binding between cognate and signal-generating protein.

Among successful candidates will be peptides, which mimic regions on either the signal-generating protein or the cognate, as well as nonpeptide small molecules. Due to their ease of identification, successful peptide candidates are particularly useful as participants representing the signal protein or cognate in the screening assays, in particular where binding is detected. The assay methods enable sophisticated screening of candidates. The results and uses of these methods can be combined with other assay-independent techniques for efficiently selecting leads.

The methods described herein may involve peptides derived from the cognate or signalgenerating protein. By "derived from" is meant that such peptides are either found in the cognate or signal-generating protein, or are modified by a limited number of conservative changes. Preferably the conservative changes represent less than about 20%, more preferably less than about 10%, and most preferably less than about 5% of the residues in the identified native sequence. One way to identify a suitable peptide is to compare sequences among species as is described in Example 4.

The invention is also directed to methods to screen libraries of candidate substances using the above-described methods and to peptides representative of sites on the signal-generating protein and cognate which are themselves useful in these assays as well as in other applications involving the relevant interaction.

The present invention is also directed to specific embodiments in which the above disclosed methods are employed using PKC-theta protein, and its fragments along with the cognates of PKC-theta. The fyn protein and certain fragments thereof were found to bind to PKC-theta. Utilizing this interaction and that of PKC-theta and its fragments with other cognates, the present invention provides methods to identify immunomodulators by detecting modulators of biological and pathological processes which are mediated by PKC-theta/cognate interaction. Such substances are useful in modulating an activity of the immune system, particularly the activity and differentiation of T-cells.

The present invention is thus based on using the interaction of PKC-theta with its cognates as an index to substances that modulate activities of the immune system. In the Examples, evidence is presented that the fyn protein binds to PKC-theta. This observation is important because no binding partners of PKC-theta were known prior to applicants' invention. By contrast, fyn had previously been found to be associated with several T-cell receptor affiliated proteins, including CD3 zeta chain, ZAP-70 and Grb-2. The identified fyn/PKC-theta interaction of the present invention can be used as a basis for making and identifying agents which can modulate immune responses. Competitive assays using PKC-theta and the fyn peptide, or a PKC-theta or fyn equivalent, can be used to identify compounds which block fyn/PKC-theta interaction. A PKC-theta or fyn "equivalent" represents a peptide that can mimic the interactive binding activity of PKC-theta or fyn which is derived from the amino acid sequences of the appropriate binding regions. In addition, surrogate cognates can be used which may have no structural relationship to the fyn protein, but which bind PKC-theta in a manner similar to that displayed by fyn. Additionally, peptide and protein modeling techniques can be used to study the specific interactions of the cognate partners with PKC-theta to rationally design or rationally select agents for testing. Successful agents can be used as therapeutics to inhibit or otherwise modulate immune responses.

BRIEF DESCRIPTION OF THE DRAWINGS

FIG. 9 (SEQ ID NO:1) shows a detailed map of sequence motifs present in fyn, including the WD40 repeats, smaller RACK1 homologies, and the most conserved consensus PKC phosphorylation site.

FIG. 15 shows the nucleotide sequences and encoded amino acid 2-10 (SEQ ID NO:2 and SEQ ID NO:3); 2-32 (SEQ ID NO:4 and SEQ ID NO:5); 10 (SEQ ID NO:6 and SEQ ID NO:7); 1-22 (SEQ ID NO:8 and SEQ ID NO:9); 2-18 (SEQ ID NO:10 and SEQ ID NO: 11); 2-20 (SEQ ID NO:14 and SEQ ID NO:25); and 3-1 (SEQ ID NO:12 and SEQ ID NO:13).

MODES OF CARRYING OUT THE INVENTION

General Background

PKCs represent a family of signal-generating isoenzymes, at least several of which are present in most cell types. Upon activation by a suitable agent, typically phosphatidylserine (PS) and diacylglycerol (DAG), and in some cases calcium ion, a PKC is translocated subcellularly, generally from the soluble fraction to another location in the cell that is associated with the particulate fraction. Each isoenzyme in this family apparently has one or more cognates (or RACKs) which are anchoring proteins at the appropriate locations associated with the physiological or metabolic effect of the activation of each particular isoenzyme. Thus, for example, one or a subset of PKCs contained in cardiac myocytes, when activated, results in a slowing of the contraction rate. One or a subset of PKCs contained in Xenopus oocytes, when activated, effect maturation of the egg. One or a subset of PKCs, when inhibited at the catalytic site, blocks T-lymphocyte activation. See, Birdchall et al. *J Pharm. Expt'l Ther* (1994) 268:922. The interaction of a particular PKC isoenzyme with its cognate RACK is required for the metabolic or physiological effect; therefore interference with this interaction will modulate that effect. Alternatively, the effect of the modulation may be agonistic if the interaction of the modulator promotes a conformational change in the signal generating partner corresponding to that normally occurring only upon the concurrent binding of activators (e.g., PS or DAG) and cognate protein, or otherwise results in signal activation.

Figure 1:
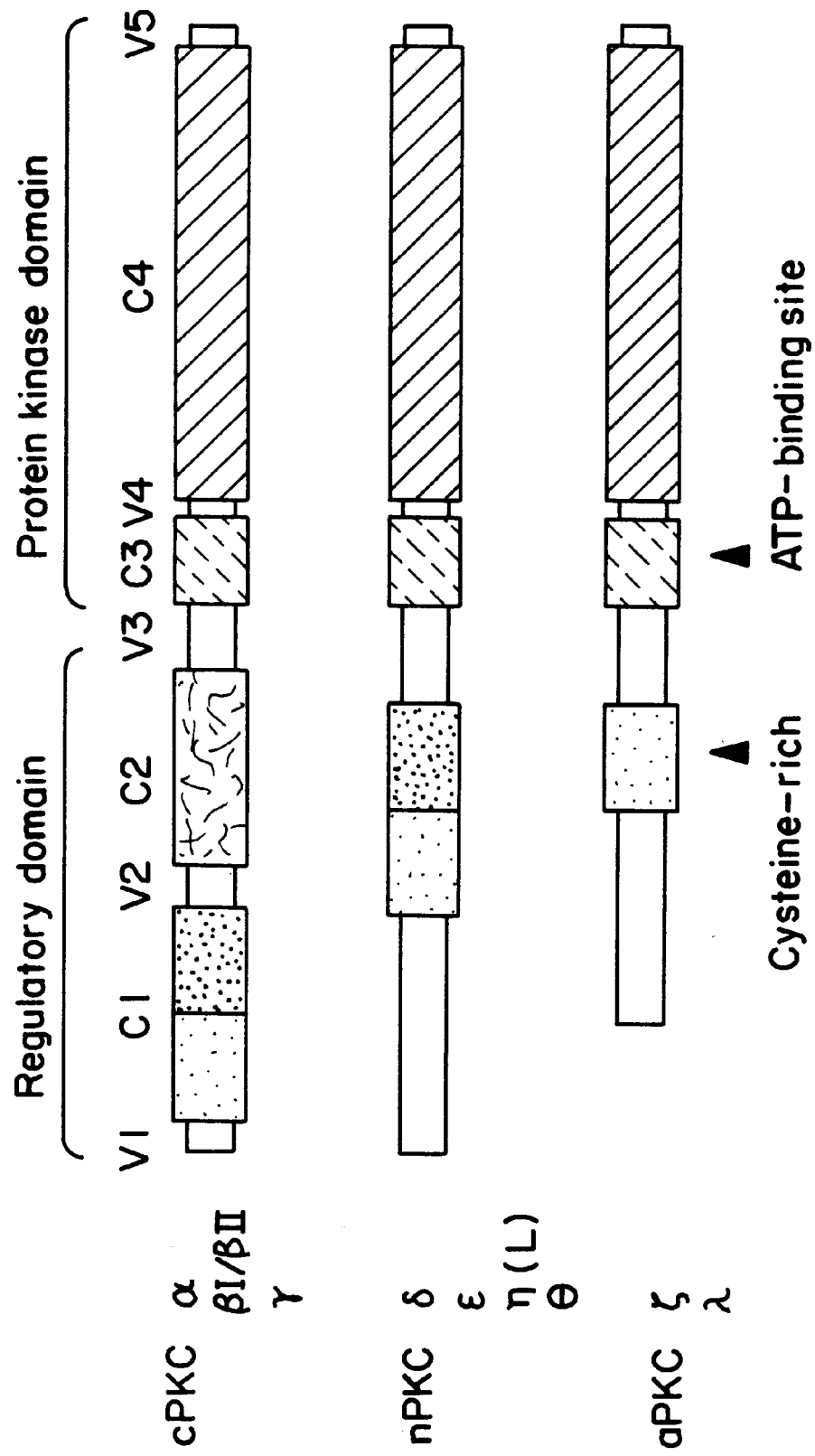
FIG. 1 shows, diagrammatically, the known general primary sequence and domains of various PKC isoenzyme families.

The known PKC isoenzymes can be divided into three major groups as shown in FIG. 1. All of the isoenzymes, regardless of group, contain a protein kinase domain represented by two constant (C) and two variable (V) regions. The regions which are responsible for the enzymatic activity are highly homologous or constant; the C4 region toward the carboxy terminus is thought to contain the catalytic site; the C3 regions upstream are responsible for binding ATP.

Upstream of the protein kinase domain in each case is a regulatory domain. All of the three families, the conventional (cPKC), the novel (nPKC) and atypical (aPKC) contain variable regions at the N-terminus designated VI, and constant regions immediately downstream marked C1. The C1 regions are thought to be involved in activation by phosphatidylserine, diacylglycerol, or pharmacological mimics such as phorbol esters. The C2 region is found only in the cPKC family and is thought to be the site for activation by calcium. However, the picture may not be quite so simple as C1 regions may also be involved in calcium binding, and the atypical class respond poorly to agents such as phorbol esters.

Nevertheless, it now appears clear that sequences within the regions shown as the regulatory domain are responsible for the interaction of the particular PKC with its cognate RACK. They may also contain a RACK-mimicking region, called a pseudo-RACK site, that prevents binding of PKC to its RACK when the PKC has not been activated. This situation is analogous to the pseudosubstrate sequence which is located elsewhere in the primary sequence and blocks the catalytic site prior to activation of the PKC. It is shown hereinbelow that the relevant regions are specific for the particular isoenzyme involved in a designated signal-generation event.

In the parent applications herein, published as PCT WO 95/21252, the cognate RACK1 protein which interacts with PKC-beta (a member of the cPKC family) was cloned and the WD-40 regions putatively responsible for binding to PKC-beta were identified through structural analogy. One of these WD-40 peptides was found to induce the kinase activity of PKC in the absence of PKC activators; both this peptide and another representing a WD-40 region rendered the PKC-beta susceptible to proteolysis, a characteristic of activated PKC forms. All of these peptides were also shown to inhibit the binding of PKC-beta to RACK1. In principle, the WD-40 regions of the appropriate RACK can serve as antagonists or agonists of the signal generation associated with the corresponding PKC. As described, an assay which shows the effects of members of a library of candidate modulators on interaction between the relevant PKC and its cognate or the relevant PKC and a WD-40 domain derived from said cognate can be used as a screening assay to identify modulators of this signal pathway.

In the illustrative work described below, modulation of signal generation can be achieved by supplying, to a reaction mixture containing an appropriate PKC, either WD-40 peptides derived from the relevant RACK or pseudo-RACK peptides from the PKC regulatory domain which themselves mimic the RACK's binding domains, or a surrogate cognate and examining the effect of these peptides on binding or signal generation. Substances that interact—i.e., behave as cognates—will bind PKC and/or alter its signal generation. PKC or cognate-binding peptides derived from PKC can also be used as assay reagents in combination with the appropriate cognate to screen for modulators of the signal-generating pathway by virtue of the ability of the successful candidate to affect the binding of the cognate protein to the signal-generating protein. In general, systems which employ a PKC/cognate combination whose interaction can be observed can be used to screen for substances that affect this interaction. Thus, the interaction is observed in the presence of a candidate and in its absence and the difference in the interaction under these two conditions reflects the ability of the candidate to modulate this interaction.

A particularly important signal-generating protein/cognate system is described hereinbelow. The signaling associated with PKC-theta is particularly significant in modulating the immune system, particularly T-cell responses. Therefore, substances that modulate the interaction between PKC-theta and its cognate are also modulators of the immune response, and thus can be used in contexts where modification of an immune response is desirable, such as in the treatment of allergies and asthma, preventing allograft rejection, and in autoimmune diseases. Described below are assay systems which employ PKC-theta or a fragment thereof wherein the cognate is that normally present in a host cell, is the fyn protein or a relevant fragment thereof, or a surrogate cognate defined according to the methods of the invention. As used herein, the terms "peptide" and "protein" will be used interchangeably without regard to size. It will be apparent in some cases which is intended according to conventional terminology; in others, both possibilities may be included. Applicants draw no arbitrary dividing line between peptides and proteins in terms of length of amino acid sequence.

Thus, in summary, various possible counterpart interactions can be tested; in no case are purified components required:

| Component 1 | Component 2 |
| --- | --- |
| Signal-generating protein (e.g. PKC) | Endogenous cognate protein |
| Signal-generating protein (e.g. PKC) | WD-40 region of e.g. a RACK |
| Signal-generating protein (e.g. PKC) | Pseudo-RACK region of, e.g., PKC |
| Signal-generating protein (e.g. PKC) | Surrogate cognate |
| Cognate-binding region of, e.g., PKC | Cognate protein |
| Cognate-binding region of, e.g., PKC | WD-40 region of, e.g., RACK |
| Cognate-binding region of, e.g., PKC | Pseudo-RACK region of, e.g., PKC |
| Cognate-binding region of, e.g., PKC | Surrogate cognate |

In the foregoing table, any assay method that detects the interaction appropriate to the components can be used. If the interaction is intracellular, certain physiological effects on the cell can be measured. If the interaction is in vitro, direct measurement of binding of the cognate components to the signal-generating protein is probably most appropriate.

In general, the present invention is directed to screening methods to identify modulators of particular signal pathways. Each assay will involve a cognate that binds sufficiently and specifically to a catalytically active signal-generating protein, via a noncatalytic site, to permit assay in impure preparations. The interaction of these two components is observed in the presence and absence of a candidate modulator. Depending on the assay system chosen, the interaction and its modification can be observed in a variety of ways, including intracellular binding assays affecting an observable parameter; either a physiological readout, such as change in subcellular distribution, or an artificial construct, such as transcription of a reporter gene, can be used. In no case, however, are purified reagents required, although it may be convenient in some cases, for example, to utilize the peptides identified as illustrated below which represent regions of the signal-generating protein (illustrated by PKC-theta) or its cognate binding protein (represented by the fyn) that are responsible for interaction.

It will be noted that the relevant endogenous PKC and the relevant endogenous cognate can be used in observing the effects of candidate substances—e.g., the ability of the candidate to alter intracellular translocation patterns upon activation of the signal-generating protein. Alternatively, surrogate cognate proteins can be used, such as those representing a WD40 region of a RACK or cognates identified using the approach described below by virtue of their ability to bind to the relevant PKC. If a surrogate is used in an in vitro system, generally binding is the measurable interaction. As used in the present application, the term "cognate" is applied to a substance that binds sufficiently and specifically to a catalytically active signal-generating protein via a noncatalytic site, as described above. "Cognate" therefore refers both to the endogenous cognate protein (or the relevant fragment) or equivalents derived from these and to a surrogate substance which shares the above-mentioned property. Although it is required that the cognate bind to a noncatalytic site, the cognate may, in addition, be a substrate for catalysis by the signal-generating protein.

As further described below, the peptides which can be substituted for one or the other component in the assay method are themselves identifiable through conduct of the assay. Thus, the ability of a compound to affect the interaction of the cognate protein and the signal-generating protein will identify it as a useful component of the assay, as well as a modulator of the signal pathway per se. Once the appropriate components are identified, the individual labeled components could be used to assess the level of binding. The labeled component may represent a region of the signal-generating peptide measured against a composition containing the cognate protein or, conversely, a component representing a portion of the cognate protein measured against the composition containing the signal-generating protein. These compositions may be whole cells or cell-free extracts or partially purified extracts.

It will be apparent that when a nonendogenous substance is chosen as one component of the assay, the screening tests are preferably performed by measuring only binding per se.

Alternatively, both the signal-generating protein and the cognate protein may be contained in a crude preparation and the method for assessing their interaction may include measuring localization of the signal-generating protein within the preparation per se or measuring a metabolic effect of the interaction, such as, for example, maturation of Xenopus oocytes or effect on the contraction rate of cardiac myocytes. The particular method of assessing the interaction will, of course, be appropriate to the partners in the interaction, and can readily be ascertained by taking advantage of the specificity of the signal pathways and their components as illustrated below.

In addition, the "two-hybrid" system may be used to effect interaction between a PKC or a fragment thereof and its cognate, and the effect of a candidate on this interaction can be observed. The "two-hybrid" system is described in U.S. Pat. No. 5,283,173, incorporated herein by reference. Briefly, as applied to the present invention, a recombinant host, typically yeast, is transformed with two expression systems each encoding a fusion protein. One fusion protein contains a portion of a transcription-activating factor fused to a PKC or cognate-binding fragment thereof, the other fusion protein contains the complementary portion of the transcription-activating portion fused to the cognate. Typically, the transcription-activating factor is an activator for RNA polymerase, and one portion represents the DNA-binding portion, the other the activator for the polymerase. When the cognate and PKC bind, the two portions of the transcription factor are brought into sufficient proximity that they are able to perform the function of activating transcription. The "two-hybrid" assay thus, also, will include a reporter expression system which is activated by the completed transcription factor to produce a reporter protein, such as β-galactosidase or chloramphenicol acetyl transferase. As defined herein, "two-hybrid assay" refers to this general approach.

For convenience, the assays to identify modulating candidate compounds will sometimes be described as measuring the effect of the candidate on the "binding" of the counterpart components in the reaction mixture. It will be understood that in the instance where both the cognate protein and the signal-generating protein are the active components of the composition participating in the assay, binding may be measured not only directly, but also by the resulting metabolic or physiological effects.

The fyn/PKC-theta Interaction

It has been shown hereinbelow that the signal generation mediated by PKC-theta is significant in regulating the activation of T-cells. Thus, modification of PKC-theta mediated signaling will result in modification of the immune response. The substances that can be identified as modulating this signaling pathway are thus useful as immunomodulating agents in preventing allergic reactions or reducing their severity, or in treating asthma, in ameliorating the effects of autoimmune disease, and in reducing the risk of rejection of transplants. It has also been demonstrated below that PKC-theta interacts endogenously with the fyn protein which serves as at least one of its endogenous cognates. Thus, the PKC-theta/fyn interaction per se can be used as an assay system for identifying candidate substances that will behave as immunomodulators.

In one form of the assay, the PKC-theta signaling protein and the fyn cognate occur endogenously in a test cell, and the effect of the candidate on the PKC signaling function can be measured directly. As illustrated below, translocation of PKC-theta occurs on activation and thus binds to the endogenous cognate protein. The effect of a candidate substance on this translocation can be directly determined as a measure of its affect on interaction of PKC-theta with its cognate.

Alternatively, assays can be constructed in vitro or in vivo involving PKC-theta and fyn directly. Specifically, to identify an agent which modulates fyn/PKC-theta interaction, the fyn protein, a fragment of the fyn protein containing the domain which binds to PKC-theta or a fusion protein containing the domain of the fyn protein which binds to PKC-theta, is provided in the same environment with PKC-theta, a fragment of PKC-theta containing the fyn binding domain or a fusion protein containing the fyn binding domain, wherein the environment is such that ordinarily the signal-generating protein (PKC-theta) and the cognate (fyn) would interact. The environment is provided in the presence and in the absence of a substance to be tested. Differences in interaction between the signaling protein and the cognate in the presence and absence of the substance to be tested are compared; agents that block or otherwise affect the interaction can be identified by determining the differences in interaction between these two circumstances.

The fyn protein represents a family of splicing variants, and by "fyn" is meant any of these spliced variants and peptides which bind PKC-theta which are derived from them.

As used herein, an agent is said to block or decrease fyn/PKC-theta binding when the presence of the agent prevents or reduces the amount of association of the PKC-theta peptide with the fyn peptide. One class of agents will reduce or block the association by binding to the PKC-theta peptide while another class of agents will reduce or block the association by binding to the fyn peptide. Two examples of the first class of agent include antibodies which bind to the PKC-theta peptide and block the fyn binding site on PKC-theta and peptides which contain the PKC-theta binding site found on fyn. Two examples of the second class of agents include antibodies which bind to the fyn peptide and block the PKC-theta binding site on fyn and peptides which contain the fyn binding site found on PKC-theta. Other types of interaction may also be envisioned.

The fyn peptide used in the present method can either be the entire fyn protein whose amino acid sequence is known in the art, a fragment of the fyn peptide which binds the PKC-theta, or a small region thereof that retains the binding activity or a protein which contains the PKC-theta binding site of fyn, such as a fusion protein containing the appropriate fyn sequence. Alternatively, the fyn peptide can contain more than one copies of the fyn sequence, such as in a palindromic or tandem repeat. A cell or virus expressing the fyn peptide can also be used.

As an alternative to compounds containing the fyn sequence, agents identified in the present method can be substituted for the fyn peptide. For example, an agent which is found to block fyn/PKC-theta binding by binding to PKC-theta can be used in place of the fyn peptide.

The PKC-theta peptide used in the present method can be any member of the PKC-theta family of proteins so long as the member binds the fyn peptide. As used herein, a PKC-theta family member refers to proteins currently known in the art which are members of the PKC-theta family of proteins (for a review see Baier et al *J Biol Chem* (1993) 268(7):4997–5004 and Baier et al., *Eur J Biochem* (1995) 225(1): 195–203). These include PKC-theta isolated from organisms such as humans, mice, etc., as well as the various splice forms of PKC-theta found in each organism. The PKC-theta family member can be used in its entirety or a fragment of the PKC-theta protein which contains the fyn binding site can be used. The preferred fragment will be derived from the V1 region of PKC-theta; the strongly isozyme-specific regions V3 or V5 also can be used. Alternatively, a cell or virus expressing the PKC-theta, or PKC-theta fragment, can be used.

The fyn and PKC-theta peptides used in the present invention can be used in a variety of forms. The peptides can be used in a highly purified form, free of naturally occurring contaminants. Alternatively, a crude preparation containing a mixture of cellular components as well as the fyn and PKC-theta peptides can be used. Further, the fyn or PKC-theta peptides can be isolated from cells which naturally express these peptides, from cells which have been altered, using recombinant methods, to express these peptides, or can be synthesized using standard peptide synthesis methods. So long as the association of the PKC-theta peptide with the agent to be tested and/or the fyn peptide can be identified in the sample, the fyn and PKC-theta peptides are in a suitable form for use in the above described assay.

The fyn and/or PKC-theta peptides can additionally be modified to contain a detectable label or signal generation system to facilitate detection. Methods for attaching agents such as fluorescence tags or fluorescence polarization and secondary labeling agents such as biotin, are well known in the art.

A variety of art-known methods can be adapted and employed to detect whether an agent blocks or reduces the interaction of the fyn peptide with the PKC-theta peptide. Such methods include, but are not limited to, assays which employ a solid support, assays in solution phase, assays performed in a gel-type media, and assays which use a combination of these environments. An example of a solid phase assay would be one in which one or both of the fyn and PKC-theta peptides are immobilized on a solid support and is incubated in a solution phase with the agent to be tested and the other peptide of the fyn/PKC-theta pair. A secondary detection means, such as an antibody, is then used to determine the amount of the second peptide which binds to the immobilized peptide. Alternatively, the second peptide of the fyn/PKC-theta pair can be detectably labeled and its binding to the immobilized first peptide is directly assessed. One format which is preferably suitable for a solid phase based assay is immobilization of one of the peptides in a 96-well micro-titer plate. Such titer plates provide an efficient assay format for rapidly processing multiple samples.

Alternatively, both peptides of the fyn/PKC-theta binding pair can be in solution. After mixing, the binding of the fyn peptide to the PKC-theta peptide can be detected using a variety of methods, for example detecting mobility shifts using electrophoretic means. One skilled in the art can readily appreciate how numerous assay-type formats which are known in the art for use in competitive assays can be modified to use the fyn/PKC-theta peptide pair.

As described above, the binding of PKC-theta and fyn or a fyn substitute can be detected using the two-hybrid assay system. The "fyn substitute" can be any alternative peptide or other molecule which is found in the assays of the invention to bind to PKC-theta so as to interfere with the action of PKC-theta with fyn or other endogenous cognates. Thus, the discussion herein is not to be considered limited to PKC-theta/fyn interaction per se, but includes interactions of PKC-theta with any cognate.

Direct binding to the PKC-theta peptide or the fyn peptide can, but need not, be used as first step in identifying agents which block fyn/PKC-theta interaction. In such methods, agents are first screened for the ability to bind to the PKC-theta or fyn peptides. Agents which bind to either of the two peptides are then screened for the ability to block fyn/PKC-theta interaction, or for the ability to modulate a function of the immune system.

Agents which are assayed in the above methods can be randomly selected or rationally selected or designed. As used herein, an agent is said to be randomly selected when the agent is chosen randomly without considering the specific sequences involved in the association of the fyn peptide with the PKC-theta peptide. An example of randomly selected agents is the use of a chemical library or a peptide combinatorial library.

As used herein, an agent is said to be rationally selected or designed when the agent is chosen on a nonrandom basis which takes into account the sequence of the target site and/or its conformation in connection with the agent's action. As described above, two sites of actions for agents of the present invention are the fyn peptide and the PKC-theta peptide. Agents can be rationally selected or rationally designed by utilizing the peptide sequences which make up the contact sites of the fyn/PKC-theta pair. For example, a rationally selected peptide agent can be a peptide whose amino acid sequence is identical to the fyn contact site found on PKC-theta. Such an agent will reduce or block the association of fyn with PKC-theta by binding to fyn.

The agents of the present invention can be peptides, small molecules, vitamin derivatives, as well as carbohydrates. A skilled artisan can readily recognize that there is no limit as to the structural nature of the agents of the present invention or those used in the present assay methods.

As provided above, one class of agents of the present invention is that of peptide agents whose amino acid sequences are chosen based on the amino acid sequence of fyn and in particular the PKC-theta contact site found on fyn, while a second class of agents is that of peptide agents whose amino acid sequences are chosen based on the amino acid sequence of PKC-theta and in particular the fyn contact site found on PKC-theta. The fyn contact site on PKC-theta and the PKC-theta contact site on fyn can readily be determined using art-known methodologies. For example, tryptic digestion of the PKC-theta protein can be performed and the various fragments of PKC-theta can be tested for their ability to bind the fyn peptide. Alternatively, a modification of a bind and chew assay can be used in which the fyn and PKC-theta peptides are allowed to interact and the interactive pair is subject to protein digestion. Regions of the PKC-theta peptide which are contacted by the fyn peptide will be protected from digestion and can be later characterized to determine the amino acid sequence which is bound and protected. Alternative assays which detect binding of the various fragments can also be used.

All of the peptide agents of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1–6 C. In all of the peptides of the invention, one or more amide linkages (—CO—NH—) may optionally be replaced with another linkage which is an isostere such as —$CH_2NH$—, —$CH_2S$—, —$CH_2CH_2$—, —CH=CH— (cis and trans), —$COCH_2$—, —$CH(OH)CH_2$— and —$CH_2SO$—. This replacement can be made by methods known in the art. Alternative peptide linking moieties can also be used to decrease the rate of degradation of peptide based agents. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Spatola, A. F., et al., *Life Sci* (1986) 38:1243–1249 (—$CH_2$—S); Hann, M. M., *J Chem Soc Perkin Trans I* (1982) 307–314 (1982) (—CH—CH—, cis and trans); Almquist, R. G., et al., *J Med Chem* (1980) 23:1392–1398 (—$COCH_2$—); Jennings-White, C., et al., *Tetrahedron Lett* (1982) 23:2533 (—$COCH_2$—); Holladay, M. W., et al., *Tetrahedron Lett* (1983) 24:4401–4404 (—C(OH)$CH_2$—); and Hruby, V. J., *Life Sci* (1982) 31:189–199 (—$CH_2$—S—).

In addition to analogs which contain isosteres in place of peptide linkages, the peptides or proteins of the invention include peptide mimetics in general, such as those described by Olson, G. L. et al. *J Med Chem* (1993) 36:3039–3049 and retro-inverso type peptides as described by Chorev, M. et al. *Science* (1979) 204:1210–1212; and Pallai, P. V. et al., *Int J Pept Protein Res* (1983) 21:84–92.

Another class of agents of the present invention is that of antibodies immunoreactive with critical positions of the fyn protein or with the PKC-theta protein. Since the target for action of the agents of the present invention is within a cell (cell signaling involved in fyn/PKC-theta interaction), antibody agents are most useful in immunodiagnostic methods and find use as substitutes for either the fyn or PKC-theta peptides in the present methods. However, using currently available recombinant technologies, antibodies can be produced intracellularly, and thus can participate in intracellular forms of the assays as well.

Antibody agents are obtained by immunization of suitable mammalian subjects with peptides, containing as antigenic regions, those portions of the fyn or PKC-theta proteins which are intended to be targeted by the antibodies. Critical regions include, but are not limited to, the contact sites involved in the association of fyn with PKC-theta and sites which provide steric interference with the contact sites upon binding.

Antibody agents are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at the amino or carboxy terminus with a cysteine residue or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. (See Harlow: Antibodies Cold Spring Harbor Press NY 1989) The immortalized cell lines secreting the desired antibodies are screened by immunoassay in which the antigen is the peptide hapten or is the PKC-theta or fyn peptide. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin. The antibodies or fragments may also be produced, using current technology, by recombinant means. Regions that bind specifically to the desired regions of receptor can also be produced in the context of chimeras with multiple species origin.

It is, of course, unnecessary to conduct initial production of the antibodies through immunization and isolation of immortalized cells that secrete monoclonals. Techniques are available for cloning immunoglobulin genes so that production can be effected through de novo recombinant synthesis.

Regardless of whether the genes originate in immortalized B cells or result from cloning efforts, manipulation of the genes permits redesign of the immunoglobulins, including production of single-chain immunoglobulins such as $F_v$ fragments.

Uses for Substances which Modulate Interaction of Cognate with PKC-theta

Interaction between PKC-theta and its cognate has been implicated in modulating a variety of biological responses. According to the present invention, this interaction results in modulation of the immune system, particularly those activities involving T-cell activity. Therefore, substances which affect PKC-theta interaction with its cognate can be used to modulate activities of the immune system.

Specifically, immune system activity, such as T-cell mediated responses, can be modulated by administering to a subject a substance which affects the interaction of an appropriate cognate with PKC-theta. The subject can be any vertebrate in need of modulation of immune activity. These substances are particularly useful in treating human subjects.

Immune system activity refers to the wide variety of cellular events in which cells of the immune system participate. Examples of situations where it is desirable to modulate such activity include, but are not limited to, transplant surgery, autoimmune disorders, and response to allergens. In each of these situations, it is desirable selectively to reduce T-cell responsiveness.

A substance modulates an immune system activity when it reduces the severity of a pathological condition mediated by the immune system, or when it affects either positively or negatively the normal immune activity of the subject. For example, an agent is said to modulate the immune system activity involved in graft rejection when it reduces the rate of onset of graft rejection or reduces the severity of graft rejection. Other effects on the immune system can be determined more precisely. For example, the resultant effect may be to diminish the production of cytokines such as IL-4 or IL-5 as illustrated below, preferably with no effect on γ-IFN production.

Administration of Agents which Modulate Immune System Activity

The agents of the present invention can be provided alone, in combination with another agent that modulates a function of the immune system, or in combination with drugs having additional physiological effects. For example, a substance of the present invention that reduces T-cell activity can be administered in combination with other immunosuppressive agents, and/or with another substance so identified. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route, or by inhalation. The dosage administered will be dependent upon the age, health, and weight of the recipient, kind of concurrent treatment, if any, frequency of treatment, and the nature of the effect desired.

The present invention further provides compositions containing one or more agents of the present invention. While individual needs vary, determination of optimal ranges of effective amounts of each component is within the skill of the art. Typical dosages are in the range of 0.01–50 mg/kg body weight. Preferred dosages are in the range of 0.1–10 mg/kg; most preferably 0.1–1 mg/kg.

In addition to the pharmacologically active agent, a composition comprising an agent of the present invention may contain suitable pharmaceutically acceptable carriers such as excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

Suitable formulations for administration by inhalation include metered dose inhalers and dry powder devices. For nasal absorption aqueous and nonaqueous suspensions or dry powders may be used.

Methods for Targeting

The effective affinity of the substances of the present invention can be increased by covalently linking the agent to a second agent which also binds either PKC-theta or its cognate. Such a second agent will bind to another site on either the cognate or PKC-theta molecule and bring the first agent into close proximity to the target site, augmenting the overall avidity. Such second agents can be, but are not limited to, antibody and peptide agents. The second agent can be covalently attached to the first agent using art-known methods. Methods which employ linkers are particularly well suited for this use.

Without further description, it is believed that one of ordinary skill in the art can, using the preceding description and the following illustrative examples, practice the claimed invention. The following working examples illustrate preferred embodiments of the present invention, and are not to be construed as limiting.

EXAMPLE 1

Specificity of Negative Chronotropy for εPKC Translocation

Neonatal rat cardiac myocytes were used in this assay. These cells, when prepared in culture, exhibit contractions at approximately the rate of 40–50/15 sec., and it is known that the phorbol ester, 4-β phorbol 12-myristate-13-acetate (PMA) reduces the contraction rate (Johnson, J. A. et al., *Circ Res* (1995) 76:654–653). Previous work has also shown that treating cardiac myocytes with PMA or with norepinephrine (NE) causes translocation of αPKC to the nuclear boundary, βIPKC to the interior of the nuclei, δPKC to the fibrillar and perinuclear structures, and εPKC to cross-striated structures (Disatnik, M-H. et al., *Exp Cell Res*

(1994) 210:287–297). It has also been shown that exogenously added activated PKCs bind similarly (Mochly-Rosen, D. et al., *Molec Biol Cell* (1990)1:693–706). Since the location to which the various isoenzymes are translocated are different, it has been suggested that the variable regions specific for each isoenzyme (Nishizuka, Y., *Nature* (1988) 334:661–665) should contain at least part of the specific RACK binding site (Disatnik, M-H. et al., *Exp Cell Res* (1994) 210:287–297). Furthermore, it has been suggested that the V1 region of εPKC determines its substrate specificity (Pears, C. et al., *Biochem J* (1991) 276:257–260).

To show that only translocation of the corresponding isoenzyme is inhibited by one of its fragments—e.g., only translocation of εPKC is inhibited by an εPKC-V1 fragment, cells cultured on chamber slides were permeabilized with saponin (50 μg/ml) in the absence or presence of 100 μg/ml rat recombinant εPKC-V1 or δPKC-V1 fragments containing amino acids 2–144 in each case. Cellular functions, including cell viability, spontaneous and stimulated contraction rates, gene expression and hypertrophy are unaffected by the saponin treatment.

These fragments were prepared by amplifying the relevant portion of the gene from a cDNA library (Stratagene). A FLAG™ epitope (DYKDDDK) (SEQ ID NO:16) was engineered at the 5' end of the fragment and the 0.45 kb PCR fragment was subcloned into pMAL-C2 vector (New England Biolabs) for overexpression as a fusion protein with maltose binding protein in *E. coli*. Protein purification and Factor Xa proteolysis of the fusion proteins was as described by Ron, D. et al., *Proc Natl Acad Sci USA* (1994) 91:839–843.

The intracellular concentration of each fragment was approximately 300 nM or about 3% of the extracellular concentration as determined by quantitative Western blot of washed and extracted cells.

After the εPKC-V1 or δPKC-V1 fragments were administered by permeabilization, the cells were incubated with either 4-α or 4-β PMA. (4α PMA is not active and is used as a control.) The cells were then fixed with methanol and acetone and PKC isoenzyme localization was determined by immunofluorescence; the antisera used to detect δPKC and εPKC do not recognize the administered fragments. Multiple fields of cells for each treatment group and for PKC isoenzymes α, βI, δ, and ε were observed and the data were presented as a percentage of cells having the tested enzyme at the activated site. When the cells were treated with 100 nM PMA for five minutes, it was apparent that neither δPKC-V1 nor εPKC-V1 had any effect on translocation of the α or β isoenzymes whereas each of the δ and ε fragments specifically inhibited the translocation of the corresponding isoenzyme, but not the other isoenzyme. An additional experiment measuring translocation of εPKC at the much lower level of 3 nM PMA also showed complete inhibition by the ε fragment. It has previously been shown that 3 nM PMA is only marginally effective in translocation of PKC isoenzymes other than the ε form (Johnson, J. A. et al., *Circ Res* (1995) 76:654–663).

Figure 2A:
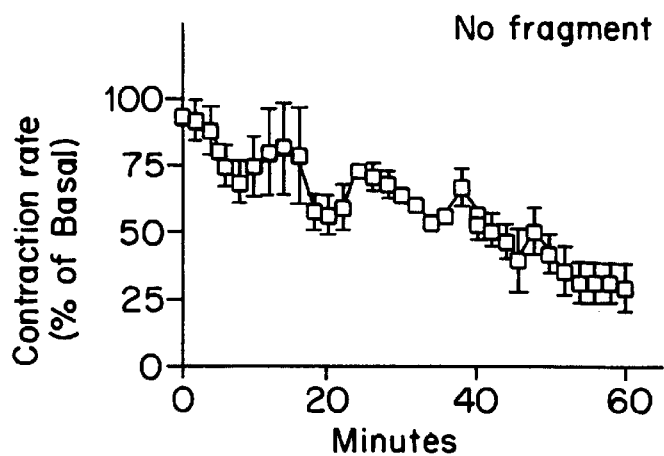
FIG. 2 shows the result of experiments demonstrating that PKC mediated effects on contraction of cardiac myocytes is inhibited by a fragment of the regulatory domain of εPKC but not by a corresponding fragment of δPKC.
Figure 2B:
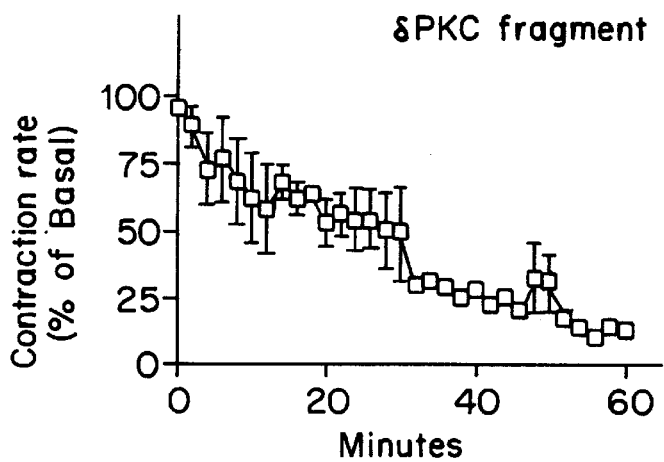
Figure 2C:
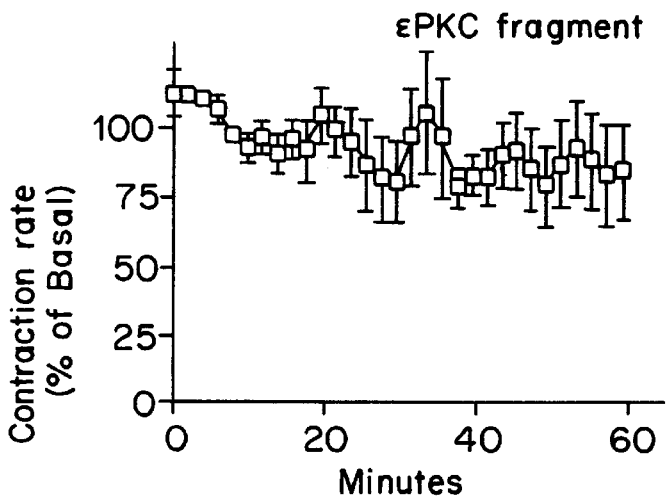

The localization of εPKC to the cross-striated structures suggested that the ε isoenzyme might mediate the effect of PMA on the contraction rate. Cells were cultured and permeabilized with saponin in the presence or absence of 150 μg/ml δ or εPKC-V1 fragments described above. Basal contraction rates were monitored for 10 min, and the cells were then treated with 3 nM PMA. The rate of contraction was monitored over the next 20 minutes. The results are shown in FIG. 2.

As shown, in cells where no fragment was added, the contraction rate is reduced almost to zero within 15 min of the addition of PMA. Similarly, in cells where the δ PKC fragment is added, the contraction rate is thus reduced. However, in cells where the εPKC fragment was added, the contraction rate is maintained. Thus, the εPKC-V1 fragments specifically prevented PMA-induced inhibition of spontaneous contraction. These data, combined with the data described above with respect to translocation and the fact that the εPKC-V1 fragment does not affect the catalytic activity of εPKC in vitro, demonstrate that the translocation of εPKC is an essential step in signaling the chronotropic effect of PMA and that this signaling is inhibited by a fragment containing the V1 region.

The effect of PMA in reducing the contraction rate can be mimicked by controlling the α1 and β1 adrenergic receptors of the myocytes, providing a more physiologically relevant phenomenon. If both the α1 and β1 receptors are activated with NE, an increase in contraction rate occurs; when both receptors are inhibited, NE no longer has this effect. If the α1 receptor is inhibited alone by prazosin, the initial increase in contraction rate is higher; if the β1 receptor alone is inhibited, the contraction rate decreases.

When either the δ or ε fragments described above is substituted for the known inhibitors of the α1 and β1 receptors, the behavior of the cells in response to NE is unaffected by the presence of the δ fragment; however, addition of the ε fragment gives a response similar to that obtained in the presence of prazosin. These data are consistent with the role of the ε fragment in controlling contraction rate since the α1 receptor (inhibited by prazosin) mediates PKC translocation.

Figure 3:
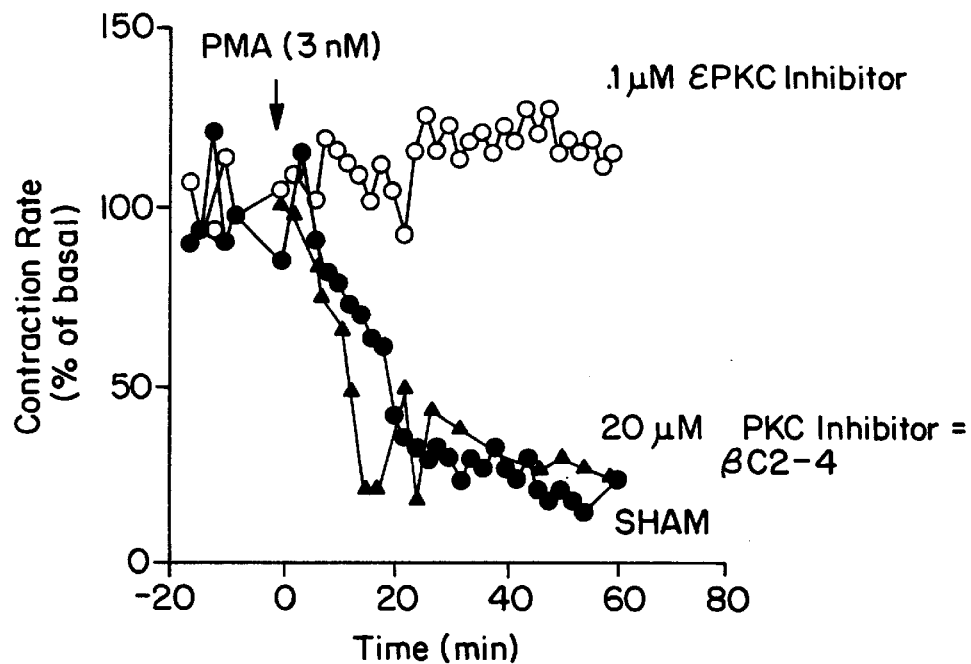
FIG. 3 shows the specific effect of an 8 amino acid peptide derived from the RACK-binding site in the regulatory domain of εPKC on the contraction rate of cardiac myocytes; an analogous peptide from the βPKC has no effect.

FIG. 3 shows the results of a similar experiment using stimulation with 3 nM PMA, and providing peptides of less than 10 residues that block localization of εPKC and βPKC using a 0.1 μM εPKC-derived peptide εV1-2 (sequence EAVSLKPT) (SEQ ID NO:17) or 20 μM of a βPKC-derived peptide βC2-4 (sequence SLNPEWNET) (SEQ ID NO:18). As shown in FIG. 3, stimulation with 3 nM PMA without adding peptides to the permeabilized cells or in the presence of 20 μM of the βPKC localization inhibitor results in negative chronotropy as above.

EXAMPLE 2

Specific Inhibition of βPKC Translocation by C2-Derived Peptides

The parent application herein described binding sites on a particular RACK, RACK1, which are responsible for binding βPKC. It is recognized that if the binding site on PKC is identified, peptides that mimic this binding site could also serve as modulators of βPKC translocation and function. Furthermore, it should be noted that PKC may itself contain pseudo-RACK peptide sequences that mimic the binding sites on RACK and regulate the exposure of the binding site for RACK on PKC. The following experiments do not distinguish between these possibilities; nevertheless, whichever function on the PKC sequence is represented, mimics of the sequence will be effective modulators of the relevant signal pathway.

The cPKC class of isozymes comprises the only members of the PKC general family that contains C2 regions. Other C2-containing proteins such as synaptotagmin and phospholipase Cγ also bind to a mixture of RACKs prepared from cell particulate fractions. It has also been demonstrated that recombinant fragments of synaptotagmin containing the C2 homologous region bind to mixtures of RACKs and inhibit PKC binding to RACKs (Mochly-Rosen, D. el al., *Biochemistry* (1992) 31:8120–8124).

The following experiments demonstrate that certain peptides residing in the C2 region of βPKC are able to inhibit translocation of βPKC and the maturation of Xenopus oocytes. Ron, D. et al., *J Biol Chem* (1995) 270:24180–24187.

The following βPKC-derived peptides were prepared:

βC2-1 (SEQ ID NO:19): KQKTKTIK (210–217);

βC2-2 (SEQ ID NO:20): MIDPNGLSDPYVKL (186–198);

βC2-3 (SEQ ID NO:21): IPDPKSE (201–207);

βC2-4 (SEQ ID NO:18): SLNPEWNET (218–226);

Scrambled βC2-1 (SEQ ID NO:22): TKQKKITK;

Control Peptide (SEQ ID NO:23): LQKAGVDG (266–271).

Recombinantly produced fragments of βPKC were expressed as fusion proteins with GST: Fusion L9 includes the V1 region, the pseudosubstrate sequence, and the C1 and V2 regions (residues 3–182) of βPKC. L10 includes the V1 region, the pseudosubstrate sequence and the first cysteine repeat from the C1 region, as well as the entire C2 and V3 regions (residues 3–76 and 143–339). The numbering is as described in Luo, J-H. et al., *J Biol Chem* (1993) 248:3715–3719.

Standard overlay assays were performed by blotting RACKI onto nitrocellulose as described by Mochly-Rosen, D. et al., *Proc Natl Acad Sci USA* (1991) 88:3997–4000. Strips of the nitrocellulose sheet containing 0.1–1 μg RACK1 per strip were incubated in overlay buffer with or without the test fragment added at approximately 10 μM. Addition was in the presence or absence of 50 μg/ml phosphatidyl serine (PS) and 1 mM calcium. The mixture was further incubated for 30 min at room temperature. The strips were then washed and binding of fragment of L9 or L10 to RACK1 was detected with anti-GST polyclonal antibodies followed by labeling with anti-rabbit horseradish peroxidase-linked antibodies and development by addition of substrate.

Using this assay, L10, but not L9 was found to bind RACK1. The PKC activators phosphatidyl serine and calcium did not increase the binding of L10 to RACK1, although these activators are necessary for the binding of intact PKC to RACK1. Thus, these data are consistent with the suggestion that the PKC activators are required to expose the RACK binding site in the intact PKC; this site is already exposed in the C2-containing fragment L10.

To determine whether L10 would inhibit the binding of intact βPKC to RACK1, RACK1 was immobilized on an amylose column and βPKC binding in the presence of PS, DAG and calcium and in the presence of L10 or L9 was determined. In the presence of L10, βPKC binding to RACK1 was completely inhibited; however, this was not true of L9. Similar results were obtained in an overlay assay.

Similar overlay assays were conducted using the above-listed peptides as candidate inhibitors for the binding of L10 to RACK1. The C2-derived peptides βC2-1, βC2-2 and βC2-4 peptides were successful in inhibiting binding of L10 to RACK1; however βC2-3 and scrambled βC2-1 were not.

In addition to the foregoing cell-free assays, the association of βPKC with RACK1 and the ability of peptides derived from the C2 region to interrupt this interaction was tested in rat neonatal cardiac myocytes in culture. The presence of RACK1 in these cells was confirmed by immunostaining. RACK1 was found at perinuclear structures and throughout the cytosol. Treating with NE or PMA did not alter these locations. It was also demonstrated that activated βII PKC, but not C2-less isoenzymes δ or εPKC, colocalized with RACK1.

The C2-derived peptides that had been shown to inhibit βPKC binding to RACK1 in vitro were then tested for their ability to inhibit activation-induced translocation in myocytes.

The myocytes were exposed to 100 nM PMA for 15 min after transient permeabilization with saponin (50 μg/ml) in the presence and absence of the test peptides. 80% of the cells that had not been treated with peptides showed localization of β1 PKC to perinuclear structures. However, when βC2-1, βC2-2 or βC2-4 at 10 μM extracellular concentration had been supplied to the permeabilized cells, translocation of both βI PKC and βII PKC isoenzymes was inhibited by 65–95%. βC2-4 was the most effective. Control peptides described above did not affect translocation.

Consistent with the results in Example 1, treating non-permeabilized cardiac myocytes with 100 nM PMA resulted in translocation of εPKC from the nucleus to the perinuclear and cross-striated structures and of δPKC from the perinuclear and fibrilar cytosolic structures in 80% and 90% of the cells respectively. Permeabilization and treatment of the cells with the C2 peptides derived from βPKC had no effect on the translocation of these C2-less isozymes.

While the chronotropy of myocytes is not affected by βPKC isoenzymes, the insulin-induced maturation of Xenopus oocytes is mediated by the β form. Insulin treatment of these oocytes results in translocation of βPKC and maturation is delayed by the PKC-specific catalytic inhibitor pseudosubstrate peptide. PKC translocation is blocked by injection of purified RACKs or a peptide corresponding to the PKC binding site on RACKs. (Smith, B. L. el al., *Biochem Biophys Res Commun* (1 992) 188:1235–1240; Ron, D. et al., *J Biol Chem* (1 994) 269:21395–21398).

Figure 4:
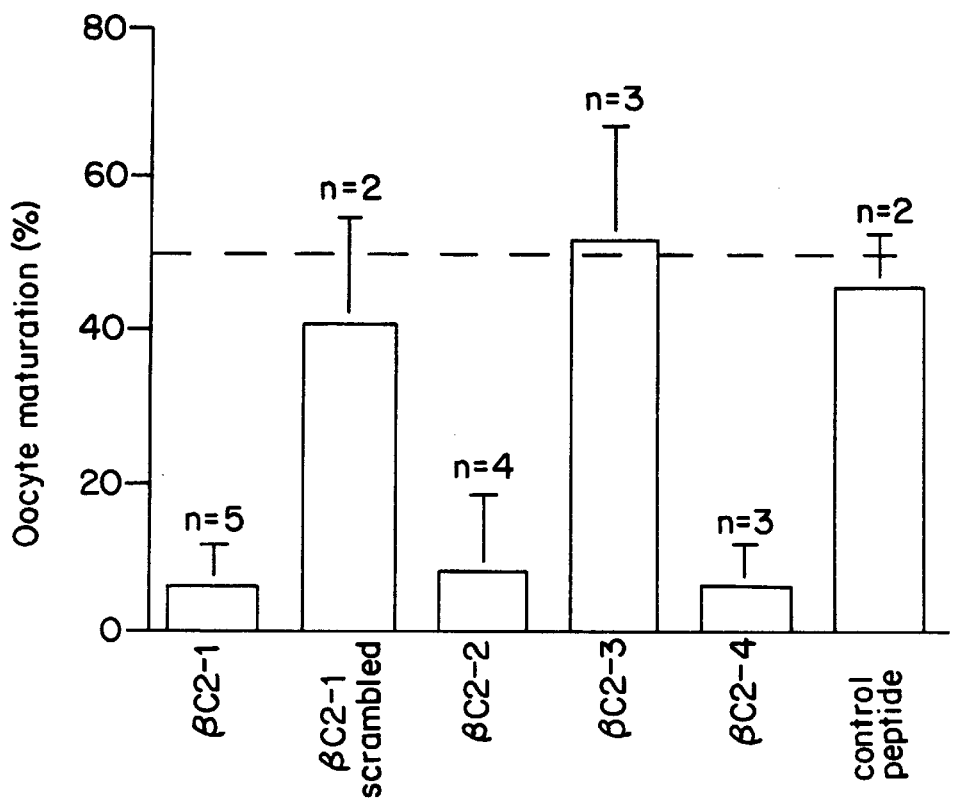
FIG. 4 shows the specific effect of peptides derived from the RACK-binding site of βPKC on maturation of Xenopus oocytes.

Accordingly, the maturation of Xenopus oocytes was used as an alternative assay system to test the function of the peptides derived from the C2 region described above. In this assay, oocytes were injected with 50 μM of the test peptide one hour before insulin treatment (8.25 μg/ml). Insulin-induced oocyte maturation was then determined by monitoring the appearance of a white spot in the animal pole of the oocyte that is indicative of germinal vesicle breakdown in maturation. 10–15 oocytes were included per assay and oocytes were scored for 35 hours after treatment. As expected, βC2-1, βC2-2 and βC2-4 supplied in the range of 5 μM-500 μM significantly delayed oocyte maturation in a dose-dependent manner. The control peptides did not. The association of this effect with the prevention of translocation of βPKC to the particulate fraction in Xenopus oocytes was confirmed in a separate experiment. The peptide βC2-4 inhibited βPKC translocation but not θPKC in Jurkat T-cells. FIG. 4 shows the effect of these various peptides on Xenopus oocyte maturation.

EXAMPLE 3

Agonist Effect of Interacting Peptides

Figure 5A:
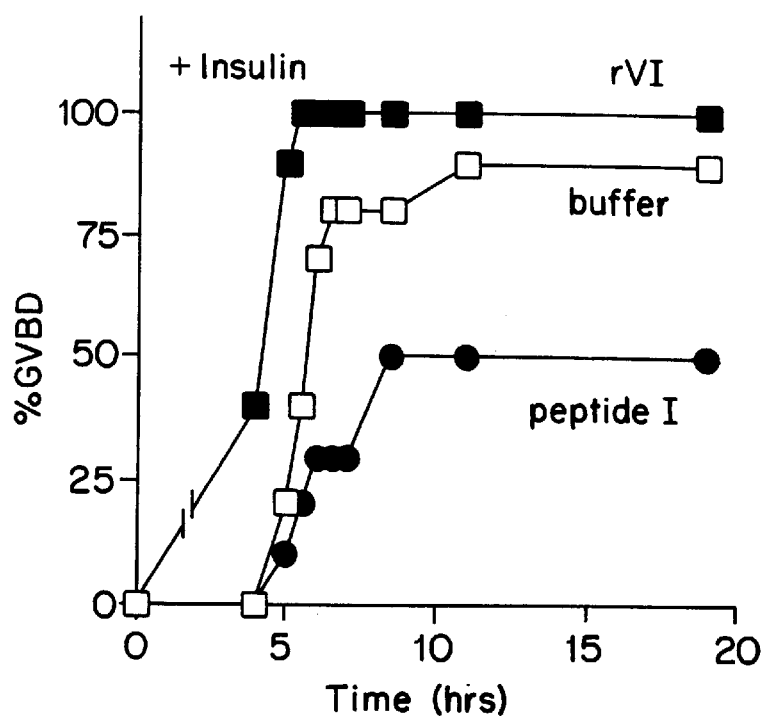
FIG. 5 shows the effects of peptides derived from RACK1 on PKC mediated maturation of Xenopus oocytes.
Figure 5B:
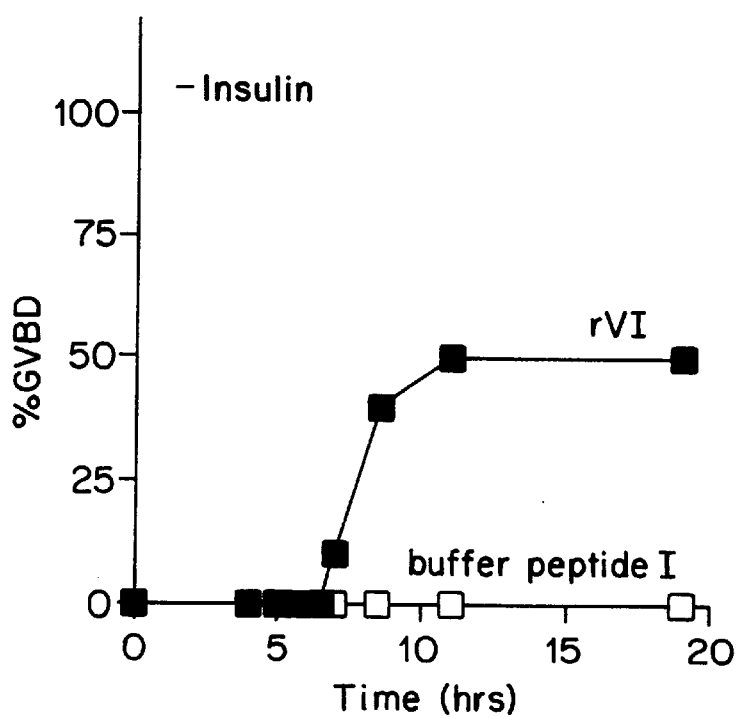

The oocyte maturation assay described above was also used to test the effect of various peptides derived from the PKC/RACK1 pair. Peptide I, derived from RACK1, as expected, inhibits the maturation of Xenopus oocytes presumably by interfering with the binding of βPKC1 to RACK1. On the other hand, a short peptide, rVI derived from the sixth WD-40 repeat in RACK1 enhances maturation, both in the presence and absence of insulin. Ron, D., Mochly-Rosen, D., *J. Biol. Chem.* (1994) 269:21395–21398 These results are shown in FIGS. 5 and 5b. The rVI peptide is believed to interfere with the RACK-mimicking site on PKC which normally covers the RACK-binding site in the absence of activation.

EXAMPLE 4

Figure 6:
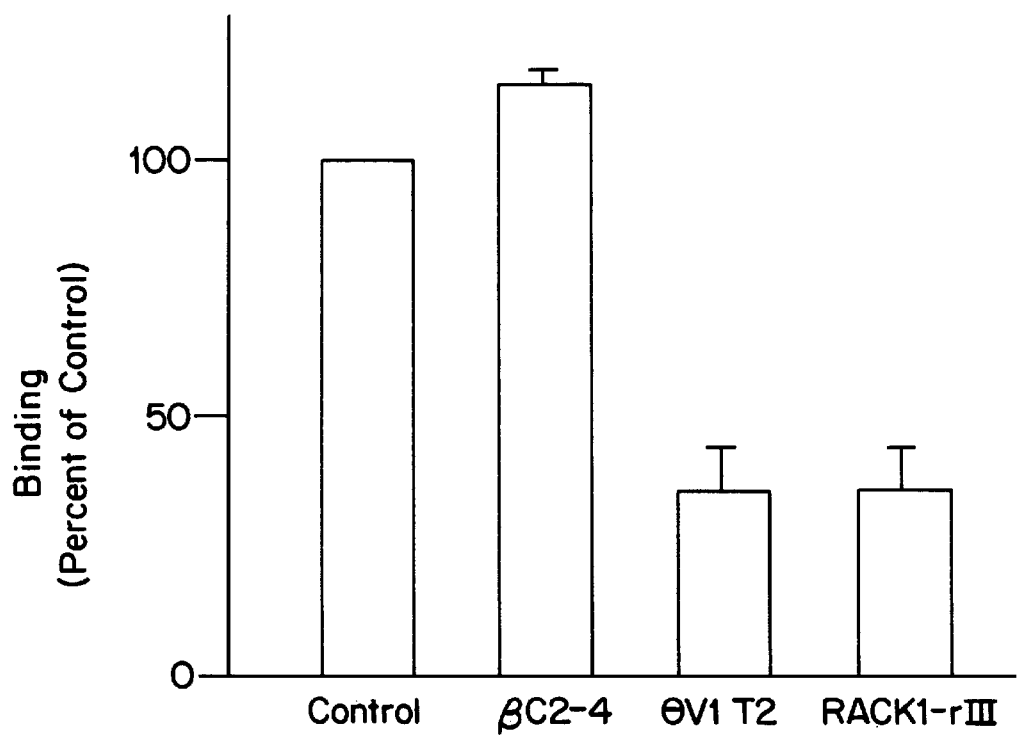
FIG. 6 shows the effect of various peptides on the binding of θPKC V1 fragment to RACK1 in vitro.

Interaction Peptides Derived from θPKC

θPKC is a member of the NPKC family and lacks a C2 region. Comparison of variable sequences with εPKC and other isozymes reveals regions of maximum disparity. Of these regions, some are strongly conserved across vast phylogenetic spans, e.g., from mammals to the invertebrate Aplysia. Isozyme specific sequences that are strongly conserved by evolution are probable sites for binding cognate proteins. Comparing δPKC to θPKC in the analogous region allowed identification of a θ-specific peptide expected to interfere with PKC binding to a RACK. Peptides with these characteristics from the V1 region of θPKC were prepared and tested for their ability to inhibit the binding of θPKC V1 fragment to RACK1 in vitro. The results are shown in FIG. 6. Of a multiplicity of peptides tested, both from other regions of the θPKC isoenzyme and from alternative isoenzymes in the family, only θV1 derived peptides T1 and T2, having the amino acid sequences GLSNFDCG (SEQ ID NO:24) (θPKC residues 8–15) and YVESENGQMYI (SEQ ID NO:25) (θPKC residues 36–46), respectively, were able to affect the interaction negatively. As expected, peptides rIII and rVI derived from the WD-40 regions of RACK1 were also effective.

Figure 11A:
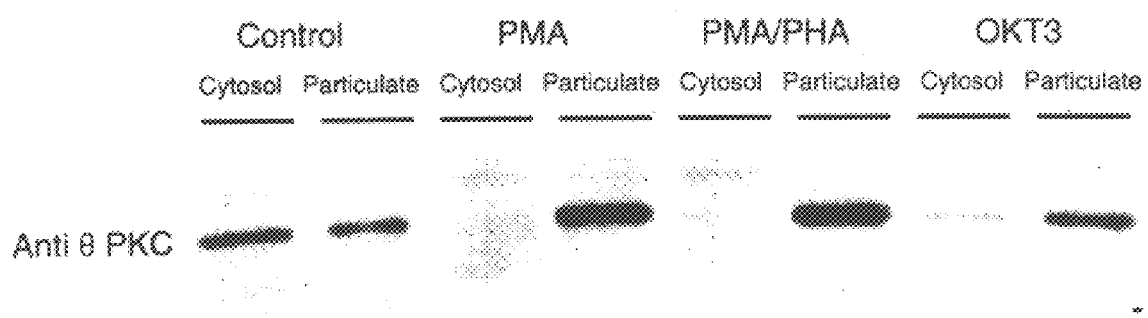
FIGS. 11A and 11B is aphotocopy of a blot which shows the effect of activation by various agents on translocation of PKC-theta and PKC-beta.

The peptides T1 and T2 could inhibit the translocation of θPKC to the cellular particulate fraction in Jurkat T-cells. The specificity of this interaction is shown in FIG. 11A which shows inhibition by the θPKC V1 peptide (T2) of the translocation of θPKC but not of βPKC.

Sequences derived from other PKC regions.

V3 region. The V3 or hinge region separates the regulatory and catalytic domains. This region contains the sites of proteolysis by trypsin and calpain. The lack of conservation of the V3 domain between the different PKC isozymes suggests that this section may also be at least, in part, involved in targeting the PKC isozymes to their anchoring proteins. Furthermore, it has been demonstrated that regions within the V3 of αPKC mediate the translocation of that isozyme to the nucleus (James G., and Olson E. *J. Cell Biol.* 116:863–873, 1992). The V3 region of θPKC was found to bind to RACK1 in vitro. Therefore, the V3 region could affect not only the targeting of the activated isozymes (in which the V3-region is exposed) but could also regulate the enzyme susceptibilities to proteolysis. Antibodies made against theta V3 fail to precipitate fyn, suggesting competition for the same sites on V3.

V5. The amino acid sequences of the βPKC isoforms βIPKC and βIIPKC are identical except for variability within the V5 region (35 amino acids for βIPKC and 38 amino acids for βIIPKC). Upon activation, βIPKC and βIIPKC translocate to different localization sites in the cell (Disatnik M. -H., Buraggi G., Mochly-Rosen D. *Exp. Cell Res.* (1994) 210:287–297). This difference in localization of isozymes that are almost identical can be explained by the importance of the V5 region in mediating their targeting. Moreover, βIIPKC was found to selectively translocate to the nucleus upon proliferative stimulation where it selectively phosphorylated the nuclear envelope protein Iamin $B_1$. (Murray N. R. et al. *J. Biol. Chem.* (1994) 269:1385–2191).

PKC-related proteins. A distant homolog has been designated PKC-mu. It is unusual in that is has an N-terminal transmembrane domain. Recently the human cDNAs encoding two novel protein kinases have been cloned. These proteins termed PRK1 and PRK2 (protein kinase C related kinase I and 2) show high homology to each other and some homology to the regulatory region of PKC (Palmer R. H., et al. *Eur. J. Biochem.* (1995) 227:344–351. Since the sequences within the regulatory domain of PKC are responsible for the interaction between a PKC and its anchoring proteins, sequences from PRK1 and PRK2 which show homology to functionally important sequences within the regulatory domain of PKC, are likely to be of biological importance.

Sequences from other isozymes and related proteins that meet the same isozyme selectivity/evolutionary conservation criteria include the following:

| Peptide | Sequence | Position |
|---|---|---|
| Peptides derived from the V1 region of PKC isozymes (Human): | | |
| (SEQ ID NO: 24) θV1-1 | G-L-S-N-F-D-C-G | θPKC(8–15) |
| (SEQ ID NO: 25) θV1-2 | Y-V-E-S-E-N-G-Q-M-Y-I | θPKC(36–46) |
| (SEQ ID NO: 26) θV1-3 | I-V-K-G-K-N-V-D-L-I | θPKC(73–82) |
| (SEQ ID NO: 27) θV1-4 | D-M-N-E-F-E-T-E-G-F | θPKC(130–139) |
| (SEQ ID NO: 28) δV1-1 | A-F-N-S-Y-E-L-G-S | δPKC(8–16) |
| (SEQ ID NO: 29) δV1-2 | A-L-S-T-E-R-G-K-T-L-V | δPKC(35–45) |
| (SEQ ID NO: 30) δV1-3 | V-L-M-R-A-A-E-E-P-V | δPKC(72–82) |
| (SEQ ID NO: 31) δV1-4 | Q-S-M-R-S-E-D-E-A-K | δPKC(129–138) |
| (SEQ ID NO: 32) εV1-1 | N-G-L-L-K-I-K | εPKC(5–11) |
| (SEQ ID NO: 17) εV1-2 | E-A-V-S-L-K-P-T | εPKC(14–21) |
| (SEQ ID NO: 33) εV1-3 | L-A-V-F-H-D-A-P-I-G-Y | εPKC(81–91) |
| (SEQ ID NO: 34) εV1-4 | D-D-F-V-A-N-C-T-I | εPKC(92–100) |
| (SEQ ID NO: 35) εV1-5 | W-I-D-L-E-P-E-G-R-V | εPKC(116–125) |
| (SEQ ID NO: 36) εV1-6 | H-A-V-G-P-R-P-Q-T-F | εPKC(27–36) |
| (SEQ ID NO: 37) εV1-7 | N-G-S-R-H-F-E-D | εPKC(108–115) |
| (SEQ ID NO: 38) ηV1-1 | N-G-Y-L-R-V-R | ηPKC(9–15) |
| (SEQ ID NO: 39) ηV1-2 | E-A-V-G-L-Q-P-T | ηPKC(18–25) |
| (SEQ ID NO: 40) ηV1-3 | L-A-V-F-H-E-T-P-L-G-Y | ηPKC(84–94) |
| (SEQ ID NO: 41) ηV1-4 | D-F-V-A-N-C-T-L | ηPKC(95–102) |
| (SEQ ID NO: 42) ηV1-5 | W-V-D-L-E-P-E-G-K-V | ηPKC(120–129) |
| (SEQ ID NO: 43) ηV1-6 | H-S-L-F-K-K-G-H | ηPKC(31–38) |
| (SEQ ID NO: 44) ηV1-7 | T-G-A-S-D-T-F-E-G | ηPKC(111–119) |
| (SEQ ID NO: 45) μV1-1 | M-S-V-P-P-L-L-R-P | μPKC(1–9) |
| (SEQ ID NO: 46) μV1-2 | K-F-P-E-C-G-F-Y-G-L-Y | μPKC(86–96) |
| (SEQ ID NO: 47) λV1-1 | H-Q-V-R-V-K-A-Y-Y-R | λPKC(15–24) |
| (SEQ ID NO: 48) λV1-2 | Y-E-L-N-K-D-S-E-L-L-I | λPKC(87–94) |
| (SEQ ID NO: 49) ζV1-1 | V-R-L-K-A-H-Y | ζPKC(16–22) |

| Peptide | Sequence | Position |
|---|---|---|
| (SEQ ID NO: 50) | | |
| ζV1-2 | V-D-S-E-G-D | ζPKC(61–66) |
| (SEQ ID NO: 51) | | |
| ζV1-3 | V-F-P-S-I-P-E-Q | ζPKC(95–102) |
| Peptides derived from the V3 region of PKC isozymes (Human): | | |
| (SEQ ID NO: 52) | | |
| δV3-1 | Q-G-F-E-K-K-T-G-V | δPKC(312–320) |
| (SEQ ID NO: 53) | | |
| δV3-2 | D-N-N-G-T-Y-G-K-I | δPKC(327–335) |
| (SEQ ID NO: 54) | | |
| εV3-1 | S-S-P-S-E-E-D-R-S | εPKC(336–344) |
| (SEQ ID NO: 55) | | |
| εV3-2 | P-C-D-Q-E-I-K-E | εPKC(351–358) |
| (SEQ ID NO: 56) | | |
| εV3-3 | E-N-N-I-R-K-A-L-S | εPKC(360–368) |
| (SEQ ID NO: 57) | | |
| εV3-4 | G-E-V-R-Q-G-Q-A | εPKC(393–400) |
| (SEQ ID NO: 58) | | |
| λV3-1 | M-D-Q-S-S-M-H-S-D-H-A-Q-T-V-I | λPKC(194–208) |
| (SEQ ID NO: 59) | | |
| λV3-2 | L-D-Q-V-G-E-E | λPKC(218–224) |
| (SEQ ID NO: 60) | | |
| λV3-3 | E-A-M-N-T-R-E-S-G | λPKC(227–234) |
| (SEQ ID NO: 61) | | |
| μV3-1 | D-P-D-A-D-Q-E-D-S | μPKC(390–398) |
| (SEQ ID NO: 62) | | |
| μV3-2 | S-K-D-T-L-R-K-R-H | μPKC(440–448) |
| (SEQ ID NO: 63) | | |
| μV3-3 | I-T-L-F-Q-N-D-T-G | μPKC(457–465) |
| (SEQ ID NO: 64) | | |
| μV3-4 | G-S-N-S-H-K-D-I-S | μPKC(559–567) |
| (SEQ ID NO: 65) | | |
| θV3-1 | C-S-I-K-N-E-A-R-L | θPKC(322–330) |
| (SEQ ID NO: 66) | | |
| θV3-2 | G-K-R-E-P-Q-G-I-S | θPKC(337–345) |
| (SEQ ID NO: 67) | | |
| θV3-3 | D-E-V-D-K-M-C-H-L | θPKC(351–359) |
| (SEQ ID NO: 68) | | |
| ζV3-1 | S-Q-E-P-P-V-D-D-K-N-E-D-A-D-L | ζPKC(194–208) |
| (SEQ ID NO: 69) | | |
| ζV3-2 | I-K-D-D-S-E-D | ζPKC(217–223) |
| (SEQ ID NO: 70) | | |
| ζV3-3 | P-V-I-D-G-M-D-G-I | ζPKC(226–234) |
| (SEQ ID NO: 71) | | |
| βV3-1 | V-P-P-E-G-S-E-A | βPKC(290–297) |
| (SEQ ID NO: 72) | | |
| αV3-1 | I-P-E-G-D-E-E-G | αPKC(290–297) |
| (SEQ ID NO: 73) | | |
| γV3-1 | V-A-D-A-D-N-C-S | γPKC(290–297) |
| Peptides derived from the V5 region of PKC isozymes (Human): | | |
| (SEQ ID NO: 74) | | |
| αV5-1 | Q-L-V-I-A-N | αPKC(642–647) |
| (SEQ ID NO: 75) | | |
| βIV5-1 | K-L-F-I-M-N | βIPKC(646–651) |
| (SEQ ID NO: 76) | | |
| βIIV5-1 | Q-E-V-I-R-N | βIIPKC(645–650) |
| (SEQ ID NO: 77) | | |
| δV5-1 | K-N-L-I-D-S | δPKC(649–654) |
| (SEQ ID NO: 78) | | |
| εV5-1 | E-A-I-V-K-Q | εPKC(714–719) |
| (SEQ ID NO: 79) | | |
| ηV5-1 | E-G-H-L-P-M | ηPKC(657–662) |
| (SEQ ID NO: 80) | | |
| λV5-1 | D-D-I-V-R-K | λPKC(559–564) |
| (SEQ ID NO: 81) | | |
| μV5-1 | S-D-S-P-E-A | μPKC(898–903) |
| (SEQ ID NO: 82) | | |
| θV5-1 | R-A-L-I-N-S | θPKC(680–685) |
| (SEQ ID NO: 83) | | |
| ζV5-1 | E-D-A-I-K-R | ζPKC(556–561) |
| Peptides derived from protein kinase C related proteins (Human): | | |
| (SEQ ID NO: 84) | | |
| PRK1-1 | Q-D-S-K-T-K-I-D | PRK1(171–178) |
| (SEQ ID NO: 85) | | |
| PRK2-1 | Q-D-S-K-T-K-I-E | PRK2(181–188) |
| (SEQ ID NO: 86) | | |
| PRK1-2 | E-L-A-V-F-W-R-D | PRK1(430–437) |
| (SEQ ID NO: 87) | | |
| PRK2-2 | E-I-S-V-Y-W-R-D | PRK2(432–439) |
| (SEQ ID NO: 88) | | |
| PRK1-3 | M-E-P-Q-G-C-L | PRK1(465–471) |
| (SEQ ID NO: 89) | | |
| PRK2-3 | L-E-P-Q-G-T-L | PRK1(467–473) |

μV1-1, μV 1-2 derived from μPKC were picked because they aligned with εV1-2 and θV1-2 and part of θV1-1 respectively. λV1-1 and λV1-2 from λPKC were picked based on their alignment with εV1-2 and part of εV1-3 and θV1-2 respectively. ζV1-1, ζV1-2, ζV1-3 derived from ζPKC were picked according to their homology to: εV1-2, θV1-2, and εV1-2 respectively. PRK1-1 and PRK2-2 were identified according to their homology to βC2-1. PRK1-2 and PRK2-2 were identified according to their homology to the biologically active εPKC-derived peptide εV1-3 and part of εV1-2. PRK 1-3 and PRK2-3 were picked according to their alignment with the peptide εV1-5.

The peptide sequences were generated by aligning the human PKC sequences and the human PRK1 and PRK2 sequences using the MegAlign DNASTAR Inc. program. The sequences were aligned by using the clustal method. The algorithm groups sequences into clusters by examining the distances between all pairs. The clusters are aligned, first individually, then collectively to produce an overall alignment. (Higgins D. G. et al. (1989). *CABIOS* 5(2):151–153). The matrix for the alignment was PAM250 (percent accepted mutation 250-2.5 mutations per residue). This matrix allows only high stringency alignments.

EXAMPLE 5 fyn as a PKC-theta Cognate

In this example, evidence is provided which identifies a specific protein as a cognate binding partner to PKC-theta in T-cells. This protein is a tyrosine protein kinase called fyn, which was previously known and believed to play an important role in T-cell function. Evidence is further provided to demonstrate that disrupting the localization of PKC-theta, using peptides from the PKC domain which interacts with fyn, depresses T-cell function.

The T-cell receptor (TCR) complex comprises at minimum the CD3 and CD4 complexes of proteins, to which several tyrosine kinases are associated. PLC-gamma, important in generating second messengers such as diacylglycerol and inositol triphosphate, is also a substrate for tyrosine phosphorylation. Among the non-receptor tyrosine kinases are ZAP-70 and the src-related proteins fyn and lck, believed to interact with CD3 and CD4 respectively; another tyrosine kinase, csk, is also associated with the TCR supercomplex of proteins.

In some reports, fyn is only included in 1% of the CD3 complexes. A transient association makes sense, however, in the context of what is known about other localization factors, such as RACK1 for PKC, which are similarly present in particular places in the cell only during particular signal transduction episodes. A role for fyn in T-cell signaling is well documented, including association with at least half a dozen other proteins which are also associated under some experimental conditions with TCR (Penninger el al., *Immunol. Rev.* 135:183–214 (1993). An association of fyn with PKC has not been previously observed.

The evidence that fin interacts with PKC-theta comes from several independent and mutually supportive lines of experimentation. In most cases, the region of PKC-theta used to define the binding specificity was the V1 region (~140 amino acids), which is from the regulatory domain of PKC and is a sequence unique to this isozyme; some experiments also used the V3 domain, FIG. 1. Proteins that interact with these regions fulfill the criteria defined in Examples 1–4. In the data provided in Example 1–4, RACK1 was shown to have some degree of binding to PKC-theta, which could be partially blocked with the T1 or T2 peptides (derived from the V1 region). Both peptides were also able to inhibit normal subcellular translocation of PKC-theta following treatment with activators of the signal transduction network; the latter experiments indicate the importance of the V1 region but do not suffice to identify the physiologically relevant cognate binding partner.

To identify the physiologically relevant cognate binding partner, a Triton (non-ionic detergent) cell extract was prepared from Jurkat T-cells (a human T-cell lymphoma line) using standard procedures. Based on the prior experience that physiologically relevant cognate binding partners for PKC may be associated with the particulate fraction, the "Triton extract" included both soluble and some particulate fraction proteins and is referred to herein as the Triton extract. A V1-his tail construct was also engineered; six histidine residues were attached to the N-terminus of V1. The six histidine residues bind to nickel agarose affinity beads.

Using these beads as an affinity extraction medium, the V1 region was immobilized and incubated with the Triton extract. After washing (by centrifugation in an Eppendorf tube), the bound proteins were eluted with strongly denaturing SDS gel sample buffer. After the eluate was separated by gel electrophoresis and transferred to a membrane, fyn was detectable at the correct molecular weight using a fyn specific antibody (Santa Cruz Biotechnology, Santa Cruz, Calif.). A band at the same molecular weight was also detected by antibodies to phosphotyrosine (Transduction Laboratories, Lexington, Ky.). Antibodies to a related tyrosine kinase, csk, did not indicate any binding to the PKC domain.

Figure 7:
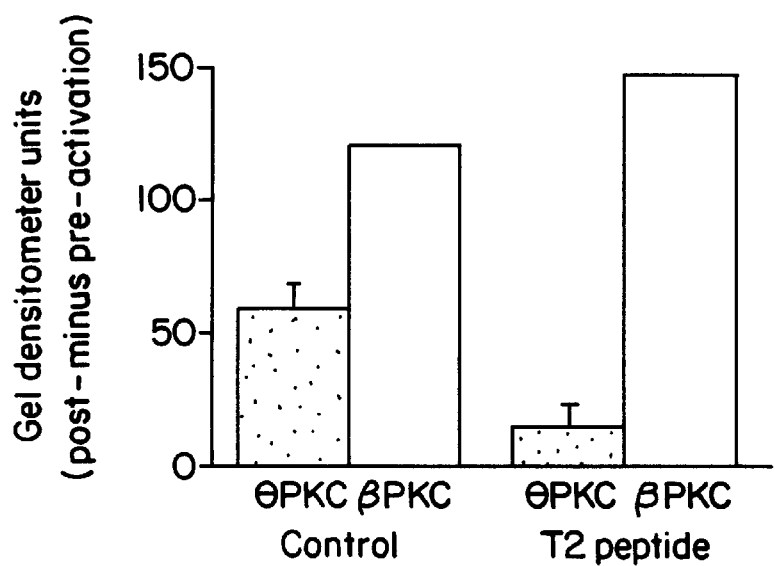
FIG. 7 is a photocopy of a blot obtained from a gel electrophoresis performed on proteins precipitated with antibodies raised against the V1/C1 boundary region of PKC-theta and probed with antibodies to phosphotyrosine and to fyn.
Figure 7A:
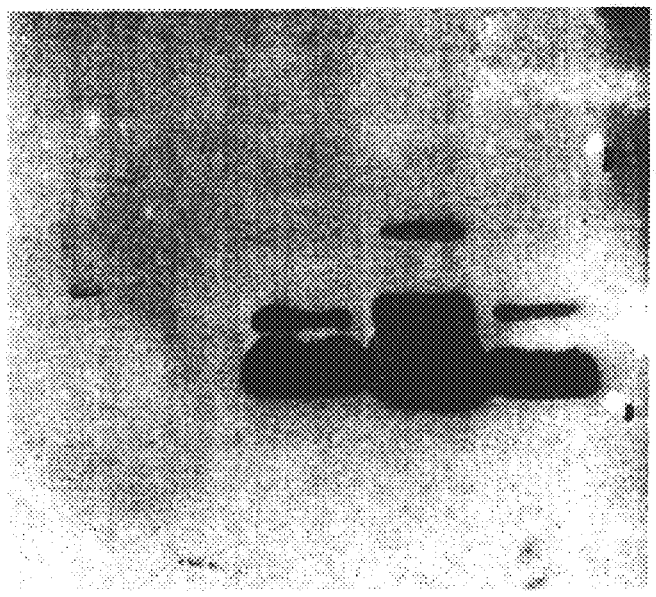
Figure 7B:

Antibodies prepared against the V1/C1 boundary (isozyme-specific) region of PKC-theta were used to immunoprecipitate PKC-theta and any associated proteins from the particulate fraction of an extract from Jurkat T-cells (overnight at 4°). These associated proteins were separated by gel electrophoresis and blotted to a membrane. When the blot was probed with an antibody against phosphotyrosine, several bands were identified including a prominent one at the MW of fyn, 59 kDa, FIG. 7A. By contrast, a band at the MW of lck, another fyn-related tyrosine kinase, was not identified as shown by probing with the appropriate antibody. Direct evidence that the coprecipitated protein is fyn was provided by staining with a commercially available labeled antibody prepared against fyn, FIG. 7B. As a control for specificity, antibodies to PKC-beta were successfully used to coprecipitate RACK1, the known cognate binding protein for this isozyme; fyn was not coprecipitated in this case.

To define the fyn subsequence specificity of interaction, a modified yeast two hybrid system was used (U.S. Pat. No. 5,283,173, Vojtek et al. *Cell* 74:205–214 (1993). Gene sequences for PKC-theta V1 and fyn were cloned as fusions to complementing halves of a transcription factor. In the particular system used, two reporter genes become activated as a consequence of the association between the two hybrid proteins, which thereby restores the holoenzyme status of the transcriptional activator. The first reporter is a histidine auxotroph repair enzyme, allowing growth selection; the second is beta-galactosidase, whose activity can be visualized with the substrate x-gal which turns blue following enzymatic cleavage. Visual inspection of the colonies allows scoring of interactions as strong (full color development within 2 hours), weak (by 12 hours), null (no signal at 24 hours). Liquid phase assays can also provide quantitative data. Miller, J. H. *Experiments in Molecular Genetics* (1972) Cold Spring Harbor Laboratory Press.

The catalytic domain and the regulatory domain of fyn were therefore tested separately as binding partners to the V1 region of PKC-theta. The catalytic domain gave a strong signal, and the regulatory domain gave a medium signal. It is not known if each domain folds equally well into a stable structure, so this difference is not conclusive as to what portion of fyn has the best binding to V1. The V3 region of PKC-theta has also been tested against the fyn regulatory, and catalytic domain constructs; both interact as measured by his selection, with beta-galactosidase experiments all showing strong interaction. It thus appears that PKC-theta interacts within over a substantial contact surface, in contrast to coprecipitation experiments using antibodies to the V1 region. In these experiments, antibodies to the V3 region failed to immunoprecipitate fyn, suggesting that the V3 antibodies and fyn are binding in part to the same site.

FIG. 8 thus shows the results of the two-hybrid assay wherein the fyn peptide to be tested is fused to a DNA encoding the polymerase activating domains (of the VP 16 transcription factor) and the relevant portion of the PKC-theta protein is fused to the DNA binding region of the transcription factor (LexA). Beta galactosidase was used as a reporter gene for the results in this Figure.

Figures 8A, 8B:
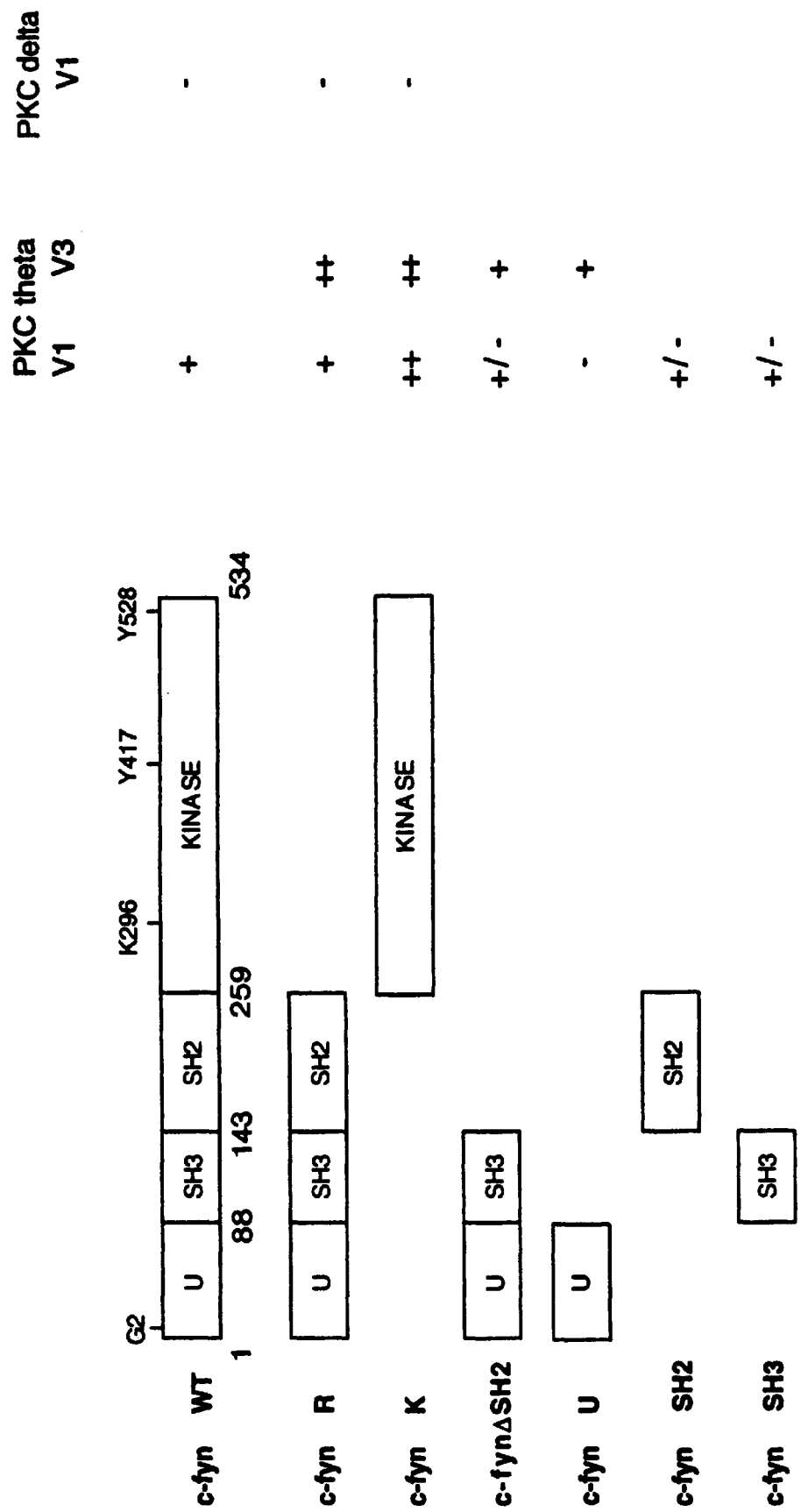
FIG. 8 shows the regions of fyn (panel A) used in a yeast two hybrid system; the resulting interactions are diagrammed in panel B. In panel B, ++ is a strong interaction (color development in <2 hr), + is a weak interaction (color development within 12 hours), and − is a null interaction (no color at 24 hours). U refers to the Unique sequence portion of fyn; SH3 and SH2 are the src homology domains; kinase is the conserved tyrosine protein kinase catalytic domain.

FIG. 8A shows the constructs and FIG. 8B summarizes the results. In addition to full-length fyn, the regulatory regions represented by fyn positions 1–259 interact strongly with the V1 and V3 regions of PKC-theta as does the kinase region from positions 259–534. fynΔSH2, representing positions 1–143 shows diminished interaction with both V1, although interaction is still present. A peptide representing positions 1–88 interacts only weakly with PKC-theta V3 and does not appear to interact with V1. Only very weak interaction between positions 88–143 (SH3) and 143–259 (SH2) with PKC-theta V1 is observed.

To test the specificity of the interaction of PKC-theta V1 with the fyn domains as compared to other proteins, the two hybrid system constructs incorporating the fyn portions were diluted into a large excess of random cDNA clones, prepared from murine T-cells, in the analogous vector. For the kinase domain, 10 of 12 positive clones picked at random were the fyn construct which had been spiked into the library; for the regulatory domain, 3 of 6 were from the spiked fyn construct. The other positive clones are further described in Example 8. The interaction of PKC-theta with fyn appears to be specific since an analogous construct using the V1 region of the most closely related isozyme, PKC-delta, did not appear to bind to fyn.

FIG. 9 represents a diagram and sequence of the fyn splice variant detected in this example, p59 fyn. It is possible that PKC binds at the interface between the two fyn domains, which are both exposed upon activation. A PKC consensus phosphorylation site has been identified within the primary sequence of fyn, centered on threonine-297, in a short stretch of sequence that also scores high as part of an ATP binding consensus site. It is known that fyn has alternative splicing forms; the form found in T-cells includes the consensus PKC site, although this site is not unique to T-cells. Interestingly, addition of ATP to Jurkat T-cell extracts reduces the association of PKC-theta and fyn, measured by immunoprecipitation further suggesting a physiological interaction between the two proteins. By weaker criteria for a PKC consensus site, fyn has 13 additional potential phosphorylation sites. Finally, it is further possible that PKC is a substrate for fyn, since there are 5 tyrosine residues in the V1 region; tyrosine-36 looks particularly reasonable in this regard.

The first PKC cognate binding protein discovered, RACK1, was a clear member of the WD40 family of proteins, characterized by having multiple tandem copies of a sequence of ~40 amino acids with a conserved WD pair towards the C-terminus. Fyn also has three repeats with weak WD40 homology (aa 51–270), beginning in the middle of the Unique region and ending early in the catalytic domain. At a more detailed level, RACK1 shares several other short sequences of homology with fyn, both in its regulatory and catalytic domains.

Sequence variation between three alternatively spliced human fyn forms is found between amino acids 242–270 (the end of the regulatory domain and the beginning of the catalytic domain, which includes the N-terminal of the third WD-40 repeat). Interestingly, the WD-40 motif landmarks are conserved in all the alternative spliced forms, including S-253, KD-257-258, and WEV 260-262.

Since fyn has an SH3 domain, other homologs of which are known to bind proline rich domains, it is noteworthy that PKC-theta has a moderately proline rich region of 50 residues (includes 10 prolines), accounting for a substantial part of the V3 region. Antibodies to the V3 region failed to immunoprecipitate fyn, suggesting that the antibody and fyn are binding in part to the same site. These results are not conclusive since the V3 region gave positive results in the two-hybrid system. Most other PKC isozymes do not contain proline rich regions, including the most closely related isozyme PKC-delta. The only other isozyme in which a moderately proline-rich domain is found is PKC-mu, a recently described member of the class with less overall PKC homology.

Figure 10A:
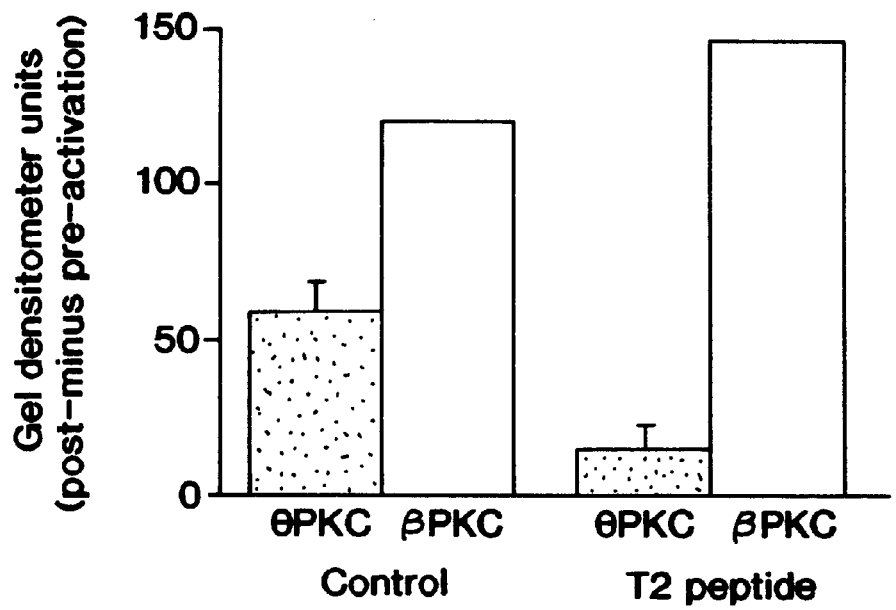
FIGS. 10A and 10B show that the T2 peptide (aa 36–46) from the V1 region of PKC-theta reduces translocation of PKC-theta, but not of PKC-beta, from the soluble to the particulate fraction after activation of Jurkat T-cells with PMA/PHA (panel A); peptide is taken up spontaneously from the medium in Jurkat T-cells. In parallel experiments, T2 peptide reduces expression of IL-2 as measured by ELISA in supernatant from stimulated cells (panel B).
Figure 10B:
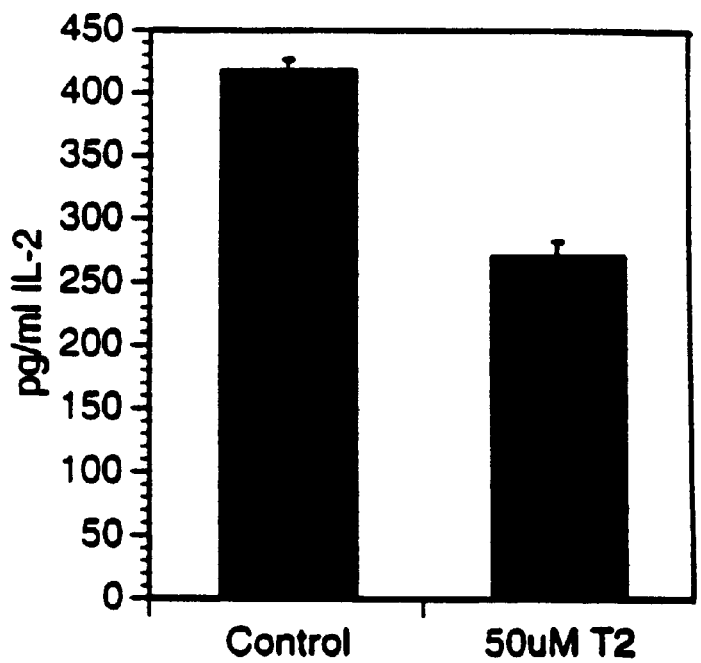

We have also observed that the T2 peptide, which blocks PKC-theta translocation as shown in FIG. 10A and hence blocks association with the cognate localization factor, causes measurable suppression of IL-2 production from activated Jurkat T-cells, FIG. 10B.

In summary, the key independent lines of evidence indicating that fyn is a physiologically relevant binding partner for PKC-theta in T-cells are: (i) a PKC-theta variable domain pulls fyn out of a cell extract in an affinity binding mode; (ii) antibodies to PKC-theta variable domain immunoprecipitate a complex of PKC and fyn from cell extracts; (iii) PKC-theta variable domains and fyn interact in the yeast two hybrid system. In all cases, appropriate controls using closely related proteins show specificity of the interaction.

The existence of cognate binding proteins has been previously described, as have methods for their identification and their utility in drug discovery (for example see Fields, U.S. Pat. No. 5,283,173 and U.S. Pat. No. 5,352,660). The actual identification of fyn as a partner for PKC-theta can now be used in such art-known methods to identify and isolate compounds which block fyn/PKC-theta interactions. Such agents can be used to modulate biological activities which are mediated by fyn/PKC-theta binding; these include activities associated with the immune system.

EXAMPLE 6

Assay for Immune Modulating Compounds Using PKC-theta Translocation as an Index

To assess translocation, suitable cells, preferably non-transformed human T-cells, are cultured to a density of $10^6$/ml and then incubated in cytokine-free medium for overnight. Ten-milliliter aliquots are used for each assay.

The substance to be tested is added to the appropriate samples and incubated for 15 minutes at 37° C. Substances known to stimulate the translocation of PKC-theta are then added: typically PMA at 20–80 nM±PHA at 1 $\mu$g/ml are added, and the culture is incubated for 15 minutes at 37° C.

After the incubation period, the samples are spun at 1000 rpm for 10 minutes and the cell pellet is washed with cold PBS. The cells are then resuspended in homogenization buffer and sonicated. They are then centrifuged at 55000 rpm for 30 minutes to obtain a supernatant cytosolic fraction and a pellet which is resuspended in homogenization buffer with a 27-gauge needle to obtain the particulate fraction. After normalization of total protein, the content of PKC in each of the supernatant and particulate fraction is then determined using SDS-PAGE and detection using appropriate antibodies.

Figure 11B:
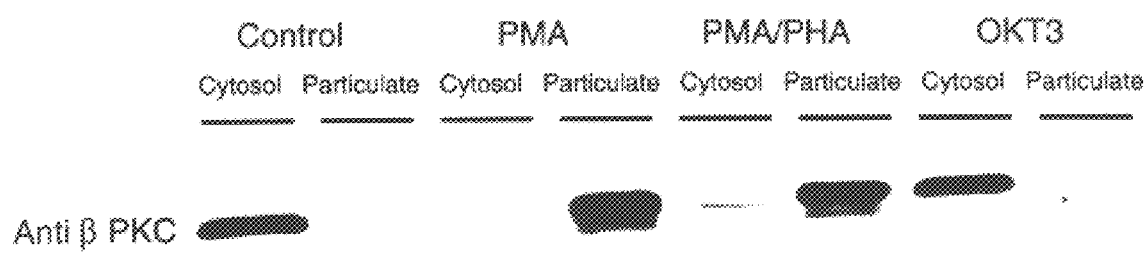

FIG. 11 shows the results of SDS-PAGE of the soluble and particulate fraction stained with anti-PKC-theta antibodies (FIG. 12A) or anti-PKC-beta antibodies (FIG. 12B). As shown, PKC-beta is essentially all in the soluble fraction in unstimulated cells, while PKC-theta is more or less evenly distributed between these two fractions. Presumably, this is the case because proliferation of these cells requires the presence of added cytokines, which may effect partial activation of the T-cells. When deprived of cytokines in the medium for, for example, overnight, the levels of PKC-theta in the soluble fraction are increased. In any case, after stimulation with either PMA or a combination of PMA/PHA, which directly cause PKC activation, both PKC-theta and PKC-beta are translocated to the particulate fraction. However, stimulation with OKT-3, an antibody immunoreactive with the CD3 component of T-cell receptors, which provides a more focused physiologically based activation, results in translocation of PKC-theta, but not PKC-beta. The ability of OKT-3 to effect, specifically, translocation of PKC-theta is further evidence of the involvement of PKC-theta in transduction of T-cell receptor mediated stimulation.

Figure 12:
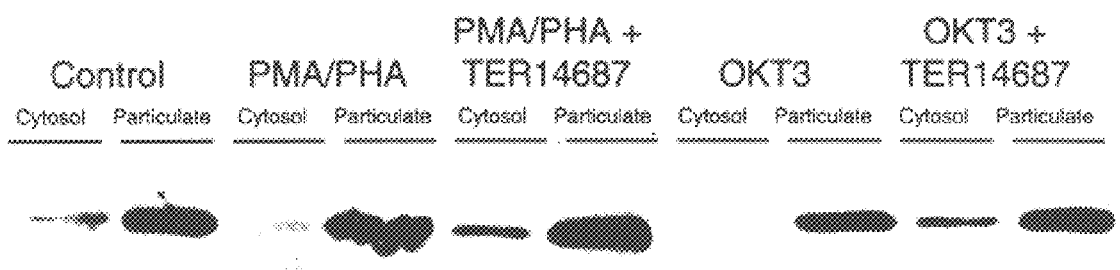
FIG. 12 is a photocopy of a blot which shows the effect of TER14687 on PKC-theta translocation.

The use of the foregoing as an assay for identifying an immune system modulator is shown in FIG. 12. In the assay conducted as described above, the cells were initially incubated with 20 $\mu$M of a candidate compound TER14687. As shown in FIG. 12, TER14687 was able to inhibit the translocation of PKC-theta to the particulate fraction when either OKT-3 or PMA/PHA was used as a stimulant. (The assay performed with OKT-3 involved one hour of incubation with OKT-3, rather than the 15-minute period described above.)

TER14687 was also shown to increase the proportion of PKC-theta in the soluble fraction in resting T-cells. T-cells are generally grown in the presence of exogenously added cytokines and are thus in a partially activated state. When cytokine stimulation is withdrawn for a period of time, PKC-theta concentration in the soluble fraction normally increases. TER14687 thus facilitates decay to the resting state.

The effect of TER14687 on the PKC-theta/cognate interaction can also be demonstrated by showing that TER14687 prevents tyrosine phosphorylation of a 21 kD protein after OKT-3 stimulation of T-cells, in which the foregoing protocol was followed except that phosphorylation was measured directly, with an Ab to phosphotyrosine. This phosphorylation is a known downstream event of T-cell activation.

EXAMPLE 7

Assay for Modulation Indexed by Binding

To visualize endogenous PKC cognates T-cell proteins are separated by SDS gel electrophoresis and transferred to nitrocellulose membranes. A large number of proteins are thus distributed on the nitrocellulose. The nitrocellulose is then incubated with PKC-theta and washed, and the bound PKC-theta is visualized using labeled anti-PKC-theta. PKC-theta protein was produced Sf9 insect cells using a baculovirus expression system, Invitrogen, San Diego, Calif. In the absence of substances known to activate PKC, essentially no bands appear. In the presence of PKC activators, a large number of bands is seen. Some of these bands may be true endogenous cognates; others may mimic cognate binding abilities in the denatured state characteristic of proteins transferred to nitrocellulose membranes. As such, these proteins are substitutes for the endogenous cognates.

In the presence of TERI4687 during PKC-theta incubation on the blot, binding is diminished, thus showing the modulating effect of TER14687 on cognate binding.

In addition to TER14687, the following peptides derived from the regulatory region of fyn were tested: fyn2, representing residues 111–118 underlined in FIG. 9, showed partial inhibition of PKC-theta binding to fyn; and fyn3, residues 188–195 underlined in FIG. 9, showed complete inhibition of PKC binding. fyn2 and fyn3 are derived from the portion of fyn which shows homology to WD40 repeats. An additional peptide, fyn1 was not capable of inhibiting binding; this peptide was derived from a fyn splice variant different from that shown in FIG. 9. Another inactive peptide was fyn4, representing residues 441–449 from the catalytic domain.

EXAMPLE 8

Additional Cognates Identified by the Yeast Two-Hybrid System

The intracellular method to detect peptide/peptide binding, described in Example 5 hereinabove was used a) to find additional peptides which bind to PKC-theta and b) to provide an assay system for the effect of candidate substances on interaction with PKC-theta and its cognate.

First, the yeast two-hybrid system was used to retrieve cDNAs encoding peptides that interact with PKC-theta.

In this approach, plasmids containing the polymerase activating domain fused to the kinase or regulatory domains of fyn were mixed with similar vectors containing a cDNA library from the murine T-cell line HT2 in a ratio of 1:500. Yeast harboring plasmids containing PKC-theta V1 fused to the DNA binding domain were transformed with this mixture of plasmids at one-tenth of the regular protocol. The yeast were plated onto media selecting for presence of the plasmids (THULL) plates and assayed for β-galactosidase on filter lifts. Positive colonies were picked on THULL grids and retested. DNA was extracted from colonies which remained positive, and then amplified using 5' and 3' plasmid-based polylinker flanking primers and the products were analyzed by Southern blot using fyn as a probe.

Of 12 positives found when fyn kinase domain was mixed into the cDNA library, 10 were the fyn kinase itself However, two contained sequences other than those derived from fyn.

Of six positives obtained from the mixture when the cDNA library had been mixed with the fyn regulatory domain, three contained DNA sequences other than fyn. Two of these, designated 2-10 and 2-40 have identical nucleotide sequences not yet identified with any known sequence and the other, 2-32 appears to be a mouse homolog of a recently isolated human gene, ELL. The cDNA insert in 2-10 and 2-40 contained 1083 base pairs with an open reading frame encoding a previously unknown 335 amino acid peptide with several potential zinc-finger motifs. The cDNA hybridizes with a 2.4 kD transcript present in lymphoid tissue and a 6 kD transcript present in heart and skeletal muscle as shown by Northern blot.

Both clones 2-10 and 2-32, when tested in a liquid β-gal assay, were able to interact with PKC-theta V1 in the two-hybrid system described above. When transformed into the parental yeast strain L40, lacking PKC-theta V1, no activation was observed by a reporter assay, nor was activation observed when theta V1 was replaced by delta V1 or an unrelated protein, lamin.

Figure 13:
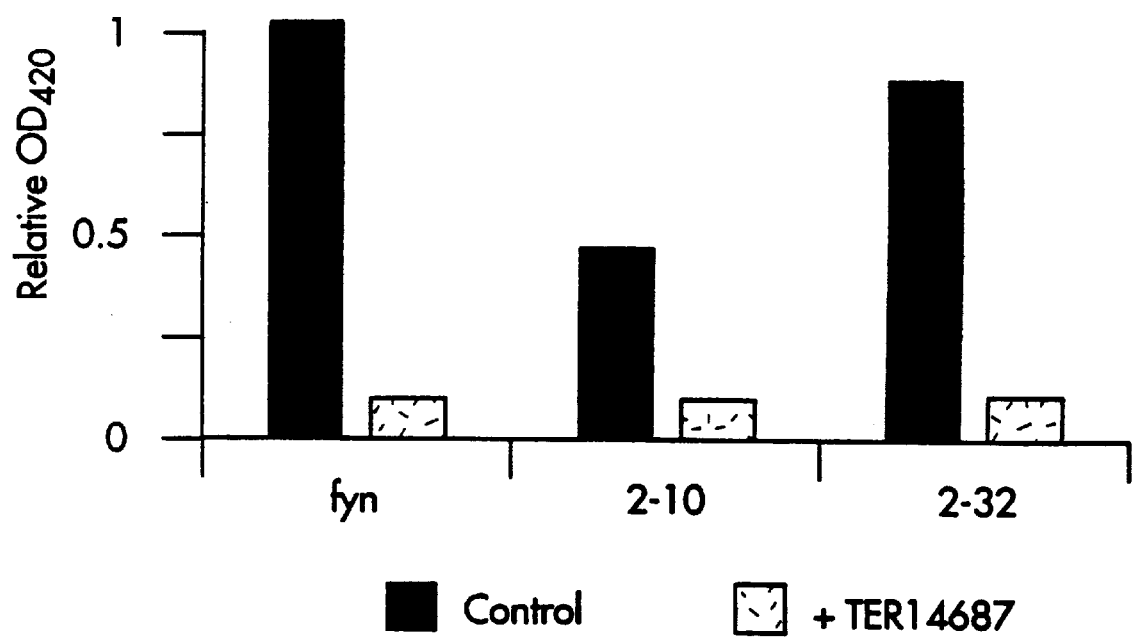
FIG. 13 shows the results of binding of peptides encoded by the fyn kinase domains and two surrogates, clones 2-10 and 2-32, to PKC-theta V1 in the absence or presence of TER14687 using a two-hybrid system assay.

Using the same assay, the effect of TER14687 on the interaction of PKC-theta V1 with either fyn or with clones 2-10 and 2-32 was tested. In this assay, yeast containing the above-described two-hybrid system were inoculated 1: 10 dilutions into 1 ml THULL containing 40 μM TER14687 or a control compound in DMSO. Various other controls were included; for example, TER14687 did not inhibit expression of the reporter gene when the transcription factor (LexA/ E2A) was supplied in covalently bound form. The activity of β-galactosidase produced was measured as OD at 420 nm. TER14687 markedly diminished binding theta V1 to fyn or the substitute cognates generated from 2-10 and 2-32, as shown in FIG. 13.

In addition, several clones encoding apparent cognate proteins were obtained from a human's CD4$^+$ T-cell cDNA library using the same yeast two-hybrid protocol. The cDNA library was constructed using T-cells isolated from donor blood and had a complexity estimated between $10^5$ to $5 \times 10^6$ independent clones. Out of $1.4 \times 10^7$ clones screened, 63 remained positive after a secondary βGAL filterlift assay.

Thirty-nine of the clones appear to have identical sequence and the same approximate cDNA insert size. The sequence contains an open reading frame and is clearly a partial sequence which does not match any data base sequence. One of these clones, No. 10, was retested in the yeast two-hybrid system and found to bind θV1, but not δV1 or lamin.

In addition, two clones from this library, 1-22 and 1-23 share sequence with human elongation factor 1-γ. 1-23 overlaps with 1-22, but both are partial sequences. Both bind specifically to θV1 in the yeast two-hybrid assay.

One additional clone, 2-18 also shows specific binding to θV1 in the yeast two-hybrid assay and shows high homology with SH3-containing c-abl binding proteins which inhibit c-abl transformation. U17698 murine abl philin-1 is 89% homologous; U31089 human Abl binding protein 3 is 94% homologous; and U23435 human Abl interactor 2 is 88% homologous.

Two additional clones were obtained in a similar manner. Clone 2-20 contains 729 bp as a partial cDNA matched to human elongation factor 2. Clone 3-1 contains 839 bp with high homology to HSV1 transducing factor α.

The nucleotide sequences and the amino acid sequences encoded for clones 2-10, 2-32, #10, 1-22, 2-18, 2-20 and 3-1 are shown in FIG. 15.

EXAMPLE 9

Association of PKC-theta Activation with Allergic Reactions

A human T-cell line, TT7.5, is physiologically activated with OKT3 coated on tissue culture plates at 10 μg/ml as shown by enhanced proliferation using a tritiated thymidine assay. Activation is also characterized by enhanced secretion of interferon-γ, and of interleukins 4 and 5, but not of IL-2, as assayed in appropriate ELISAs. This pattern characterizes a Th2-like cell. Th2 cells have been shown to mediate allergy via the immunoregulatory effects of IL-4 and IL-5 and can thus be used as an in vitro model of T-cell function in mediating allergy.

As was shown above, OKT3 stimulation of T-cell lines, including TT7.5 cells, results in translocation of PKC-theta.

Figure 14A:
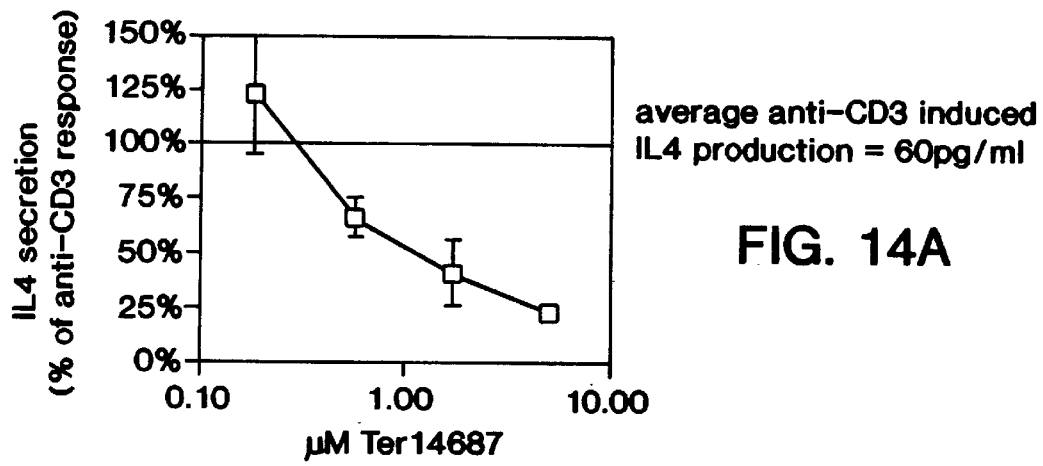
FIG. 14 shows the effect of TER14687 on anti-CD3-induced production of IL4, IL5 and γIFN.
Figure 14B:
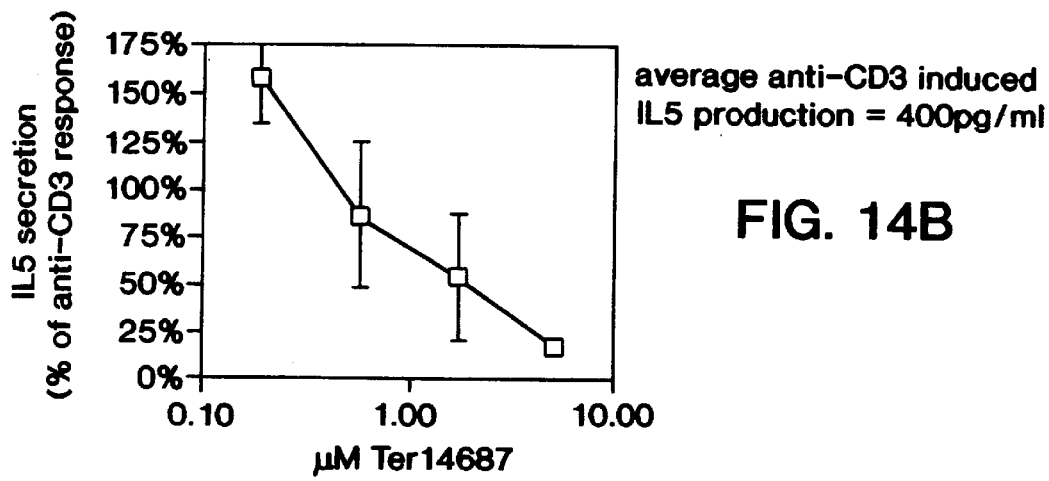
Figure 14C:
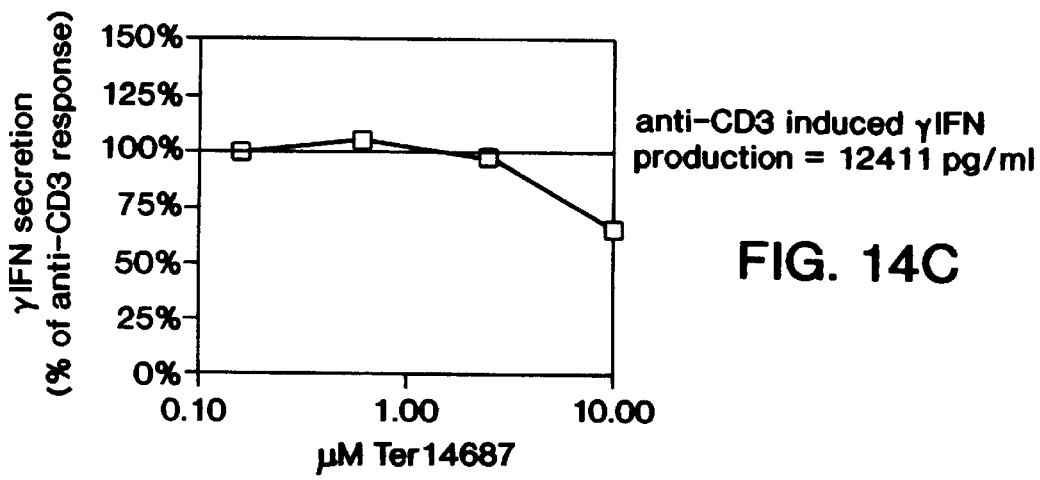

In a similar assay that uses cytokine production as a measure of PKC-theta interaction with cognate, TER14687, administered during OKT3 activation, inhibits the production of IL-4 and IL-5, but not the induced production of interferon-γ, as shown in FIG. 14. This pattern of cytokine production is associated with reduced stimulation of IgE and eosinophil production. Similar results are obtained with the Th2-like T-cell line TT3.6. In a Th1-type cell line (TT6.4) TER14687 inhibits OKT3-induced IL-2 production, but not interferon-γ production.

TER14687 also strongly inhibits expression, in TT7.5 cells, of the surface markers of T-cell activation, such as CD69, CD25 and CD40L following overnight OKT3 stimulation. CD69 is expressed exclusively on activated T-cells, CD25 is a low-affinity IL-2 receptor expressed on activated T-cells and CD40L is a ligand for CD40 which is also expressed exclusively on activated T-cells. These markers were assayed using appropriately labeled fluorescent antibodies and a flow cytometer.

Similar results were obtained in Jurkat cells following activation by PMA rather than OKT3. In the presence of 50 μM fyn2 peptide, enhanced expression of CD69 is reduced.

We claim:

1. A method to identify a substance that has immunomodulating activity which method comprises providing an environment containing PKC-theta or a fragment thereof and a cognate of said PKC-theta under conditions wherein said PKC-theta or fragment interacts with said cognate;

adding a candidate substance to said environment;

determining the interaction of PKC-theta or fragment with cognate in the presence and absence of said candidate;

comparing said interaction in presence and absence of candidate;

wherein a candidate which modulates said interaction is identified as having immunomodulating activity, and wherein said cognate is selected from the group consisting of fyn; the fyn fragment fyn-3; the fyn fragment fyn-2; the protein encoded by clone 2-10 (SEQ ID NO:3); the protein encoded by clone 2-32 (SEQ ID NO:5); and a protein which inhibits the binding of fyn to PKC-theta.

2. The method of claim 1 wherein said environment is an intracellular environment.

3. The method of claim 2 wherein determining said interaction is by measuring translocation of said PKC-theta or fragment.

4. The method of claim 2 wherein determining said interaction is by measuring tyrosine phosphorylation of a 21 kD protein after OKT-3 stimulation of T-cells.

5. The method of claim 2 wherein determining said interaction is by measuring diminution of IL4 and/or IL5 production without affecting IFNγ production.

6. The method of claim 1 wherein determining said interaction comprises determining binding of said PKC-theta or fragment to its cognate.

7. The method of claim 6 wherein said environment is an intracellular environment.

8. The method of claim 7 wherein said binding is determined by means of a "two-hybrid" system as defined herein.

* * * * *

SEQUENCE LISTING (1) GENERAL INFORMATION:

(iii) NUMBER OF SEQUENCES: 89

(2) INFORMATION FOR SEQ ID NO:1:

(i) SEQUENCE CHARACTERISTICS:
      (A) LENGTH: 532 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: CDS
      (B) LOCATION: 1..1002

(xi) SEQUENCE DESCRIPTION: SEQ ID NO:1:

```
Met Gly Cys Val Gln Cys Lys Asp Lys Glu Ala Ala Lys Leu Thr Glu
1               5                   10                  15

Glu Arg Asp Gly Ser Leu Asn Gln Ser Ser Gly Tyr Arg Tyr Gly Thr
            20                  25                  30

Asp Pro Thr Pro Gln His Tyr Pro Ser Phe Gly Val Thr Ser Ile Pro
        35                  40                  45

Asn Tyr Asn Asn Phe His Ala Ala Gly Gly Gln Gly Leu Thr Val Phe
    50                  55                  60

Gly Gly Val Asn Ser Ser Ser His Thr Gly Thr Leu Arg Thr Arg Gly
65                  70                  75                  80

Gly Thr Gly Val Thr Leu Phe Val Ala Leu Tyr Asp Tyr Ala Arg Thr
                85                  90                  95

Glu Asp Asp Leu Ser Phe His Lys Gly Glu Lys Phe Gln Ile Leu Asn
            100                 105                 110

Ser Ser Glu Gly Asp Trp Trp Glu Ala Arg Ser Leu Thr Thr Gly Glu
        115                 120                 125

Thr Gly Tyr Ile Pro Ser Asn Tyr Val Ala Pro Val Asp Ser Ile Gln
    130                 135                 140
```

```
Ala Glu Glu Trp Tyr Phe Gly Lys Leu Gly Arg Lys Asp Ala Glu Arg
145                 150                 155                 160

Gln Leu Leu Ser Phe Gly Asn Pro Arg Gly Thr Phe Leu Ile Arg Glu
            165                 170                 175

Ser Gln Thr Thr Lys Gly Ala Tyr Ser Leu Ser Ile Arg Asp Trp Asp
            180                 185                 190

Asp Met Lys Gly Asp His Val Lys His Tyr Lys Ile Arg Lys Leu Asp
        195                 200                 205

Asn Gly Gly Tyr Tyr Ile Thr Thr Arg Ala Gln Glu Thr Leu Gln Gln
    210                 215                 220

Leu Val Gln His Tyr Ser Glu Lys Ala Asp Gly Leu Cys Phe Asn Leu
225                 230                 235                 240

Thr Val Ile Ala Ser Ser Cys Thr Pro Gln Thr Ser Gly Leu Ala Lys
                245                 250                 255

Asp Ala Trp Glu Val Ala Arg Arg Ser Leu Cys Leu Glu Lys Lys Leu
                260                 265                 270

Gly Gln Gly Cys Phe Ala Glu Val Trp Leu Gly Thr Trp Asn Gly Asn
            275                 280                 285

Thr Lys Val Ala Ile Lys Thr Leu Lys Pro Gly Thr Met Ser Pro Glu
    290                 295                 300

Ser Phe Leu Glu Glu Ala Gln Ile Met Lys Lys Leu Lys His Asp Lys
305                 310                 315                 320

Leu Val Gln Leu Tyr Ala Val Val Ser Glu Glu Pro Ile Tyr Ile Val
                325                 330                 335

Thr Glu Tyr Met Ser Lys Gly Ser Leu Leu Asp Phe Leu Lys Asp Gly
                340                 345                 350

Glu Gly Arg Ala Leu Lys Leu Pro Asn Leu Val Asp Met Ala Ala Gln
            355                 360                 365

Val Ala Ala Gly Met Ala Tyr Ile Glu Arg Met Asn Tyr Ile His Arg
    370                 375                 380

Asp Leu Arg Ser Ala Asn Ile Leu Val Gly Asn Gly Leu Ile Cys Lys
385                 390                 395                 400

Ile Ala Asp Phe Gly Leu Ala Arg Leu Ile Glu Asp Asn Glu Tyr Thr
                405                 410                 415

Ala Arg Gln Gly Ala Lys Phe Pro Ile Lys Trp Thr Ala Pro Glu Ala
            420                 425                 430

Ala Leu Tyr Gly Arg Phe Thr Ile Lys Ser Asp Val Trp Ser Phe Gly
            435                 440                 445

Ile Leu Leu Thr Glu Leu Val Thr Lys Gly Arg Val Pro Tyr Pro Gly
450                 455                 460

Met Asn Asn Arg Glu Val Leu Glu Gln Val Glu Arg Gly Tyr Arg Met
465                 470                 475                 480

Pro Cys Pro Gln Asp Cys Pro Ile Ser Leu His Glu Leu Met Ile His
                485                 490                 495

Cys Trp Lys Lys Asp Pro Glu Glu Arg Pro Thr Phe Glu Tyr Leu Gln
            500                 505                 510

Gly Phe Leu Glu Asp Tyr Phe Thr Ala Thr Glu Pro Gln Tyr Gln Pro
        515                 520                 525

Gly Glu Asn Leu
    530
```

(2) INFORMATION FOR SEQ ID NO:2:

(i) SEQUENCE CHARACTERISTICS:
        (A) LENGTH: 1007 base pairs (B) TYPE: nucleic acid
(C) STRANDEDNESS: double
(D) TOPOLOGY: linear (ii) MOLECULE TYPE: DNA (genomic)

(ix) FEATURE:
  (A) NAME/KEY: CDS
  (B) LOCATION: 1..1002

(xi) SEQUENCE DESCRIPTION: SEQ ID NO:2:

| | | | | | | | | | | | | | | | | |
|---|---|---|---|---|---|---|---|---|---|---|---|---|---|---|---|---|
| GCC | TCA | GCA | CAG | CCC | TTC | CTC | TGC | TGC | CTG | TGC | GGT | ATG | ATC | TTT | CCT | 48 |
| Ala | Ser | Ala | Gln | Pro | Phe | Leu | Cys | Cys | Leu | Cys | Gly | Met | Ile | Phe | Pro | |
| 1 | | | | 5 | | | | | 10 | | | | | 15 | | |
| GGG | AGG | ACT | GGC | TAC | AGG | CGT | CAT | CTG | CGC | CAG | GCT | CAT | GGA | GCT | TCT | 96 |
| Gly | Arg | Thr | Gly | Tyr | Arg | Arg | His | Leu | Arg | Gln | Ala | His | Gly | Ala | Ser | |
| | | | 20 | | | | | 25 | | | | | 30 | | | |
| GCC | ATG | ACT | GAG | GGC | TCA | GAA | GAA | GAG | GAA | GGC | ACA | GCA | GAA | ACA | | 144 |
| Ala | Met | Thr | Glu | Gly | Ser | Glu | Glu | Glu | Glu | Gly | Thr | Ala | Glu | Thr | | |
| | | 35 | | | | | 40 | | | | | 45 | | | | |
| GCC | TCT | ACC | CAT | AGT | CCT | CCC | CTG | CAA | CTC | TCA | GAA | GCA | GAG | CTG | CTG | 192 |
| Ala | Ser | Thr | His | Ser | Pro | Pro | Leu | Gln | Leu | Ser | Glu | Ala | Glu | Leu | Leu | |
| | 50 | | | | | 55 | | | | | 60 | | | | | |
| AAT | CAA | CTG | CAG | CGT | GAG | GTG | GAA | GCT | CTA | GAT | GGA | GCA | GGT | TAT | GGT | 240 |
| Asn | Gln | Leu | Gln | Arg | Glu | Val | Glu | Ala | Leu | Asp | Gly | Ala | Gly | Tyr | Gly | |
| 65 | | | | | 70 | | | | | 75 | | | | | 80 | |
| CAT | ATT | TGT | GGT | TGC | TGT | GGT | CAG | ACC | TAT | GAT | GAC | CTG | GGG | AGC | CTG | 288 |
| His | Ile | Cys | Gly | Cys | Cys | Gly | Gln | Thr | Tyr | Asp | Asp | Leu | Gly | Ser | Leu | |
| | | | | 85 | | | | | 90 | | | | | 95 | | |
| GAG | CGT | CAC | CAC | CAA | AGT | CAA | AGT | TCT | AGC | AAT | AGG | ACA | GAG | AAT | GTT | 336 |
| Glu | Arg | His | His | Gln | Ser | Gln | Ser | Ser | Ser | Asn | Arg | Thr | Glu | Asn | Val | |
| | | | 100 | | | | | 105 | | | | | 110 | | | |
| CCT | AGC | CAT | TTG | GAA | GGA | GCA | GGT | GAT | GCA | ACA | GAA | ATG | GTT | GCA | GAT | 384 |
| Pro | Ser | His | Leu | Glu | Gly | Ala | Gly | Asp | Ala | Thr | Glu | Met | Val | Ala | Asp | |
| | | 115 | | | | | 120 | | | | | 125 | | | | |
| CAT | GGC | TTT | GAG | GGC | ACA | GTG | ACC | TCC | GTC | TCA | GAA | GAA | GGT | GGG | GAC | 432 |
| His | Gly | Phe | Glu | Gly | Thr | Val | Thr | Ser | Val | Ser | Glu | Glu | Gly | Gly | Asp | |
| | 130 | | | | | 135 | | | | | 140 | | | | | |
| ATA | AAG | TCT | GAA | GAG | GGA | GTA | GGT | GGC | ACA | GTT | GCA | GAC | AGC | CTT | TGC | 480 |
| Ile | Lys | Ser | Glu | Glu | Gly | Val | Gly | Gly | Thr | Val | Ala | Asp | Ser | Leu | Cys | |
| 145 | | | | | 150 | | | | | 155 | | | | | 160 | |
| ATG | CAG | GCT | GGT | GAA | AGC | TTT | CTG | GAG | TCC | CAC | CCT | CGC | CCT | TTC | CAA | 528 |
| Met | Gln | Ala | Gly | Glu | Ser | Phe | Leu | Glu | Ser | His | Pro | Arg | Pro | Phe | Gln | |
| | | | | 165 | | | | | 170 | | | | | 175 | | |
| TGT | AAC | CAG | TGT | GGC | AAG | ACC | TAT | CGC | CAC | GGA | GGC | AGC | TTG | GTA | AAC | 576 |
| Cys | Asn | Gln | Cys | Gly | Lys | Thr | Tyr | Arg | His | Gly | Gly | Ser | Leu | Val | Asn | |
| | | | 180 | | | | | 185 | | | | | 190 | | | |
| CAC | CGA | AAG | ATC | CAC | CAG | ACA | GGT | GAT | TTC | ATC | TGT | CCT | GTC | TGT | TCC | 624 |
| His | Arg | Lys | Ile | His | Gln | Thr | Gly | Asp | Phe | Ile | Cys | Pro | Val | Cys | Ser | |
| | | 195 | | | | | 200 | | | | | 205 | | | | |
| CGC | TGC | TAC | CCC | AAT | CTG | GCT | GCC | TAC | CGG | AAT | CAT | CTG | CGG | AAT | CAC | 672 |
| Arg | Cys | Tyr | Pro | Asn | Leu | Ala | Ala | Tyr | Arg | Asn | His | Leu | Arg | Asn | His | |
| | 210 | | | | | 215 | | | | | 220 | | | | | |
| CCT | CGC | TGC | AAA | GGC | TCA | GAG | CCC | CAA | ATG | GGG | CCC | ATC | TCA | GAA | GCA | 720 |
| Pro | Arg | Cys | Lys | Gly | Ser | Glu | Pro | Gln | Met | Gly | Pro | Ile | Ser | Glu | Ala | |
| 225 | | | | | 230 | | | | | 235 | | | | | 240 | |
| GGA | GGC | TGC | AGT | GAG | CCC | CAG | AAT | GCA | GCA | GAG | GCA | GGG | CAG | GAG | CAG | 768 |
| Gly | Gly | Cys | Ser | Glu | Pro | Gln | Asn | Ala | Ala | Glu | Ala | Gly | Gln | Glu | Gln | |
| | | | | 245 | | | | | 250 | | | | | 255 | | |
| GCT | GTC | ATA | GGG | CAA | CTC | CAG | GAA | GAG | CTT | AAA | GTG | GAG | CCC | TTG | GAG | 816 |
| Ala | Val | Ile | Gly | Gln | Leu | Gln | Glu | Glu | Leu | Lys | Val | Glu | Pro | Leu | Glu | |
| | | | 260 | | | | | 265 | | | | | 270 | | | |

```
GAG CTG GCA GGT GTC AAA GAA GAA GTG TGG GAG GGG ACC GCT GTA AAG       864
Glu Leu Ala Gly Val Lys Glu Glu Val Trp Glu Gly Thr Ala Val Lys
        275                 280                 285

GAA GAG GAG CTG GAG CAG GAG TTG GAG ACA GGC TGT CAG ACT GAG GTC       912
Glu Glu Glu Leu Glu Gln Glu Leu Glu Thr Gly Cys Gln Thr Glu Val
        290                 295                 300

ACC TCG GAG CGG CCC TTT AGC TGT GAA GTG TGT GGC CGC ACC TAC AAG       960
Thr Ser Glu Arg Pro Phe Ser Cys Glu Val Cys Gly Arg Thr Tyr Lys
305                 310                 315                 320

CAT GCT GGC AGC CTT ATC AAT CAC CGG CAG AGC CAC CAG ACT              1002
His Ala Gly Ser Leu Ile Asn His Arg Gln Ser His Gln Thr
                325                 330

GGCCA                                                                1007
```

(2) INFORMATION FOR SEQ ID NO:3:

(i) SEQUENCE CHARACTERISTICS:
        (A) LENGTH: 334 amino acids
        (B) TYPE: amino acid
        (D) TOPOLOGY: linear (ii) MOLECULE TYPE: protein (xi) SEQUENCE DESCRIPTION: SEQ ID NO:3:

```
Ala Ser Ala Gln Pro Phe Leu Cys Cys Leu Cys Gly Met Ile Phe Pro
1               5                   10                  15

Gly Arg Thr Gly Tyr Arg Arg His Leu Arg Gln Ala His Gly Ala Ser
                20                  25                  30

Ala Met Thr Glu Gly Ser Glu Glu Glu Gly Thr Ala Glu Thr
            35                  40                  45

Ala Ser Thr His Ser Pro Pro Leu Gln Leu Ser Glu Ala Glu Leu Leu
        50                  55                  60

Asn Gln Leu Gln Arg Glu Val Glu Ala Leu Asp Gly Ala Gly Tyr Gly
65                  70                  75                  80

His Ile Cys Gly Cys Cys Gly Gln Thr Tyr Asp Asp Leu Gly Ser Leu
                85                  90                  95

Glu Arg His His Gln Ser Gln Ser Ser Ser Asn Arg Thr Glu Asn Val
                100                 105                 110

Pro Ser His Leu Glu Gly Ala Gly Asp Ala Thr Glu Met Val Ala Asp
            115                 120                 125

His Gly Phe Glu Gly Thr Val Thr Ser Val Ser Glu Glu Gly Gly Asp
        130                 135                 140

Ile Lys Ser Glu Glu Gly Val Gly Gly Thr Val Ala Asp Ser Leu Cys
145                 150                 155                 160

Met Gln Ala Gly Glu Ser Phe Leu Glu Ser His Pro Arg Pro Phe Gln
                165                 170                 175

Cys Asn Gln Cys Gly Lys Thr Tyr Arg His Gly Gly Ser Leu Val Asn
            180                 185                 190

His Arg Lys Ile His Gln Thr Gly Asp Phe Ile Cys Pro Val Cys Ser
        195                 200                 205

Arg Cys Tyr Pro Asn Leu Ala Ala Tyr Arg Asn His Leu Arg Asn His
    210                 215                 220

Pro Arg Cys Lys Gly Ser Glu Pro Gln Met Gly Pro Ile Ser Glu Ala
225                 230                 235                 240

Gly Gly Cys Ser Glu Pro Gln Asn Ala Ala Glu Ala Gly Gln Glu Gln
                245                 250                 255

Ala Val Ile Gly Gln Leu Gln Glu Glu Leu Lys Val Glu Pro Leu Glu
            260                 265                 270
```

```
Glu Leu Ala Gly Val Lys Glu Val Trp Glu Gly Thr Ala Val Lys
            275                 280                 285

Glu Glu Glu Leu Glu Gln Glu Leu Glu Thr Gly Cys Gln Thr Glu Val
290                 295                 300

Thr Ser Glu Arg Pro Phe Ser Cys Glu Val Cys Gly Arg Thr Tyr Lys
305                 310                 315                 320

His Ala Gly Ser Leu Ile Asn His Arg Gln Ser His Gln Thr
                325                 330

(2) INFORMATION FOR SEQ ID NO:4:

(i) SEQUENCE CHARACTERISTICS:
        (A) LENGTH: 1294 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1293

(xi) SEQUENCE DESCRIPTION: SEQ ID NO:4:

GGA AGC CAA GGG CAC ATC TCT ATA CCC CAG CCT GAC TGC CCA GAG GAG         48
Gly Ser Gln Gly His Ile Ser Ile Pro Gln Pro Asp Cys Pro Glu Glu
335                 340                 345                 350

GTG CGG GCC TTC TCC TTC TAC CTC TCC AAT ATT GGC CGC GAC AGC CCT         96
Val Arg Ala Phe Ser Phe Tyr Leu Ser Asn Ile Gly Arg Asp Ser Pro
                355                 360                 365

CAG GGC AGC TTT GAT TGC ATC CAA CAA TAT GTA TCC AGC TAT GGG GAT        144
Gln Gly Ser Phe Asp Cys Ile Gln Gln Tyr Val Ser Ser Tyr Gly Asp
            370                 375                 380

GTA CAC CTG GAC TGC CTG GGC AGC ATC CAG GAC AAG GTC ACG GTG TGT        192
Val His Leu Asp Cys Leu Gly Ser Ile Gln Asp Lys Val Thr Val Cys
        385                 390                 395

GCT ACT GAT GAC TCC TAC CAG AAA GCA CGA CAG AGC ATG GCA CAG GCA        240
Ala Thr Asp Asp Ser Tyr Gln Lys Ala Arg Gln Ser Met Ala Gln Ala
    400                 405                 410

GAG GAG GAG ACT CGG AGC CGA AGT GCC ATC GTC ATT AAG GCT GGA GGC        288
Glu Glu Glu Thr Arg Ser Arg Ser Ala Ile Val Ile Lys Ala Gly Gly
415                 420                 425                 430

CGA TAC ATG GGG AAA AAG GTT CAG TTT CGG AAG CCA GCG CCA GGG GCA        336
Arg Tyr Met Gly Lys Lys Val Gln Phe Arg Lys Pro Ala Pro Gly Ala
                435                 440                 445

GCT GAT GCA GTA CCC TCC CGG AAG CGT GCT ACC CCC ATT AAC CTG GCA        384
Ala Asp Ala Val Pro Ser Arg Lys Arg Ala Thr Pro Ile Asn Leu Ala
            450                 455                 460

AGT GCC ATC AGA AAG AGC AGT GGG AGT GGA GCC AGC AGT GTG GTA CAG        432
Ser Ala Ile Arg Lys Ser Ser Gly Ser Gly Ala Ser Ser Val Val Gln
        465                 470                 475

AGG CCC TTC CGA GAT CGG GTG CTA CAC CTC CTG GCC CTG AGG CCC TAC        480
Arg Pro Phe Arg Asp Arg Val Leu His Leu Leu Ala Leu Arg Pro Tyr
    480                 485                 490

AGG AAG GCT GAG CTG CTG CTG CGG TTG CAG AAG GAT GGG TTG ACA CAG        528
Arg Lys Ala Glu Leu Leu Leu Arg Leu Gln Lys Asp Gly Leu Thr Gln
495                 500                 505                 510

GCA GAC AAG GAC ACC CTG GAC AGC CTG CTG CAG CAG GTG GCC AGT GTG        576
Ala Asp Lys Asp Thr Leu Asp Ser Leu Leu Gln Gln Val Ala Ser Val
                515                 520                 525

AAC CCC AAG GAT GGC ACG TGC ACG CTG CAG GAC TGC ATG TAC AAA AGC        624
Asn Pro Lys Asp Gly Thr Cys Thr Leu Gln Asp Cys Met Tyr Lys Ser
```

```
                      530                  535                  540
CTG CAG AAG GAC TGG CCC GGC TAC TCT GAG GGG GAC CGG CAG CTG CTG           672
Leu Gln Lys Asp Trp Pro Gly Tyr Ser Glu Gly Asp Arg Gln Leu Leu
            545                  550                  555

AAG CGC ATG CTC ATG CGG AAG CTG TGT CAG CCA CAG AAT GCC ACT ACA           720
Lys Arg Met Leu Met Arg Lys Leu Cys Gln Pro Gln Asn Ala Thr Thr
        560                  565                  570

GAC TCC AGC CCG CCC CGA GAG CAT GGA CGC TCT GCC TCA CCC TCT CAG           768
Asp Ser Ser Pro Pro Arg Glu His Gly Arg Ser Ala Ser Pro Ser Gln
575                  580                  585                  590

AAA CGG CGT ACA GAC TTC ATT GAC CCC CTG GCC AGC AAG AAG CCC CGG           816
Lys Arg Arg Thr Asp Phe Ile Asp Pro Leu Ala Ser Lys Lys Pro Arg
                595                  600                  605

ATC TCA CAT TTC ACA CAG CGA GCA CAA CCC ACC CTC AAT GGC AAA CTG           864
Ile Ser His Phe Thr Gln Arg Ala Gln Pro Thr Leu Asn Gly Lys Leu
            610                  615                  620

GGT GCC CCC AAT GGC CAT GAG ACA CTG CTG CCT GTT CCA GGA CCC ACC           912
Gly Ala Pro Asn Gly His Glu Thr Leu Leu Pro Val Pro Gly Pro Thr
        625                  630                  635

CCA TCA GAC ACC TTC AGC TCT AGC CAT CTG CCC CCA CGG CTG GAG CCC           960
Pro Ser Asp Thr Phe Ser Ser Ser His Leu Pro Pro Arg Leu Glu Pro
640                  645                  650

CCA AGG ACC CAC GAC CCC CTA GCT GAT GTC AGT AAT GAC CTA GGT CAC          1008
Pro Arg Thr His Asp Pro Leu Ala Asp Val Ser Asn Asp Leu Gly His
655                  660                  665                  670

AGT ACC CAG GAC TAC AAG CAC CAG GAA GCC ACC CCA GCT CCA GCA CCC          1056
Ser Thr Gln Asp Tyr Lys His Gln Glu Ala Thr Pro Ala Pro Ala Pro
                675                  680                  685

CAT TTT GGT CTT CCC CTG CTG ACG GAC TTT CCT CAG GGT GAG CAA CCT          1104
His Phe Gly Leu Pro Leu Leu Thr Asp Phe Pro Gln Gly Glu Gln Pro
            690                  695                  700

ATT AGT TCC TCA CAC ACC CAC AGC CGA CCC AAG AAG AAG TCC AAG AAG          1152
Ile Ser Ser Ser His Thr His Ser Arg Pro Lys Lys Lys Ser Lys Lys
        705                  710                  715

CAC AAA GAC AAG GAG CGG CCC CCT GAA GAA AGG CCC CCC GCC CCA CAG          1200
His Lys Asp Lys Glu Arg Pro Pro Glu Glu Arg Pro Pro Ala Pro Gln
720                  725                  730

CCT GAT GCA CCT ACT GCC CCT GCA CTA CCG CCA GAT GCC CCA GGT CTG          1248
Pro Asp Ala Pro Thr Ala Pro Ala Leu Pro Pro Asp Ala Pro Gly Leu
735                  740                  745                  750

AAT GGA GCC TGT GAC AAT GAA CCC ACA TCC TTG TCA GAG ACC CCG               1293
Asn Gly Ala Cys Asp Asn Glu Pro Thr Ser Leu Ser Glu Thr Pro
                755                  760                  765

G                                                                        1294
```

(2) INFORMATION FOR SEQ ID NO:5:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:5:

```
Gly Ser Gln Gly His Ile Ser Ile Pro Gln Pro Asp Cys Pro Glu Glu
1               5                  10                  15

Val Arg Ala Phe Ser Phe Tyr Leu Ser Asn Ile Gly Arg Asp Ser Pro
                20                  25                  30

Gln Gly Ser Phe Asp Cys Ile Gln Gln Tyr Val Ser Ser Tyr Gly Asp
            35                  40                  45
```

```
Val His Leu Asp Cys Leu Gly Ser Ile Gln Asp Lys Val Thr Val Cys
    50                  55                  60

Ala Thr Asp Asp Ser Tyr Gln Lys Ala Arg Gln Ser Met Ala Gln Ala
 65                  70                  75                  80

Glu Glu Glu Thr Arg Ser Arg Ser Ala Ile Val Ile Lys Ala Gly Gly
                 85                  90                  95

Arg Tyr Met Gly Lys Lys Val Gln Phe Arg Lys Pro Ala Pro Gly Ala
                100                 105                 110

Ala Asp Ala Val Pro Ser Arg Lys Arg Ala Thr Pro Ile Asn Leu Ala
                115                 120                 125

Ser Ala Ile Arg Lys Ser Ser Gly Ser Gly Ala Ser Ser Val Val Gln
    130                 135                 140

Arg Pro Phe Arg Asp Arg Val Leu His Leu Leu Ala Leu Arg Pro Tyr
145                 150                 155                 160

Arg Lys Ala Glu Leu Leu Leu Arg Leu Gln Lys Asp Gly Leu Thr Gln
                165                 170                 175

Ala Asp Lys Asp Thr Leu Asp Ser Leu Leu Gln Gln Val Ala Ser Val
                180                 185                 190

Asn Pro Lys Asp Gly Thr Cys Thr Leu Gln Asp Cys Met Tyr Lys Ser
            195                 200                 205

Leu Gln Lys Asp Trp Pro Gly Tyr Ser Glu Gly Asp Arg Gln Leu Leu
    210                 215                 220

Lys Arg Met Leu Met Arg Lys Leu Cys Gln Pro Gln Asn Ala Thr Thr
225                 230                 235                 240

Asp Ser Ser Pro Pro Arg Glu His Gly Arg Ser Ala Ser Pro Ser Gln
                245                 250                 255

Lys Arg Arg Thr Asp Phe Ile Asp Pro Leu Ala Ser Lys Lys Pro Arg
                260                 265                 270

Ile Ser His Phe Thr Gln Arg Ala Gln Pro Thr Leu Asn Gly Lys Leu
            275                 280                 285

Gly Ala Pro Asn Gly His Glu Thr Leu Leu Pro Val Pro Gly Pro Thr
290                 295                 300

Pro Ser Asp Thr Phe Ser Ser His Leu Pro Pro Arg Leu Glu Pro
305                 310                 315                 320

Pro Arg Thr His Asp Pro Leu Ala Asp Val Ser Asn Asp Leu Gly His
                325                 330                 335

Ser Thr Gln Asp Tyr Lys His Gln Glu Ala Thr Pro Ala Pro Ala Pro
                340                 345                 350

His Phe Gly Leu Pro Leu Leu Thr Asp Phe Pro Gln Gly Glu Gln Pro
            355                 360                 365

Ile Ser Ser Ser His Thr His Ser Arg Pro Lys Lys Ser Lys Lys
370                 375                 380

His Lys Asp Lys Glu Arg Pro Glu Glu Arg Pro Ala Pro Gln
385                 390                 395                 400

Pro Asp Ala Pro Thr Ala Pro Ala Leu Pro Pro Asp Ala Pro Gly Leu
                405                 410                 415

Asn Gly Ala Cys Asp Asn Glu Pro Thr Ser Leu Ser Glu Thr Pro
                420                 425                 430

(2) INFORMATION FOR SEQ ID NO:6:

(i) SEQUENCE CHARACTERISTICS:
          (A) LENGTH: 757 base pairs
          (B) TYPE: nucleic acid
          (C) STRANDEDNESS: double
```

(D) TOPOLOGY: linear (ii) MOLECULE TYPE: DNA (genomic)

(ix) FEATURE:
        (A) NAME/KEY: CDS
        (B) LOCATION: join(1..717, 721..756)

(xi) SEQUENCE DESCRIPTION: SEQ ID NO:6:

```
CGA GAA CAC ACA GGC AAA CCC ACC ACG AGT AGC TCA GAA GCA TGT CGC        48
Arg Glu His Thr Gly Lys Pro Thr Thr Ser Ser Ser Glu Ala Cys Arg
 1               5                  10                  15

TTC TGT GGT TCC AGG AGT GGA ACA GAG TTA TCT GCT GTT GGC AGT GTT        96
Phe Cys Gly Ser Arg Ser Gly Thr Glu Leu Ser Ala Val Gly Ser Val
                20                  25                  30

TGT TCT GAT GCA GAT TGC CAG GAA TAC GCT AAG ATA GCC TGT AGT AAG       144
Cys Ser Asp Ala Asp Cys Gln Glu Tyr Ala Lys Ile Ala Cys Ser Lys
         35                  40                  45

ACG CAT CCT TGT GGC CAT CCA TGC GGG GGT GTT AAA AAC GAA GAG CAC       192
Thr His Pro Cys Gly His Pro Cys Gly Gly Val Lys Asn Glu Glu His
 50                  55                  60

TGT CTG CCC TGT CTA CAC GGC TGT GAC AAA AGT GCC ACA AGC CTG AAG       240
Cys Leu Pro Cys Leu His Gly Cys Asp Lys Ser Ala Thr Ser Leu Lys
 65                  70                  75                  80

CAA GAC GCC GAT GAC ATG TGC ATG ATA TGT TTC ACC GAA GCG CTC TCG       288
Gln Asp Ala Asp Asp Met Cys Met Ile Cys Phe Thr Glu Ala Leu Ser
                 85                  90                  95

GCA GCA CCA GCC ATT CAG CTG GAT TGT AGT CAC ATA TTC CAC TTA CAG       336
Ala Ala Pro Ala Ile Gln Leu Asp Cys Ser His Ile Phe His Leu Gln
            100                 105                 110

TGC TGT CGG CGA GTA TTA GAA AAT CGA TGG CTT GGC CCA AGG ATA ACA       384
Cys Cys Arg Arg Val Leu Glu Asn Arg Trp Leu Gly Pro Arg Ile Thr
        115                 120                 125

TTT GGA TTT ATA TCT TGT CCC ATT TGC AAG AAC AAA ATT AAT CAC ATA       432
Phe Gly Phe Ile Ser Cys Pro Ile Cys Lys Asn Lys Ile Asn His Ile
    130                 135                 140

GTA CTA AAA GAC CTA CTT GAT CCA ATA AAA GAA CTC TAT GAG GAT GTC       480
Val Leu Lys Asp Leu Leu Asp Pro Ile Lys Glu Leu Tyr Glu Asp Val
145                 150                 155                 160

AGA AGA AAA GCC TTA ATG AGA TTG GAA TAT GAA GGT CTG CAT AAG AGT       528
Arg Arg Lys Ala Leu Met Arg Leu Glu Tyr Glu Gly Leu His Lys Ser
                165                 170                 175

GAA GCT ATC ACA ACT CCT GGT GTG AGG TTT TAT AAT GAC CCA GCT GGT       576
Glu Ala Ile Thr Thr Pro Gly Val Arg Phe Tyr Asn Asp Pro Ala Gly
            180                 185                 190

TAT GCA ATG AAT AGA TAT GCA TAT TAT GTG TGC TAC AAA TGC AGA AAG       624
Tyr Ala Met Asn Arg Tyr Ala Tyr Tyr Val Cys Tyr Lys Cys Arg Lys
        195                 200                 205

GCA TAT TTT GGT GGT GAA GCT CGC TGC GAT GCT GAG GCT GGA CGG GGA       672
Ala Tyr Phe Gly Gly Glu Ala Arg Cys Asp Ala Glu Ala Gly Arg Gly
    210                 215                 220

GAT GAT TAT GAT CCC AGA GAG CTC ATT TGT GGT ACC GAG AGC GTT           717
Asp Asp Tyr Asp Pro Arg Glu Leu Ile Cys Gly Thr Glu Ser Val
225                 230                 235

TAG GTG AAA CAT ATC ATG CAC ATG TCA TCG GCG TCT TGC T                 757
    Val Lys His Ile Met His Met Ser Ser Ala Ser Cys
    240                 245                 250
```

(2) INFORMATION FOR SEQ ID NO:7:

(i) SEQUENCE CHARACTERISTICS:
        (A) LENGTH: 251 amino acids
        (B) TYPE: amino acid (D) TOPOLOGY: linear (ii) MOLECULE TYPE: protein (xi) SEQUENCE DESCRIPTION: SEQ ID NO:7:

```
Arg Glu His Thr Gly Lys Pro Thr Thr Ser Ser Glu Ala Cys Arg
 1               5                  10                  15

Phe Cys Gly Ser Arg Ser Gly Thr Glu Leu Ser Ala Val Gly Ser Val
                20                  25                  30

Cys Ser Asp Ala Asp Cys Gln Glu Tyr Ala Lys Ile Ala Cys Ser Lys
            35                  40                  45

Thr His Pro Cys Gly His Pro Cys Gly Gly Val Lys Asn Glu Glu His
        50                  55                  60

Cys Leu Pro Cys Leu His Gly Cys Asp Lys Ser Ala Thr Ser Leu Lys
65                  70                  75                  80

Gln Asp Ala Asp Asp Met Cys Met Ile Cys Phe Thr Glu Ala Leu Ser
                85                  90                  95

Ala Ala Pro Ala Ile Gln Leu Asp Cys Ser His Ile Phe His Leu Gln
                100                 105                 110

Cys Cys Arg Arg Val Leu Glu Asn Arg Trp Leu Gly Pro Arg Ile Thr
            115                 120                 125

Phe Gly Phe Ile Ser Cys Pro Ile Cys Lys Asn Lys Ile Asn His Ile
    130                 135                 140

Val Leu Lys Asp Leu Leu Asp Pro Ile Lys Glu Leu Tyr Glu Asp Val
145                 150                 155                 160

Arg Arg Lys Ala Leu Met Arg Leu Glu Tyr Glu Gly Leu His Lys Ser
                165                 170                 175

Glu Ala Ile Thr Thr Pro Gly Val Arg Phe Tyr Asn Asp Pro Ala Gly
                180                 185                 190

Tyr Ala Met Asn Arg Tyr Ala Tyr Tyr Val Cys Tyr Lys Cys Arg Lys
            195                 200                 205

Ala Tyr Phe Gly Gly Glu Ala Arg Cys Asp Ala Glu Ala Gly Arg Gly
        210                 215                 220

Asp Asp Tyr Asp Pro Arg Glu Leu Ile Cys Gly Thr Glu Ser Val Val
225                 230                 235                 240

Lys His Ile Met His Met Ser Ser Ala Ser Cys
                245                 250
```

(2) INFORMATION FOR SEQ ID NO:8:

(i) SEQUENCE CHARACTERISTICS:
        (A) LENGTH: 599 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..597

(xi) SEQUENCE DESCRIPTION: SEQ ID NO:8:

```
ATG GCG GCT GGG ACC CTG TAC ACG TAT CCT GAA AAC TGG AGG GCC TTC        48
Met Ala Ala Gly Thr Leu Tyr Thr Tyr Pro Glu Asn Trp Arg Ala Phe
            255                 260                 265

AAG GCT CTC ATC GCT GCT CAG TAC AGC GGG GCT CAG GTC CGC GTG CTC        96
Lys Ala Leu Ile Ala Ala Gln Tyr Ser Gly Ala Gln Val Arg Val Leu
            270                 275                 280

TCC GCA CCA CCC CAC TTC CAT TTT GGC CAA ACC AAC CGC ACC CCT GAA       144
```

```
Ser Ala Pro Pro His Phe His Phe Gly Gln Thr Asn Arg Thr Pro Glu
    285                 290                 295

TTT CTC CGC AAA TTT CCT GCC GGC AAG GTC CCA GCA TTT GAG GGT GAT     192
Phe Leu Arg Lys Phe Pro Ala Gly Lys Val Pro Ala Phe Glu Gly Asp
300                 305                 310                 315

GAT GGA TTC TGT GTG TTT GAG AGC AAC GCC ATT GCC TAC TAT GTG AGC     240
Asp Gly Phe Cys Val Phe Glu Ser Asn Ala Ile Ala Tyr Tyr Val Ser
                320                 325                 330

AAT GAG GAG CTG CGG GGA AGT ACT CCA GAG GCA GCA GCC CAG GTG GTG     288
Asn Glu Glu Leu Arg Gly Ser Thr Pro Glu Ala Ala Ala Gln Val Val
            335                 340                 345

CAG TGG GTG AGC TTT GCT GAT TCC GAT ATA GTG CCC CCA GCC AGT ACC     336
Gln Trp Val Ser Phe Ala Asp Ser Asp Ile Val Pro Pro Ala Ser Thr
        350                 355                 360

TGG GTG TTC CCC ACC TTG GGC ATC ATG CAC CAC AAC AAA CAG GCC ACT     384
Trp Val Phe Pro Thr Leu Gly Ile Met His His Asn Lys Gln Ala Thr
365                 370                 375

GAG AAT GCA AAG GAG GAA GTG AGG CGA ATT CTG GGG CTG CTG GAT GCT     432
Glu Asn Ala Lys Glu Glu Val Arg Arg Ile Leu Gly Leu Leu Asp Ala
380                 385                 390                 395

TAC TTG AAG ACG AGG ACT TTT CTG GTG GGC GAA CGA GTG ACA TTG GCT     480
Tyr Leu Lys Thr Arg Thr Phe Leu Val Gly Glu Arg Val Thr Leu Ala
                400                 405                 410

GAC ATC ACA GTT GTC TGC ACC CTG TTG TGG CTC TAT AAG CAG GTT CTA     528
Asp Ile Thr Val Val Cys Thr Leu Leu Trp Leu Tyr Lys Gln Val Leu
            415                 420                 425

GAG CCT TCT TTC CGC CAG GCC TTT CCC AAT ACC AAC CGC TGG TTC CTC     576
Glu Pro Ser Phe Arg Gln Ala Phe Pro Asn Thr Asn Arg Trp Phe Leu
        430                 435                 440

ACC TGC ATT AAC CAG CCC CAG TT                                      599
Thr Cys Ile Asn Gln Pro Gln
445                 450

(2) INFORMATION FOR SEQ ID NO:9:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:9:

Met Ala Ala Gly Thr Leu Tyr Thr Tyr Pro Glu Asn Trp Arg Ala Phe
1               5                   10                  15

Lys Ala Leu Ile Ala Ala Gln Tyr Ser Gly Ala Gln Val Arg Val Leu
            20                  25                  30

Ser Ala Pro Pro His Phe His Phe Gly Gln Thr Asn Arg Thr Pro Glu
        35                  40                  45

Phe Leu Arg Lys Phe Pro Ala Gly Lys Val Pro Ala Phe Glu Gly Asp
    50                  55                  60

Asp Gly Phe Cys Val Phe Glu Ser Asn Ala Ile Ala Tyr Tyr Val Ser
65                  70                  75                  80

Asn Glu Glu Leu Arg Gly Ser Thr Pro Glu Ala Ala Ala Gln Val Val
                85                  90                  95

Gln Trp Val Ser Phe Ala Asp Ser Asp Ile Val Pro Pro Ala Ser Thr
            100                 105                 110

Trp Val Phe Pro Thr Leu Gly Ile Met His His Asn Lys Gln Ala Thr
        115                 120                 125

Glu Asn Ala Lys Glu Glu Val Arg Arg Ile Leu Gly Leu Leu Asp Ala
```

```
                    130                 135                 140
Tyr Leu Lys Thr Arg Thr Phe Leu Val Gly Glu Arg Val Thr Leu Ala
145                 150                 155                 160

Asp Ile Thr Val Val Cys Thr Leu Leu Trp Leu Tyr Lys Gln Val Leu
                    165                 170                 175

Glu Pro Ser Phe Arg Gln Ala Phe Pro Asn Thr Asn Arg Trp Phe Leu
                180                 185                 190

Thr Cys Ile Asn Gln Pro Gln
            195

(2) INFORMATION FOR SEQ ID NO:10:

(i) SEQUENCE CHARACTERISTICS:
        (A) LENGTH: 725 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(1..492, 496..546, 550..723)

(xi) SEQUENCE DESCRIPTION: SEQ ID NO:10:

AAA GCT TTA GAG GAG ACC AAA GCC TAT ACA ACC CAA TCT CTA GCT AGT       48
Lys Ala Leu Glu Glu Thr Lys Ala Tyr Thr Thr Gln Ser Leu Ala Ser
  1               5                  10                  15

GTT GCT TAT CAA ATA AAT GCA TTG GCC AAC AAT GTA CTC CAG TTG CTG       96
Val Ala Tyr Gln Ile Asn Ala Leu Ala Asn Asn Val Leu Gln Leu Leu
                 20                  25                  30

GAT ATC CAA GCC TCT CAG CTT CGG AGA ATG GAG TCT TCC ATC AAT CAT      144
Asp Ile Gln Ala Ser Gln Leu Arg Arg Met Glu Ser Ser Ile Asn His
             35                  40                  45

ATC TCA CAG ACT GTG GAT ATT CAT AAG GAG AAA GTG GCA CGA AGA GAG      192
Ile Ser Gln Thr Val Asp Ile His Lys Glu Lys Val Ala Arg Arg Glu
 50                  55                  60

ATT GGT ATT TTG ACA ACA AAT AAG AAT ACA TCA AGA ACT CAC CAA ATA      240
Ile Gly Ile Leu Thr Thr Asn Lys Asn Thr Ser Arg Thr His Gln Ile
 65                  70                  75                  80

ATA GCA CCT GCG AAT ATG GAG CGC CCT GTA AGG TAT ATT CGG AAA CCT      288
Ile Ala Pro Ala Asn Met Glu Arg Pro Val Arg Tyr Ile Arg Lys Pro
                 85                  90                  95

ATC GAT TAC ACA GTT CTG GAT GAT GTG GGC CAT GGT GTC AAG CAT GGA      336
Ile Asp Tyr Thr Val Leu Asp Asp Val Gly His Gly Val Lys His Gly
            100                 105                 110

AAT AAC CAG CCT GCA AGA ACT GGC ACA CTG TCG AGA ACA AAT CYT CCT      384
Asn Asn Gln Pro Ala Arg Thr Gly Thr Leu Ser Arg Thr Asn Xaa Pro
        115                 120                 125

AYT CAG AAA CCG CCA AGT CCT CCC ATG TCA GGC CGG GGA ACA CTG GGA      432
Xaa Gln Lys Pro Pro Ser Pro Pro Met Ser Gly Arg Gly Thr Leu Gly
130                 135                 140

CGG AAT ACT CCT TAT AAA ACC CTG GAA CCT GTT AAA CCC CCA CAG TTC      480
Arg Asn Thr Pro Tyr Lys Thr Leu Glu Pro Val Lys Pro Pro Gln Phe
145                 150                 155                 160

CTA ATG ACT ATA TGA CCA GTC CTG CTA GGC TTG GAA GTC AGC ATA GTC      528
Leu Met Thr Ile     Pro Val Leu Leu Gly Leu Glu Val Ser Ile Val
                        165                 170                 175

CAG GCA GGA CAG CAT CTT TAA ATC AGA GAC CAA GGA CAC ACA GTG GAA      576
Gln Ala Gly Gln His Leu     Ile Arg Asp Gln Gly His Thr Val Glu
                180                     185                 190

GTA GTG GAG GAA GTG GAA GTC GAG AAA ACA GTG GTA GCA GTA GTA TTG      624
```

```
Val Val Glu Glu Val Glu Val Glu Lys Thr Val Val Ala Val Val Leu
            195                 200                 205

GCA TTC CCA TTG CTG TGC CTA CAC TTT CGC CAC CCA CTA TTG GAC CAG      672
Ala Phe Pro Leu Leu Cys Leu His Phe Arg His Pro Leu Leu Asp Gln
            210                 215                 220

CAG CCC CGG GCT CAG CTC CTG GTT TCC CAG TAT GGC ACA ATG ACC AGG      720
Gln Pro Arg Ala Gln Leu Leu Val Ser Gln Tyr Gly Thr Met Thr Arg
            225                 230                 235

CAG AC                                                                725
Gln
```

(2) INFORMATION FOR SEQ ID NO:11:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:11:

```
Lys Ala Leu Glu Glu Thr Lys Ala Tyr Thr Thr Gln Ser Leu Ala Ser
 1               5                  10                  15

Val Ala Tyr Gln Ile Asn Ala Leu Ala Asn Asn Val Leu Gln Leu Leu
            20                  25                  30

Asp Ile Gln Ala Ser Gln Leu Arg Arg Met Glu Ser Ser Ile Asn His
            35                  40                  45

Ile Ser Gln Thr Val Asp Ile His Lys Glu Lys Val Ala Arg Arg Glu
 50                  55                  60

Ile Gly Ile Leu Thr Thr Asn Lys Asn Thr Ser Arg Thr His Gln Ile
 65                  70                  75                  80

Ile Ala Pro Ala Asn Met Glu Arg Pro Val Arg Tyr Ile Arg Lys Pro
            85                  90                  95

Ile Asp Tyr Thr Val Leu Asp Asp Val Gly His Gly Val Lys His Gly
            100                 105                 110

Asn Asn Gln Pro Ala Arg Thr Gly Thr Leu Ser Arg Thr Asn Xaa Pro
            115                 120                 125

Xaa Gln Lys Pro Pro Ser Pro Pro Met Ser Gly Arg Gly Thr Leu Gly
130                 135                 140

Arg Asn Thr Pro Tyr Lys Thr Leu Glu Pro Val Lys Pro Pro Gln Phe
145                 150                 155                 160

Leu Met Thr Ile Pro Val Leu Leu Gly Leu Glu Val Ser Ile Val Gln
            165                 170                 175

Ala Gly Gln His Leu Ile Arg Asp Gln Gly His Thr Val Glu Val Val
            180                 185                 190

Glu Glu Val Glu Val Glu Lys Thr Val Val Ala Val Val Leu Ala Phe
            195                 200                 205

Pro Leu Leu Cys Leu His Phe Arg His Pro Leu Leu Asp Gln Gln Pro
            210                 215                 220

Arg Ala Gln Leu Leu Val Ser Gln Tyr Gly Thr Met Thr Arg Gln
225                 230                 235
```

(2) INFORMATION FOR SEQ ID NO:12:

(i) SEQUENCE CHARACTERISTICS:
        (A) LENGTH: 477 base pairs
        (B) TYPE: nucleic acid
        (C) STRANDEDNESS: double
        (D) TOPOLOGY: linear (ii) MOLECULE TYPE: DNA (genomic)

(ix) FEATURE:
 (A) NAME/KEY: CDS
 (B) LOCATION: join(1..204, 208..477)

(xi) SEQUENCE DESCRIPTION: SEQ ID NO:12:

| CCG | CCG | CCT | TTA | TTA | GCT | GAG | CCA | TTA | CTT | GAG | AGG | GAT | GAA | GCG | GGA | 48 |
|---|---|---|---|---|---|---|---|---|---|---|---|---|---|---|---|---|
| Pro | Pro | Pro | Leu | Leu | Ala | Glu | Pro | Leu | Leu | Glu | Arg | Asp | Glu | Ala | Gly | |
| 1 | | | | 5 | | | | | 10 | | | | | 15 | | |

| GGA | GTG | GGT | GGC | CCC | GAT | GCC | GGG | CCG | GCC | ATG | CTT | TAC | GGG | CTT | GTA | 96 |
|---|---|---|---|---|---|---|---|---|---|---|---|---|---|---|---|---|
| Gly | Val | Gly | Gly | Pro | Asp | Ala | Gly | Pro | Ala | Met | Leu | Tyr | Gly | Leu | Val | |
| | | | 20 | | | | | 25 | | | | | 30 | | | |

| GGT | GAT | GGA | GAA | CTC | GCC | CAG | GTA | GTG | GCC | GAT | CAT | CTC | GGG | CTT | GAT | 144 |
|---|---|---|---|---|---|---|---|---|---|---|---|---|---|---|---|---|
| Gly | Asp | Gly | Glu | Leu | Ala | Gln | Val | Val | Ala | Asp | His | Leu | Gly | Leu | Asp | |
| | | 35 | | | | | 40 | | | | | 45 | | | | |

| CTC | CAC | CTG | GTT | GAA | GGT | CTT | GCC | GTT | GTA | GAC | GCC | CAC | CAT | GCT | GCC | 192 |
|---|---|---|---|---|---|---|---|---|---|---|---|---|---|---|---|---|
| Leu | His | Leu | Val | Glu | Gly | Leu | Ala | Val | Val | Asp | Ala | His | His | Ala | Ala | |
| 50 | | | | | 55 | | | | | 60 | | | | | | |

| CAC | CAT | CTC | GGG | TAG | GAT | GAT | CAT | GTC | CCG | CAG | GTG | CGT | CTT | CAC | CAC | 240 |
|---|---|---|---|---|---|---|---|---|---|---|---|---|---|---|---|---|
| His | His | Leu | Gly | | Asp | Asp | His | Val | Pro | Gln | Val | Arg | Leu | His | His | |
| 65 | | | | | 70 | | | | | 75 | | | | | | |

| TTC | CGG | CTT | CTC | CAT | GGG | CGG | CGC | CTC | CTT | CTT | GGC | CTT | GCG | CAG | GCG | 288 |
|---|---|---|---|---|---|---|---|---|---|---|---|---|---|---|---|---|
| Phe | Arg | Leu | Leu | His | Gly | Arg | Arg | Leu | Leu | Leu | Gly | Leu | Ala | Gln | Ala | |
| 80 | | | | | 85 | | | | | 90 | | | | | 95 | |

| CTT | CAG | CAG | GGA | GTG | CTG | CTT | CCG | CCG | CAG | GCC | CCG | GTT | CAG | CCG | CCG | 336 |
|---|---|---|---|---|---|---|---|---|---|---|---|---|---|---|---|---|
| Leu | Gln | Gln | Gly | Val | Leu | Leu | Pro | Pro | Gln | Ala | Pro | Val | Gln | Pro | Pro | |
| | | | | 100 | | | | | 105 | | | | | 110 | | |

| CCG | CTG | GCG | CGC | ACT | GTA | CAG | CTG | CAT | CAG | CTG | CTC | GTA | GGA | CAT | GTC | 384 |
|---|---|---|---|---|---|---|---|---|---|---|---|---|---|---|---|---|
| Pro | Leu | Ala | Arg | Thr | Val | Gln | Leu | His | Gln | Leu | Leu | Val | Gly | His | Val | |
| | | | 115 | | | | | 120 | | | | | 125 | | | |

| CAG | CAG | CTG | GTC | GAG | ATC | CAC | GCC | GCG | GTA | GGT | GAA | CTT | GCG | GAA | GGT | 432 |
|---|---|---|---|---|---|---|---|---|---|---|---|---|---|---|---|---|
| Gln | Gln | Leu | Val | Glu | Ile | His | Ala | Ala | Val | Gly | Glu | Leu | Ala | Glu | Gly | |
| | | 130 | | | | | 135 | | | | | 140 | | | | |

| CCG | CTT | CTT | CTT | CTG | CTC | TAC | TTC | TGC | CAT | CTT | GCC | GGC | GGC | CGC | | 477 |
|---|---|---|---|---|---|---|---|---|---|---|---|---|---|---|---|---|
| Pro | Leu | Leu | Leu | Leu | Leu | Tyr | Phe | Cys | His | Leu | Ala | Gly | Gly | Arg | | |
| 145 | | | | | 150 | | | | | 155 | | | | | | |

(2) INFORMATION FOR SEQ ID NO:13:

(i) SEQUENCE CHARACTERISTICS:
  (A) LENGTH: 158 amino acids
  (B) TYPE: amino acid
  (D) TOPOLOGY: linear (ii) MOLECULE TYPE: protein (xi) SEQUENCE DESCRIPTION: SEQ ID NO:13:

| Pro | Pro | Pro | Leu | Leu | Ala | Glu | Pro | Leu | Leu | Glu | Arg | Asp | Glu | Ala | Gly |
|---|---|---|---|---|---|---|---|---|---|---|---|---|---|---|---|
| 1 | | | | 5 | | | | | 10 | | | | | 15 | |

| Gly | Val | Gly | Gly | Pro | Asp | Ala | Gly | Pro | Ala | Met | Leu | Tyr | Gly | Leu | Val |
|---|---|---|---|---|---|---|---|---|---|---|---|---|---|---|---|
| | | | 20 | | | | | 25 | | | | | 30 | | |

| Gly | Asp | Gly | Glu | Leu | Ala | Gln | Val | Val | Ala | Asp | His | Leu | Gly | Leu | Asp |
|---|---|---|---|---|---|---|---|---|---|---|---|---|---|---|---|
| | | 35 | | | | | 40 | | | | | 45 | | | |

| Leu | His | Leu | Val | Glu | Gly | Leu | Ala | Val | Val | Asp | Ala | His | His | Ala | Ala |
|---|---|---|---|---|---|---|---|---|---|---|---|---|---|---|---|
| 50 | | | | | 55 | | | | | 60 | | | | | |

| His | His | Leu | Gly | Asp | Asp | His | Val | Pro | Gln | Val | Arg | Leu | His | His | Phe |
|---|---|---|---|---|---|---|---|---|---|---|---|---|---|---|---|
| 65 | | | | | 70 | | | | | 75 | | | | | 80 |

| Arg | Leu | Leu | His | Gly | Arg | Arg | Leu | Leu | Leu | Gly | Leu | Ala | Gln | Ala | Leu |
|---|---|---|---|---|---|---|---|---|---|---|---|---|---|---|---|
| | | | 85 | | | | | 90 | | | | | 95 | | |

| Gln | Gln | Gly | Val | Leu | Leu | Pro | Pro | Gln | Ala | Pro | Val | Gln | Pro | Pro |
|---|---|---|---|---|---|---|---|---|---|---|---|---|---|---|
| | | | 100 | | | | | 105 | | | | | 110 | |

```
Leu Ala Arg Thr Val Gln Leu His Gln Leu Val Gly His Val Gln
            115                 120                 125

Gln Leu Val Glu Ile His Ala Ala Val Gly Glu Leu Ala Glu Gly Pro
130                 135                 140

Leu Leu Leu Leu Leu Tyr Phe Cys His Leu Ala Gly Gly Arg
145                 150                 155
```

(2) INFORMATION FOR SEQ ID NO:14:

(i) SEQUENCE CHARACTERISTICS:
        (A) LENGTH: 411 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(1..378, 382..411)

(xi) SEQUENCE DESCRIPTION: SEQ ID NO:14:

```
GGG GAT GCA GGC GTG GTC CTC CTC CAG GTC CTT CAG GCA GAT CTC CAG        48
Gly Asp Ala Gly Val Val Leu Leu Gln Val Leu Gln Ala Asp Leu Gln
1               5                   10                  15

GTG CAG CTC GCC GGC GCC CGC GAT GAT GTG CTC TCC CGA CTC CTC GAT        96
Val Gln Leu Ala Gly Ala Arg Asp Asp Val Leu Ser Arg Leu Leu Asp
                20                  25                  30

GAT GCA CTG CAC CAT GGG GTC GGA CTT GGC CAG CCG CTT CAG CCC CTC       144
Asp Ala Leu His His Gly Val Gly Leu Gly Gln Pro Leu Gln Pro Leu
            35                  40                  45

CAC CAG CTT GGG CAG GTC AGC CGG GTT CTT GGC CTC CAC GGC CAC TCT       192
His Gln Leu Gly Gln Val Ser Arg Val Leu Gly Leu His Gly His Ser
        50                  55                  60

GAC AAC AGG GCT GAC GCT GAA CTT CAT CAC CCG CAT GTT GTG CGC GTG       240
Asp Asn Arg Ala Asp Ala Glu Leu His His Pro His Val Val Arg Val
65                  70                  75                  80

CTC GAA AGT GGT GAT GGT GCC CGT CTT CAC CAG GAA CTG GTC CAC GCC       288
Leu Glu Ser Gly Asp Gly Ala Arg Leu His Gln Glu Leu Val His Ala
                85                  90                  95

CAC GAG CCC ACA ATG TTC CCA CAA GGC ACA TCC TCG ATG GGC TCC ACG       336
His Glu Pro Thr Met Phe Pro Gln Gly Thr Ser Ser Met Gly Ser Thr
            100                 105                 110

TAT CGG GCC ATC ATC AAG ATT GTT CTC TGG ATT GGC TTC AGG               378
Tyr Arg Ala Ile Ile Lys Ile Val Leu Trp Ile Gly Phe Arg
        115                 120                 125

TAG AAG TCC TCC TCT TCC ACG GGT TTT ATT GGG                           411
    Lys Ser Ser Ser Ser Thr Gly Phe Ile Gly
                130                 135
```

(2) INFORMATION FOR SEQ ID NO:15:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO:15:

```
Gly Asp Ala Gly Val Val Leu Leu Gln Val Leu Gln Ala Asp Leu Gln
1               5                   10                  15

Val Gln Leu Ala Gly Ala Arg Asp Asp Val Leu Ser Arg Leu Leu Asp
                20                  25                  30
```

```
Asp Ala Leu His His Gly Val Gly Leu Gly Gln Pro Leu Gln Pro Leu
        35                  40                  45

His Gln Leu Gly Gln Val Ser Arg Val Leu Gly Leu His Gly His Ser
        50                  55                  60

Asp Asn Arg Ala Asp Ala Glu Leu His His Pro His Val Val Arg Val
 65             70                  75                      80

Leu Glu Ser Gly Asp Gly Ala Arg Leu His Gln Glu Leu Val His Ala
                85                  90                  95

His Glu Pro Thr Met Phe Pro Gln Gly Thr Ser Ser Met Gly Ser Thr
                100                 105                 110

Tyr Arg Ala Ile Ile Lys Ile Val Leu Trp Ile Gly Phe Arg Lys Ser
        115                 120                 125

Ser Ser Ser Thr Gly Phe Ile Gly
        130                 135
```

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Asp Tyr Lys Asp Asp Asp Lys
 1               5
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= epsilon-V1-2

(xi) SEQUENCE DESCRIPTION: SEQ ID NO:17:

```
Glu Ala Val Ser Leu Lys Pro Thr
 1               5
```

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= beta-C2-4

(xi) SEQUENCE DESCRIPTION: SEQ ID NO:18:

```
Ser Leu Asn Pro Glu Trp Asn Glu Thr
 1               5
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= beta-C2-1

(xi) SEQUENCE DESCRIPTION: SEQ ID NO:19:

```
Lys Gln Lys Thr Lys Thr Ile Lys
1               5
```

(2) INFORMATION FOR SEQ ID NO:20:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..13
        (D) OTHER INFORMATION: /label= beta-C2-2

(xi) SEQUENCE DESCRIPTION: SEQ ID NO:20:

```
Met Asp Pro Asn Gly Leu Ser Asp Pro Tyr Val Lys Leu
1               5                   10
```

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= beta-C2-3

(xi) SEQUENCE DESCRIPTION: SEQ ID NO:21:

```
Ile Pro Asp Pro Lys Ser Glu
1               5
```

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /note= "Scrambled beta-C2-1"

(xi) SEQUENCE DESCRIPTION: SEQ ID NO:22:

```
Thr Lys Gln Lys Lys Ile Thr Lys
1               5
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /note= "Control Peptide"

(xi) SEQUENCE DESCRIPTION: SEQ ID NO:23:

```
Leu Gln Lys Ala Gly Val Asp Gly
1               5
```

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= theta-V1-1

(xi) SEQUENCE DESCRIPTION: SEQ ID NO:24:

```
Gly Leu Ser Asn Phe Asp Cys Gly
1               5
```

(2) INFORMATION FOR SEQ ID NO:25:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..11
        (D) OTHER INFORMATION: /label= theta-V1-2

(xi) SEQUENCE DESCRIPTION: SEQ ID NO:25:

```
Tyr Val Glu Ser Glu Asn Gly Gln Met Tyr Ile
1               5                   10
```

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide (B) LOCATION: 1..10
            (D) OTHER INFORMATION: /label= theta-V1-3

(xi) SEQUENCE DESCRIPTION: SEQ ID NO:26:

Ile Val Lys Gly Lys Asn Val Asp Leu Ile
1               5                   10

(2) INFORMATION FOR SEQ ID NO:27:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..10
            (D) OTHER INFORMATION: /label= theta-V1-4

(xi) SEQUENCE DESCRIPTION: SEQ ID NO:27:

Asp Met Asn Glu Phe Glu Thr Glu Gly Phe
1               5                   10

(2) INFORMATION FOR SEQ ID NO:28:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..9
            (D) OTHER INFORMATION: /label= delta-V1-1

(xi) SEQUENCE DESCRIPTION: SEQ ID NO:28:

Ala Phe Asn Ser Tyr Glu Leu Gly Ser
1               5

(2) INFORMATION FOR SEQ ID NO:29:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..11
            (D) OTHER INFORMATION: /label= delta-V1-2

(xi) SEQUENCE DESCRIPTION: SEQ ID NO:29:

Ala Leu Ser Thr Glu Arg Gly Lys Thr Leu Val
1               5                   10

(2) INFORMATION FOR SEQ ID NO:30:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
              (A) NAME/KEY: Peptide
              (B) LOCATION: 1..10
              (D) OTHER INFORMATION: /label= delta-V1-3

(xi) SEQUENCE DESCRIPTION: SEQ ID NO:30:

Val Leu Met Arg Ala Ala Glu Glu Pro Val
1               5                   10

(2) INFORMATION FOR SEQ ID NO:31:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..10
              (D) OTHER INFORMATION: /label= delta-V1-4

(xi) SEQUENCE DESCRIPTION: SEQ ID NO:31:

Gln Ser Met Arg Ser Glu Asp Glu Ala Lys
1               5                   10

(2) INFORMATION FOR SEQ ID NO:32:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..7
              (D) OTHER INFORMATION: /label= epsilon-V1-1

(xi) SEQUENCE DESCRIPTION: SEQ ID NO:32:

Asn Gly Leu Leu Lys Ile Lys
1               5

(2) INFORMATION FOR SEQ ID NO:33:

(i) SEQUENCE CHARACTERISTICS:
              (A) LENGTH: 11 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..11
              (D) OTHER INFORMATION: /label= epsilon-V1-3

(xi) SEQUENCE DESCRIPTION: SEQ ID NO:33:

Leu Ala Val Phe His Asp Ala Pro Ile Gly Tyr
1               5                   10

(2) INFORMATION FOR SEQ ID NO:34:

(i) SEQUENCE CHARACTERISTICS:
              (A) LENGTH: 9 amino acids

```
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..9
              (D) OTHER INFORMATION: /label= epsilon-V1-4

(xi) SEQUENCE DESCRIPTION: SEQ ID NO:34:

Asp Asp Phe Val Ala Asn Cys Thr Ile
1               5

(2) INFORMATION FOR SEQ ID NO:35:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..10
              (D) OTHER INFORMATION: /label= epsilon-V1-5

(xi) SEQUENCE DESCRIPTION: SEQ ID NO:35:

Trp Ile Asp Leu Glu Pro Glu Gly Arg Val
1               5                   10

(2) INFORMATION FOR SEQ ID NO:36:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..10
              (D) OTHER INFORMATION: /label= epsilon-V1-6

(xi) SEQUENCE DESCRIPTION: SEQ ID NO:36:

His Ala Val Gly Pro Arg Pro Gln Thr Phe
1               5                   10

(2) INFORMATION FOR SEQ ID NO:37:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..8
              (D) OTHER INFORMATION: /label= epsilon-V1-7

(xi) SEQUENCE DESCRIPTION: SEQ ID NO:37:

Asn Gly Ser Arg His Phe Glu Asp
1               5
```

(2) INFORMATION FOR SEQ ID NO:38:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION: 1..7
       (D) OTHER INFORMATION: /label= nu-V1-1

(xi) SEQUENCE DESCRIPTION: SEQ ID NO:38:

Asn Gly Tyr Leu Arg Val Arg
1               5

(2) INFORMATION FOR SEQ ID NO:39:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION: 1..8
       (D) OTHER INFORMATION: /label= nu-V1-2

(xi) SEQUENCE DESCRIPTION: SEQ ID NO:39:

Glu Ala Val Gly Leu Gln Pro Thr
1               5

(2) INFORMATION FOR SEQ ID NO:40:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION: 1..11
       (D) OTHER INFORMATION: /label= nu-V1-3

(xi) SEQUENCE DESCRIPTION: SEQ ID NO:40:

Leu Ala Val Phe His Glu Thr Pro Leu Gly Tyr
1               5                   10

(2) INFORMATION FOR SEQ ID NO:41:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION: 1..8
       (D) OTHER INFORMATION: /label= nu-V1-4

(xi) SEQUENCE DESCRIPTION: SEQ ID NO:41:

```
Asp Phe Val Ala Asn Cys Thr Leu
1               5
```

(2) INFORMATION FOR SEQ ID NO:42:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /label= nu-V1-5

(xi) SEQUENCE DESCRIPTION: SEQ ID NO:42:

```
Trp Val Asp Leu Glu Pro Glu Gly Lys Val
1               5                   10
```

(2) INFORMATION FOR SEQ ID NO:43:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= nu-V1-6

(xi) SEQUENCE DESCRIPTION: SEQ ID NO:43:

```
His Ser Leu Phe Lys Lys Gly His
1               5
```

(2) INFORMATION FOR SEQ ID NO:44:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= nu-V1-7

(xi) SEQUENCE DESCRIPTION: SEQ ID NO:44:

```
Thr Gly Ala Ser Asp Thr Phe Glu Gly
1               5
```

(2) INFORMATION FOR SEQ ID NO:45:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9

(D) OTHER INFORMATION: /label= mu-V1-1

(xi) SEQUENCE DESCRIPTION: SEQ ID NO:45:

Met Ser Val Pro Pro Leu Leu Arg Pro
1               5

(2) INFORMATION FOR SEQ ID NO:46:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..11
        (D) OTHER INFORMATION: /label= mu-V1-2

(xi) SEQUENCE DESCRIPTION: SEQ ID NO:46:

Lys Phe Pro Glu Cys Gly Phe Tyr Gly Leu Tyr
1               5                   10

(2) INFORMATION FOR SEQ ID NO:47:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /label= lambda-V1-1

(xi) SEQUENCE DESCRIPTION: SEQ ID NO:47:

His Gln Val Arg Val Lys Ala Tyr Tyr Arg
1               5                   10

(2) INFORMATION FOR SEQ ID NO:48:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..11
        (D) OTHER INFORMATION: /label= lambda-V1-2

(xi) SEQUENCE DESCRIPTION: SEQ ID NO:48:

Tyr Glu Leu Asn Lys Asp Ser Glu Leu Leu Ile
1               5                   10

(2) INFORMATION FOR SEQ ID NO:49:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide

```
       (ix) FEATURE:
             (A) NAME/KEY: Peptide
             (B) LOCATION: 1..7
             (D) OTHER INFORMATION: /label= zeta-V1-1

(xi) SEQUENCE DESCRIPTION: SEQ ID NO:49:

Val Arg Leu Lys Ala His Tyr
1               5

(2) INFORMATION FOR SEQ ID NO:50:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1..6
             (D) OTHER INFORMATION: /label= zeta-V1-2

(xi) SEQUENCE DESCRIPTION: SEQ ID NO:50:

Val Asp Ser Glu Gly Asp
1               5

(2) INFORMATION FOR SEQ ID NO:51:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1..8
             (D) OTHER INFORMATION: /label= zeta-V1-3

(xi) SEQUENCE DESCRIPTION: SEQ ID NO:51:

Val Phe Pro Ser Ile Pro Glu Gln
1               5

(2) INFORMATION FOR SEQ ID NO:52:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1..9
             (D) OTHER INFORMATION: /label= delta-V3-1

(xi) SEQUENCE DESCRIPTION: SEQ ID NO:52:

Gln Gly Phe Glu Lys Lys Thr Gly Val
1               5

(2) INFORMATION FOR SEQ ID NO:53:

(i) SEQUENCE CHARACTERISTICS:
             (A) LENGTH: 9 amino acids
             (B) TYPE: amino acid
```

```
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= delta-V3-2

(xi) SEQUENCE DESCRIPTION: SEQ ID NO:53:

Asp Asn Asn Gly Thr Tyr Gly Lys Ile
1               5

(2) INFORMATION FOR SEQ ID NO:54:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= epsilon-V3-1

(xi) SEQUENCE DESCRIPTION: SEQ ID NO:54:

Ser Ser Pro Ser Glu Glu Asp Arg Ser
1               5

(2) INFORMATION FOR SEQ ID NO:55:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= epsilon-V3-2

(xi) SEQUENCE DESCRIPTION: SEQ ID NO:55:

Pro Cys Asp Gln Glu Ile Lys Glu
1               5

(2) INFORMATION FOR SEQ ID NO:56:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= epsilon-V3-3

(xi) SEQUENCE DESCRIPTION: SEQ ID NO:56:

Glu Asn Asn Ile Arg Lys Ala Leu Ser
1               5

(2) INFORMATION FOR SEQ ID NO:57:
```

```
        (i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1..8
             (D) OTHER INFORMATION: /label= epsilon-V3-4

(xi) SEQUENCE DESCRIPTION: SEQ ID NO:57:

Gly Glu Val Arg Gln Gly Gln Ala
1               5

(2) INFORMATION FOR SEQ ID NO:58:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1..15
             (D) OTHER INFORMATION: /label= lambda-V3-1

(xi) SEQUENCE DESCRIPTION: SEQ ID NO:58:

Met Asp Gln Ser Ser Met His Ser Asp His Ala Gln Thr Val Ile
1               5                   10                  15

(2) INFORMATION FOR SEQ ID NO:59:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1..7
             (D) OTHER INFORMATION: /label= lambda-V3-2

(xi) SEQUENCE DESCRIPTION: SEQ ID NO:59:

Leu Asp Gln Val Gly Glu Glu
1               5

(2) INFORMATION FOR SEQ ID NO:60:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION: 1..9
             (D) OTHER INFORMATION: /label= lambda-V3-3

(xi) SEQUENCE DESCRIPTION: SEQ ID NO:60:

Glu Ala Met Asn Thr Arg Glu Ser Gly
```

(2) INFORMATION FOR SEQ ID NO:61:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= mu-V3-1

(xi) SEQUENCE DESCRIPTION: SEQ ID NO:61:

Asp Pro Asp Ala Asp Gln Glu Asp Ser
1               5

(2) INFORMATION FOR SEQ ID NO:62:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= mu-V3-2

(xi) SEQUENCE DESCRIPTION: SEQ ID NO:62:

Ser Lys Asp Thr Leu Arg Lys Arg His
1               5

(2) INFORMATION FOR SEQ ID NO:63:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= mu-V3-3

(xi) SEQUENCE DESCRIPTION: SEQ ID NO:63:

Ile Thr Leu Phe Gln Asn Asp Thr Gly
1               5

(2) INFORMATION FOR SEQ ID NO:64:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= mu-V3-4

(xi) SEQUENCE DESCRIPTION: SEQ ID NO:64:

Gly Ser Asn Ser His Lys Asp Ile Ser
1               5

(2) INFORMATION FOR SEQ ID NO:65:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..9
         (D) OTHER INFORMATION: /label= theta-V3-1

(xi) SEQUENCE DESCRIPTION: SEQ ID NO:65:

Cys Ser Ile Lys Asn Glu Ala Arg Leu
1               5

(2) INFORMATION FOR SEQ ID NO:66:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..9
         (D) OTHER INFORMATION: /label= theta-V3-2

(xi) SEQUENCE DESCRIPTION: SEQ ID NO:66:

Gly Lys Arg Glu Pro Gln Gly Ile Ser
1               5

(2) INFORMATION FOR SEQ ID NO:67:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..9
         (D) OTHER INFORMATION: /label= theta-V3-3

(xi) SEQUENCE DESCRIPTION: SEQ ID NO:67:

Asp Glu Val Asp Lys Met Cys His Leu
1               5

(2) INFORMATION FOR SEQ ID NO:68:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (ix) FEATURE:
              (A) NAME/KEY: Peptide
              (B) LOCATION: 1..15
              (D) OTHER INFORMATION: /label= zeta-V3-1

(xi) SEQUENCE DESCRIPTION: SEQ ID NO:68:

Ser Gln Glu Pro Pro Val Asp Asp Lys Asn Glu Asp Ala Asp Leu
1               5                   10                  15

(2) INFORMATION FOR SEQ ID NO:69:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..7
              (D) OTHER INFORMATION: /label= zeta-V3-2

(xi) SEQUENCE DESCRIPTION: SEQ ID NO:69:

Ile Lys Asp Asp Ser Glu Asp
1               5

(2) INFORMATION FOR SEQ ID NO:70:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..9
              (D) OTHER INFORMATION: /label= zeta-V3-3

(xi) SEQUENCE DESCRIPTION: SEQ ID NO:70:

Pro Val Ile Asp Gly Met Asp Gly Ile
1               5

(2) INFORMATION FOR SEQ ID NO:71:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..8
              (D) OTHER INFORMATION: /label= beta-V3-1

(xi) SEQUENCE DESCRIPTION: SEQ ID NO:71:

Val Pro Pro Glu Gly Ser Glu Ala
1               5

(2) INFORMATION FOR SEQ ID NO:72:

(i) SEQUENCE CHARACTERISTICS:
              (A) LENGTH: 8 amino acids
              (B) TYPE: amino acid
              (C) STRANDEDNESS: single (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= alpha-V3-1

(xi) SEQUENCE DESCRIPTION: SEQ ID NO:72:

Ile Pro Glu Gly Asp Glu Glu Gly
1               5

(2) INFORMATION FOR SEQ ID NO:73:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= gamma-V3-1

(xi) SEQUENCE DESCRIPTION: SEQ ID NO:73:

Val Ala Asp Ala Asp Asn Cys Ser
1               5

(2) INFORMATION FOR SEQ ID NO:74:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= alpha-V5-1

(xi) SEQUENCE DESCRIPTION: SEQ ID NO:74:

Gln Leu Val Ile Ala Asn
1               5

(2) INFORMATION FOR SEQ ID NO:75:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= beta-I-V5-1

(xi) SEQUENCE DESCRIPTION: SEQ ID NO:75:

Lys Leu Phe Ile Met Asn
1               5

(2) INFORMATION FOR SEQ ID NO:76:

```
    (i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= beta-II-V5-1

(xi) SEQUENCE DESCRIPTION: SEQ ID NO:76:

Gln Glu Val Ile Arg Asn
1               5

(2) INFORMATION FOR SEQ ID NO:77:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= delta-V5-1

(xi) SEQUENCE DESCRIPTION: SEQ ID NO:77:

Lys Asn Leu Ile Asp Ser
1               5

(2) INFORMATION FOR SEQ ID NO:78:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= epsilon-V5-1

(xi) SEQUENCE DESCRIPTION: SEQ ID NO:78:

Glu Ala Ile Val Lys Gln
1               5

(2) INFORMATION FOR SEQ ID NO:79:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= nu-V5-1

(xi) SEQUENCE DESCRIPTION: SEQ ID NO:79:

Glu Gly His Leu Pro Met
1               5
```

(2) INFORMATION FOR SEQ ID NO:80:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= lambda-V5-1

(xi) SEQUENCE DESCRIPTION: SEQ ID NO:80:

Asp Asp Ile Val Arg Lys
1            5

(2) INFORMATION FOR SEQ ID NO:81:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= mu-V5-1

(xi) SEQUENCE DESCRIPTION: SEQ ID NO:81:

Ser Asp Ser Pro Glu Ala
1            5

(2) INFORMATION FOR SEQ ID NO:82:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= theta-V5-1

(xi) SEQUENCE DESCRIPTION: SEQ ID NO:82:

Arg Ala Leu Ile Asn Ser
1            5

(2) INFORMATION FOR SEQ ID NO:83:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
       (B) LOCATION: 1..6
       (D) OTHER INFORMATION: /label= zeta-V5-1

(xi) SEQUENCE DESCRIPTION: SEQ ID NO:83:

Glu Asp Ala Ile Lys Arg
1               5

(2) INFORMATION FOR SEQ ID NO:84:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= PRK1-1

(xi) SEQUENCE DESCRIPTION: SEQ ID NO:84:

Gln Asp Ser Lys Thr Lys Ile Asp
1               5

(2) INFORMATION FOR SEQ ID NO:85:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= PRK2-1

(xi) SEQUENCE DESCRIPTION: SEQ ID NO:85:

Gln Asp Ser Lys Thr Lys Ile Glu
1               5

(2) INFORMATION FOR SEQ ID NO:86:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= PRK1-2

(xi) SEQUENCE DESCRIPTION: SEQ ID NO:86:

Glu Leu Ala Val Phe Trp Arg Asp
1               5

(2) INFORMATION FOR SEQ ID NO:87:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:

(A) NAME/KEY: Peptide
            (B) LOCATION: 1..8
            (D) OTHER INFORMATION: /label= PRK2-2

(xi) SEQUENCE DESCRIPTION: SEQ ID NO:87:

Glu Ile Ser Val Tyr Trp Arg Asp
1               5

(2) INFORMATION FOR SEQ ID NO:88:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..7
            (D) OTHER INFORMATION: /label= PRK1-3

(xi) SEQUENCE DESCRIPTION: SEQ ID NO:88:

Met Glu Pro Gln Gly Cys Leu
1               5

(2) INFORMATION FOR SEQ ID NO:89:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..7
            (D) OTHER INFORMATION: /label= PRK2-3

(xi) SEQUENCE DESCRIPTION: SEQ ID NO:89:

Leu Glu Pro Gln Gly Thr Leu
1               5